US009040563B2

(12) United States Patent
Sebti et al.

(10) Patent No.: US 9,040,563 B2
(45) Date of Patent: May 26, 2015

(54) DUAL INHIBITORS OF FARNESYLTRANSFERASE AND GERANYLGERANYLTRANSFERASE I

(71) Applicants: H. Lee Moffitt Cancer Center and Research Institute, Inc., Tampa, FL (US); Yale University, New Haven, CT (US)

(72) Inventors: Said M. Sebti, Tampa, FL (US); Andrew Hamilton, Oxfordshire (GB)

(73) Assignees: H. Lee Moffitt Cancer Center and Research Institute, Inc., Tampa, FL (US); Yale University, New Haven, CT (US)

( * ) Notice: Subject to any disclaimer, the term of this patent is extended or adjusted under 35 U.S.C. 154(b) by 0 days.

(21) Appl. No.: 13/792,900

(22) Filed: Mar. 11, 2013

(65) Prior Publication Data

US 2013/0190355 A1    Jul. 25, 2013

Related U.S. Application Data

(63) Continuation of application No. PCT/US2011/051034, filed on Sep. 9, 2011.

(60) Provisional application No. 61/420,578, filed on Dec. 7, 2010, provisional application No. 61/381,321, filed on Sep. 9, 2010.

(51) Int. Cl.
| | |
|---|---|
| C07D 233/64 | (2006.01) |
| C07D 233/84 | (2006.01) |
| C07D 401/12 | (2006.01) |
| C07D 401/14 | (2006.01) |
| C07D 403/14 | (2006.01) |
| C07D 409/14 | (2006.01) |
| C07D 413/14 | (2006.01) |
| A61K 31/095 | (2006.01) |
| A61K 31/10 | (2006.01) |
| A61K 31/4164 | (2006.01) |
| A61K 31/417 | (2006.01) |
| A61K 31/66 | (2006.01) |
| C07D 403/12 | (2006.01) |

(52) U.S. Cl.
CPC ............ *C07D 233/64* (2013.01); *A61K 31/095* (2013.01); *A61K 31/10* (2013.01); *A61K 31/4164* (2013.01); *A61K 31/417* (2013.01); *A61K 31/66* (2013.01); *C07D 401/12* (2013.01); *C07D 401/14* (2013.01); *C07D 403/12* (2013.01); *C07D 403/14* (2013.01); *C07D 409/14* (2013.01); *C07D 413/14* (2013.01); *C07D 233/84* (2013.01)

(58) Field of Classification Search
None
See application file for complete search history.

(56) References Cited

U.S. PATENT DOCUMENTS

| | | | |
|---|---|---|---|
| 6,218,375 | B1 | 4/2001 | Raghavan et al. |
| 2004/0142888 | A1 | 7/2004 | Manne et al. |
| 2008/0312287 | A1* | 12/2008 | Hamilton et al. ............. 514/341 |

OTHER PUBLICATIONS

Fletcher et al., 53 J. Med. Chem. 6867-6888 (2010).*
Aziz et al., Saadia A. "Phosphatidylinositol-3-K inase as a Therapeutic Target in Melanoma." Clinical Cancer Research, 2009; 15(9): 3029-3036.
Fletcher et al., Steven. Structure-Based Design and Synthesis of Potent, Ethylenediamine-Based, Mammalian Farnesyltransferase Inhibitors as Anticancer Agents. NIH Public Access. J. Med. Chem., Oct. 14, 2010; 53(19): 6867-6888.
Steven Fletcher et al. "Structure-Based Design and Synthesis of Potent, Ethylenediamine-Based, Mammalian Farnesyltransferase Inhibitors as Anticancer Agents." Journal of Medicinal Chemistry, Publication Date (Web): Sep. 7, 2010, vol. 53, No. 19, pp. 6867-6888.
International Search Report and Written Opinion issued by the International Searching Authority on May 7, 2012 for International Patent Application No. PCT/US2011/051034 (having an international filed of Sep. 9, 2011).
International Preliminary Report on Patentablity issued by the International Bureau on Dec. 3, 2013 for International Patent Application No. PCT/US2011/051034 (having an international filed of Sep. 9, 2011).
Saadia A. Aziza et al. "Phosphatidylinositol-3-Kinase as a Therapeutic Target in Melanoma." Clinical Cancer Research, 2009, 15(9), pp. 3029-3036.
Ian M. Bell. "Inhibitors of Farnesyltransferase: A Rational Approach to Cancer Chemotherapy?" Journal of Medicinal Chemistry, 2004, vol. 47, No. 8, pp. 1869-1878.
Andrea D. Basso et al. "Farnesyl Transferase Inhibitors." Journal of Lipid Research, 2006, vol. 47, pp. 15-31.
Channing J. Der et al. "Isoprenoid Modification and Plasma-Membrane Association: Critical Factors for Ras Oncogenicity." Cancer Cells, 1991, vol. 3, No. 9, pp. 331-340.

(Continued)

*Primary Examiner* — Timothy R Rozof
(74) *Attorney, Agent, or Firm* — Robert J. Varkonyi; Smith & Hopen, P.A.

(57) ABSTRACT

Many GTPases such as Ras, Ral and Rho require post-translational farnestylation or geranylgeranylation for mediating malignant transformation. Dual farnesyltransferase (FT) (FTI) and geranylgeranyltransferase-I (GGT-1) inhibitors (GGTI) were developed as anticancer agents from based on an ethylenediamine scaffold. On the basis of a 4-fold substituted ethylenediamine scaffold, the inhibitors are structurally simple and readily derivatized, facilitating extensive structure-activity relationship studies. The most potent inhibitor is compound exhibited an in vitro hFTase $IC_{50}$ value of 25 nM and a whole cell H-Ras processing $IC_{50}$ value of 90 nM. Several of the inhibitors proved highly selective for hFTase over the related prenyltransferase enzyme geranylgeranyltransferase-I (GGTase-I). A crystal structure of an inhibitor cocrystallized with farnesyl pyrophosphate in the active site of rat FTase illustrates that the para-benzonitrile moiety is stabilized by a $\pi$-$\pi$ stacking interaction with the Y361$\beta$ residue, suggesting an importance of this component of the inhibitors.

14 Claims, 14 Drawing Sheets

(56) References Cited

OTHER PUBLICATIONS

Ronald J. Doll et al. "Farnesyltransferase Inhibitors as Anticancer Agents: Critical Crossroads." Current Opinion in Drug Discovery & Development, 2004, vol. 7, No. 4, pp. 478-486.

Richard T. Eastman et al. "Resistance to a Protein Farnesyltransferase Inhibitor in *Plasmodium falciparum*." The Journal of Biological Chemistry, 2005, vol. 280, No. 14, pp. 13554-13559.

Matthew P. Glenn et al. "Structurally Simple Farnesyltransferase Inhibitors Arrest the Growth of Malaria Parasites." Agnew Chem. Int. Ed. 2005, vol. 44, pp. 4903-4906.

Matthew P. Glenn et al. "Structurally Simple, Potent, Plasmodium Selective Farnesyltransferase Inhibitors that Arrest the Growth of Malaria Parasites." J. Med Chem. 2006, vol. 49, No. 19, pp. 5710-5727.

Jason Gotlib. "Farnesyltransferase Inhibitor Therapy in Acute Myelogenous Leukemia." Current Hematology Reports, 2005, vol. 4, pp. 77-84.

Michael A. Hast et al. "Structural Basis for Binding and Selectivity of Antimalarial and Anticancer Ethylenediamine Inhibitors to Protein Farnesyltransferase." Chem Biol. 2009, vol. 16, No. 2, pp. 181-192.

John T. Hunt et al. "Discovery of (R)-7-Cyano-2,3,4,5-tetrahydro-1-(1H-imidazol-4-ylmethyl)-3-(phenylmethyl)-4-(2-thienylsulfonyl)-1H-1,4-benzodiazepine (BMS-214662), a Farnesyltransferase Inhibitor with Potent Preclinical Antitumor Activity." Journal of Medicinal Chemistry, 2000, vol. 43, No. 20, pp: 3587-3595.

Bruce E. Johnson et al. "Farnesyl Transferase Inhibitors for Patients with Lung Cancer." Clinical Cancer Research, 2004, vol. 10, pp. 4254s-4257s.

Stephen B. Long et al. "The Crystal Structure of Human Protein Farnesyltransferase Reveals the Basis for Inhibition by CaaX Tetrapeptides and their Mimetics." Proc. Natl. Acad. Sci. U.S.A., 2001, vol. 98, No. 3, pp. 12948-12953.

Junko Ohkanda et al. "Structure-Based Design of imidazole-containing Peptidomimetic Inhibitors of Protein Farnesyltransferase." Organic & Biomolecular Chemistry, 2006, vol. 4, pp. 482-492.

Junko Ohkanda et al. "Design and Synthesis of Potent Nonpeptidic Farnesyltransferase Inhibitors Based on a Terphenyl Scaffold." Journal of Medicinal Chemistry, 2002, vol. 45, No. 1, pp. 177-188.

Yimin Qian. "Design and Structural Requirement of Potent Peptidomimetic Inhibitors of p21ras Farnesyltransferase." The Journal of Biological Chemistry, 1994, vol. 269, No. 17, pp. 12410-12413.

Yimin Qian. "Probing the Hydrophobic Pocket of Farnesyltransferase: Aromatic Substitution of CAAX Peptidomimetics Leads to Highly Potent Inhibitors." Bioorganic & Medical Chemistry, 1999, vol. 7, pp. 3011-3024.

S. Rao, al. et al "Phase III Double-Blind Placebo-Controlled Study of Farnesyl Transferase Inhibitor R115777 in Patients with Refractory Advanced Colorectal Cancer." Journal of Clinical Oncology, 2004, vol. 22, No. 19, pp. 3950-3597.

Jiazhi Sun et al. "Antitumor Efficacy of a Novel Class of Non-thiol-containing Peptidomimetic Inhibitors of Farnesyltransferase and Geranylgeranyltransferase I: Combination Therapy with the Cytotoxic Agents Cisplatin, Taxol, and Gemcitabine." Cancer Research, 1999, vol. 59, pp: 4919-1926.

Anil Vasudevan et al. "Potent, Highly Selective, and Non-Thiol Inhibitors of Protein Geranylgeranyltransferase-I." Journal of Medicinal Chemistry, 1999, vol. 42, No. 8, pp: 1333-1340.

Marc Venet et al. "Farnesyl Protein Transferase Inhibitor Zarnestra tm R115777—History of a Discovery." Current Topics in Medicinal Chemistry, 2003, vol. 3, No. 10, pp. 1095-1102.

Andreas Vogt et al. "Protein Geranylgeranylation, no Farnesylation, is Required for the G1 to S Phase Transition in Mouse Fibroblasts." Oncogene, 1996, vol. 13, pp: 1991-1999.

Fang L. Zhang et al. "Protein Prenylation: Molecular Mechanisms and Functional Consequences." Annu. Rev. Biochem., 1996, vol. 65, pp: 241-269.

CAS search. http://www.cas.org/ (last accessed Aug. 20, 2014).

* cited by examiner 2 (BMS-214662)

FGTI-2734

DUAL INHIBITORS OF FARNESYLTRANSFERASE AND GERANYLGERANYLTRANSFERASE I

CROSS REFERENCE TO RELATED APPLICATIONS

This application is a continuation of prior filed International Application, Serial Number PCT/US2011/051034, entitled "Duel Inhibitors of Farnesyltransferase and Geranylgeranyltransferase I", filed Sep. 9, 2011, which claims priority to U.S. Provisional Patent Application No. 61/381,321, entitled "Dual Inhibitors of Farnesyltransferase (FT) and Geranylgeranyltransferase I (GGT-I) as Novel Anti-Tumor Agents", filed on Sep. 9, 2010, and U.S. Provisional Patent Application No. 61/420,578, entitled "Dual Inhibitors of Farnesyltransferase (FT) and Geranylgeranyltransferase I (GGT-I) as Novel Anti-Tumor Agents", filed on Dec. 7, 2010, the contents of which are herein incorporated by reference into this disclosure.

GOVERNMENT SUPPORT STATEMENT

This invention was made with Government support under Grant No NCDDG/CA67771, awarded by National Cancer Institute. The Government has certain rights in the invention.

FIELD OF INVENTION

This invention relates to anti-tumor agents. Specifically, the invention provides dual inhibitors (FGTIs) for inhibiting human tumor growth.

BACKGROUND OF THE INVENTION

As the successful treatment of cancer remains a challenging goal, research into novel, selective, and less toxic chemotherapeutic agents is gathering pace (Bassou, 2006, J Lipid Res; Bell, Inhibitors of farnesyltransferase: A rational approach to cancer chemotherapy? *J. Med. Chem.* 2004, 8, 1869-1878; Doll, et al., Farnesyltransferase inhibitors as anticancer agents: critical crossroads. *Curr. Opin. Drug Discov. Devel.* 2004, 7, 478-486). Increased understanding of the cellular processes that lead to cancer has identified additional targets for the design of such chemotherapeutics. Ras, the protein product of the ras oncogene, is a small GTPase that is important in signal transduction, cell growth, and cell proliferation (Shields, J. M.; Pruitt, K.; McFall, A.; Shaub, A.; Der, C. J. Understanding Ras: "It ain't over 'til it's over." *Trends Cell Biol.* 2000, 10, 147-154). Mutations in Ras, which cause the protein to persistently bind GTP and thus become constitutively active, can lead to unregulated cell division; such Ras mutants are found in approximately 30% of human tumors (Bos, Ras Oncogenes in human cancer: A review. *Cancer Res.* 1989, 49, 4682-4689; Clark and Der, Ras proto-oncogene activation in human malignancy. In *Cellular Cancer Markers*; Garrett, C. T., Sell, S., Eds.; Humana Press: Totowa, N.J., 1995; pp 17-52). In the 1980s, it was reported that Ras required farnesylation to enhance its hydrophobicity and thereby facilitate its anchorage to the plasma membrane, a process necessary for its signaling function (Willumsen, et al., Harvey murine sarcoma virus p21 Ras protein: Biological and biochemical significance of the cysteine nearest the carboxy terminus. *EMBO J.* 1984, 3, 2581-2585; Casey, et al., p21 Ras is modified by a farnesyl isoprenoid. *Proc. Natl. Acad. Sci. U.S.A.* 1989, 86, 8323-8327).

The prenyltransferases are a family of zinc metallo-enzymes that catalyze the prenylation (addition of a prenyl group through a thioether linkage) of a particular set of proteins, many of which are crucial to signal transduction pathways, causing their localization to the plasma membrane and other cellular compartments and so rendering them biologically active (Liu, et al., RhoB Alteration Is Necessary for Apoptotic and Antineoplastic Responses to Farnesyltransferase Inhibitors. *Mol. Cell. Biol.* 2000, 20, 6105-6113). There are three members of the prenyltransferase family: farnesyltransferase (FTase), geranygeranyltransferase-I (GGTase-I), and geranygeranyltransferase-II (GGTase-II). FTase catalyzes the transfer of a farnesyl (C15 isoprenoid) group from the co-substrate farnesylpyrophosphate (FPP) to the cysteine residue within the C-terminus $C_{ala2}X$ tetrapeptide sequence of the target protein (including Ras and Rheb), where C=cysteine, a=an aliphatic amino acid, and X=methionine (M), serine (S), alanine (A), or glutamine (Q); (Chen, et al., Both Farnesylated and Geranylgeranylated RhoB Inhibit Malignant Transformation and Suppress Human Tumor Growth in Nude Mice. *J. Biol. Chem.* 2000, 275, 17974-17978). Likewise, GGTase-I catalyzes the corresponding S-geranylgeranylation by accelerating the transfer of the geranylgeranyl group (C20 isoprenoid) from GGPP to the cysteine within the C-terminus $C_{ala2}X$ sequence of the substrate protein (including Rho, Rap, and Ral) (Casey, Biochemistry of Protein Prenylation. *Lipid Res.* 1992, 33, 1731-1740), where this time X is usually leucine (L), isoleucine (I), or phenylalanine (F); (Chen, et al., Both Farnesylated and Geranylgeranylated RhoB Inhibit Malignant Transformation and Suppress Human Tumor Growth in Nude Mice. *J. Biol. Chem.* 2000, 275, 17974-17978). It is the identity of the X residue that dictates if a target protein is farnesylated or geranylgeranylated and is so-called the specificity residue. Finally, in a similar fashion, GGTase-II transfers two geranylgeranyl groups to protein trafficking Rab proteins that contain Cys-Cys or Cys-Ala-Cys sequences at the C-terminus (Chen, et al., Both Farnesylated and Geranylgeranylated RhoB Inhibit Malignant Transformation and Suppress Human Tumor Growth in Nude Mice. *J. Biol. Chem.* 2000, 275, 17974-17978).

The ability of some proteins to cause cancer depends on their modification by FT or GGT-1 with lipids called farnesyl or geranylgeranyl. Furthermore, cancer cells contain both farnesylated and geranylgeranylated cancer-causing proteins. Therefore, inhibiting FT or GGT-1 is a potential approach to combat cancer. However, inhibition of the farnesylation of some cancer-causing proteins such as K-Ras (encoded by one of the most frequently mutated cancer-causing genes in human cancers) leads to its geranylgeranylation keeping K-Ras active and rescuing cancer cells from FTI anti-tumor effects.

In addition to inhibiting FTase in vitro (Bell, Inhibitors of farnesyltransferase: A rational approach to cancer chemotherapy? *Exp. Opin. Ther. Patents* 2000, 10, 1813-1831), farnesyltransferase inhibitors (FTIs) have demonstrated antitumor activity in several animal models (Bell, Inhibitors of farnesyltransferase: A rational approach to cancer chemotherapy? *J. Med. Chem.* 2004, 8, 1869-1878). Clinically, however, the results are mixed. For example, a lack of activity was reported when Tipifarnib (R115777; Venet, et al., Farnesyl Protein Transferase Inhibitor ZARNESTRA R115777—History of a Discovery. *Curr. Top. Med. Chem.* 2003, 3, 1095-1102) was used against advanced colorectal and pancreatic cancers (Rao, et al. Phase III double-blind placebo-controlled study of farnesyl transferase inhibitor R115777 in patients with refractory advanced colorectal cancer. *J. Clin. Oncol.*

2004, 22, 3950-3957; Johnson, and Heymach, Farnesyl transferase inhibitors for patients with lung cancer. *Clin. Cancer Res.* 2004, 10, 4254s-4257s). In contrast, extremely encouraging results were observed when Tipifarnib was used against breast cancer in combination with cytotoxic agents (Gotlib, Farnesyltransferase inhibitor therapy in acute myelogenous leukemia. *Curr. Hematol. Rep.* 2005, 4, 77-84; Hunt, et al., Discovery of (R)-7-Cyano-2,3,4,5-tetrahydro-1-(1H-imidazol-4-ylmethyl)-3-(phenylmethyl)-4-(2-thienylsulfonyl)-1H-1,4-benzodiazepine (BMS-214662), a Farnesyltransferase Inhibitor with Potent Preclinical Antitumor Activity. *J. Med. Chem.* 2000, 43, 3587-3595). In recent years, it has become clear that aberrant Ras activity is not the only target for FTIs, and it is likely that other FTase substrates, such as Rheb, are also involved in oncogenesis (Liu, et al., Antitumor Activity of SCH 66336, an Orally Bioavailable Tricyclic Inhibitor of Farnesyl Protein Transferase, in Human Tumor Xenograft Models and Wap-ras Transgenic Mice. *Cancer Res.* 1998, 58, 4947-4956; Baum and Kirschmeier, Preclinical and clinical evaluation of farnesyltransferase inhibitors. *Curr. Oncol. Rep.* 2003, 5, 99-107; Taveras, et al., Sch-66336 (sarasar) and other benzocycloheptapyridyl farnesyl protein transferase inhibitors: discovery, biology and clinical observations. *Curr. Top. Med. Chem.* 2003, 3, 1103-1114; Prendergast and Rane, N. Farnesyltransferase Inhibitors: Mechanism and Applications. *Expert Opin. Invest. Drugs* 2001, 10, 2105-2116). Nonetheless, despite the now-apparent complexity of this system and the unclear molecular mechanisms by which FTIs operate, the past decade has seen many FTIs established as antiproliferative agents with high efficacy and low toxicity, validating the continued research into more drug-like FTIs as alternative chemotherapeutics for cancer (Bassou, 2006, *J Lipid Res*; Bell, Inhibitors of farnesyltransferase: A rational approach to cancer chemotherapy? *J. Med. Chem.* 2004, 8, 1869-1878; Doll, et al., Farnesyltransferase inhibitors as anticancer agents: critical crossroads. *Curr. Opin. Drug Discov. Devel.* 2004, 7, 478-486).

Previous research has focused on the design of peptidomimetic inhibitors of FTase based on the $C_{ala2}X$ tetrapeptide substrate (Zhang and Casey, Protein Prenylation: Molecular Mechanisms and Functional Consequences. *Annu. Rev. Biochem.* 1996, 65, 241-269; Der and Cox, Isoprenoid Modification and Plasma-Membrane Association: Critical Factors for Ras Oncogenicity. *Cancer Cells* 1991, 3, 331-340; Ohkanda, et al. Structure-based design of imidazole-containing peptidomimetic inhibitors of protein farnesyltransferase. *Org. Biomol. Chem.*, 2006, 4, 482-492; Qian, et al., Design and structural requirements of potent peptidomimetic inhibitors of p21ras farnesyltransferase. *J. Biol. Chem.* 1994, 269, 12410-12413).

SUMMARY OF INVENTION

Herein a novel series of ethylenediamine-based, mammalian dual GGTase/FTase inhibitors are described as anticancer compounds that were discovered by a "piggy-back" approach after the success of the core scaffold in a series of antimalarial plasmodial FTase inhibitors (Qian, et al., Probing the hydrophobic pocket of farnesyltransferase: aromatic substitution of CAAX peptidomimetics leads to highly potent inhibitors. *Bioorg. Med. Chem.* 1999, 7, 3011-3024). An extensive structure-activity relationship (SAR) study of these inhibitors is described, with both in vitro and whole cell data, including relative activities against FTase and GGTase-I.

Inhibition of the farnesylation of some cancer-causing proteins such as K-Ras leads to its geranylgeranylation keeping K-Ras active and rescuing cancer cells from FTI anti-tumor effects. Therefore, new compounds targeting FTase and GGTase-I are required. On the basis of a 4-fold substituted ethylenediamine scaffold, the inhibitors are structurally simple and readily derivatized, facilitating the extensive structure-activity relationship (SAR) study reported herein. The most potent inhibitor is compound 1f, which exhibited an in vitro hFTase $IC_{50}$ value of 25 nM and a whole cell H-Ras processing $IC_{50}$ value of 90 nM. Moreover, it is noteworthy that several inhibitors proved highly selective for hFTase (up to 333-fold) over the related prenyltransferase enzyme geranylgeranyltransferase-I (GGTase-I). A crystal structure of inhibitor 1a cocrystallized with farnesyl pyrophosphate (FPP) in the active site of rat FTase illustrates that the para-benzonitrile moiety of 1a is stabilized by a π-π stacking interaction with the Y361β residue, suggesting a structural explanation for the observed importance of this component of the inhibitors. Dual farnesylation/geranylgernylation inhibitors that are more potent at inhibiting tumor cell growth that either FTIs or GGTIs when used alone as single agents are identified to address the shortcomings in single FTIs or GGTIs.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
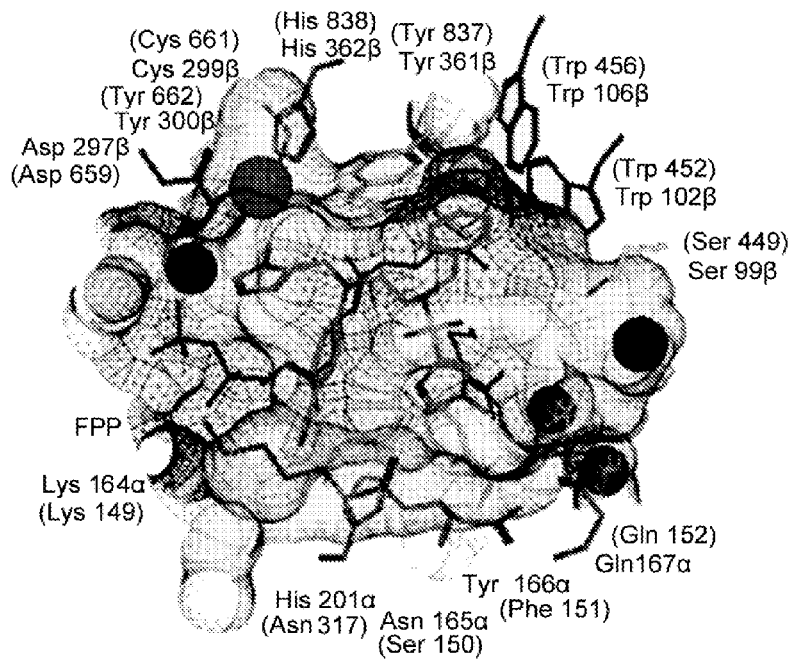
FIG. 1 is an illustration of the high scoring active site conformation of inhibitor 1a, seen as a stick molecule, as identified by flexible ligand GOLD (Fletcher, S., Cummings, C. G., Rivas, K., Katt, W. P., Harney, C., Buckner, F. S., Chakrabarti, D., Sebti, S. M., Gelb, M. H., Van Voorhis, W. C., Hamilton, A. D. Potent, *Plasmodium*-selective farnesyltransferase inhibitors that arrest the growth of malaria parasites: structure-activity relationships of ethylenediamine-analogue scaffolds and homology model validation. *J. Med. Chem.* 2008, 51, 5176-5197) docking experiments using a Connoly analytical surface graphical representation developed in Insight II (Sun, et al., Both farnesyltransferase and geranylgeranyltransferase I inhibitors are required for inhibition of oncogenic K-Ras prenylation but each alone is sufficient to suppress human tumor growth in nude mouse xenografts. *Oncogene*, 1998, 16, 1467-1473), red hydrophobic to blue hydrophilic.

As used herein "treating" or "treatment" means any manner of managing the cancer by medicinal or other therapies, such that the cancer no longer increases in size, metastasizes, or otherwise progresses in severity on a diagnosis scale, such as Duke's classification or any other classification system known. In some embodiments, the treatment ameliorates the disease through a reduction in size or otherwise beneficially improves the severity on a diagnosis scale.

As used herein, "patient" means humans, nonhuman primates, dogs, cats, sheep, goats, horses, cows, pigs and rodents. In particular, the "subjects" of the present invention are organisms in need of treatment for a cancer or pre-cancer or lesion thereof.

As used herein, the term "cancer" refers to a neoplasm, cancer, or precancerous lesion. The neoplasm or cancer may be benign or malignant. This includes cells or tissues that have characteristics relating to changes that may lead to malignancy or cancer, such as mutations controlling cell growth and proliferation. Examples include adenomatous growths in breast and prostate tissue, or for example, conditions of dysplastic nevus syndromes, polyposis syndromes, prostatic dysplasia, and other neoplasms, whether clinically identifiable or not.

In the method of the present invention, the fetal neural stem cells of the present invention can be administered in various ways as would be appropriate to implant in the central nervous system, including but not limited to parenteral, including intravenous and intraarterial administration, and intraventricular administration. Administration will often depend upon the disease or condition treated and may preferably be via a parenteral route, for example, intravenously.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The "therapeutically effective amount" for purposes herein is thus determined by such considerations as are known in the art. A therapeutically effective amount of the compounds, or any combination thereof is that amount of active compound or pharmaceutical agent that elicits the biological or medicinal response in a tissue, system, animal or human that is being sought by a researcher, veterinarian, medical doctor or other clinician. The amount of Shp2 inhibitors, compounds described herein, or any combination thereof must be effective to achieve a response, including but not limited to total prevention of (e.g., protection against) and to improved survival rate or more rapid recovery, or improvement or elimination of symptoms associated with neoproliferative disease, including but not limited to, cancer and precancerous lesions, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/ or (vii) relieve to some extent one or more of the symptoms associated with the cancer.

Useful concentration of the compounds are administered at approximately 50 to approximately 100 mg/kg daily, or at concentrations of 50 mg/kg, 60 mg/kg, 70 mg/kg, 80 mg/kg, 90 mg/kg, or 100 mg/kg.

Previous reports describe the design and synthesis of inhibitors of *Plasmodium falciparum* farnesyl transferase (PfFTase); (Qian, et al., Probing the hydrophobic pocket of farnesyltransferase: aromatic substitution of CAAX peptidomimetics leads to highly potent inhibitors. *Bioorg. Med. Chem.* 1999, 7, 3011-3024; Vasudevan, et al., Potent, highly selective, and non-thiol inhibitors of protein geranylgeranyltransferase-I. *J. Med. Chem.* 1999, 42, 1333-1340; Sun, et al. Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. *Cancer Res.* 1999, 59, 4919-4926; Ohkanda, et al., Design and synthesis of potent nonpeptidic farnesyltransferase inhibitors based on a terphenyl scaffold. *J. Med. Chem.* 2002, 45, 177-188). A homology model of the active site of PfFTase suggests the presence of four subpockets (Glenn, et al., Structurally simple farnesyltransferase inhibitors arrest the growth of malaria parasites. *Angew. Chem., Int. Ed.* 2005, 44, 4903-4906; Glenn, et al., Structurally simple, potent, *Plasmodium* selective farnesyltransferase inhibitors that arrest the growth of malaria parasites. *J. Med. Chem.* 2006, 49, 5710-5727). By employing the computational modeling program GOLD (Fletcher, et al., Potent, *Plasmodium*-selective farnesyltransferase inhibitors that arrest the growth of malaria parasites: structure-activity relationships of ethylenediamine-analogue scaffolds and homology model validation. *J. Med. Chem.* 2008, 51, 5176-5197), an ethylenediamine scaffold was identified with both nitrogens doubly substituted, allowing simultaneous access to these four subpockets that allowed for development of inhibitors of PfFTase. Inhibition of the farnesylation of some cancer-causing proteins such as K-Ras leads to its geranylgeranylation keeping K-Ras active and rescuing cancer cells from FTI anti-tumor effects. On the basis of a 4-fold substituted ethylenediamine scaffold, the inhibitors are structurally simple and readily derivatized, facilitating the extensive structure-activity relationship (SAR) studies, with both in vitro and whole cell data, including relative activities against FTase and GGTase-I.

Figure 2:
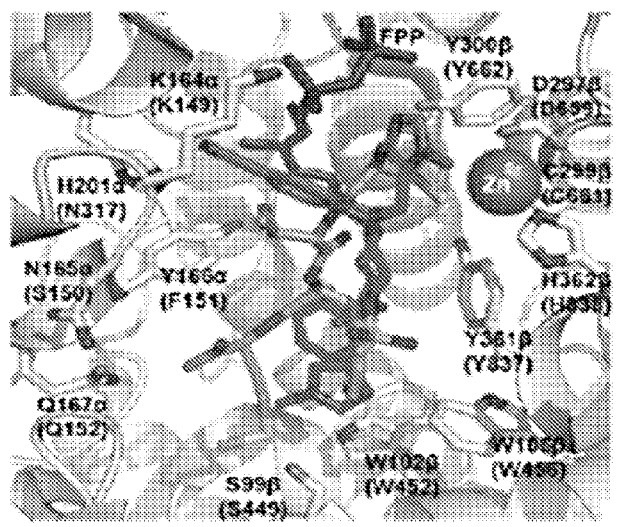
FIG. 2 is a "cartoon" graphical representation of inhibitor 1a, seen as a dark stick molecule illustration, developed in PyMOL (Hast, et al., Structural basis for binding and selectivity of antimalarial and anticancer ethylenediamine inhibitors to protein farnesyltransferase. *Chem. Biol.* 2009, 16, 181-192) and overlaid with the peptide inhibitor CVFM, seen as a light grey stick molecule, from the rFTase crystal structure. Binding surface of rat FTase (PDB ID:1JCR (Long, et al. The crystal structure of human protein farnesyltransferase reveals the basis for inhibition by CaaX tetrapeptides and their mimetics. *Proc. Natl. Acad. Sci. U.S.A.* 2001, 98, 12948-12953)), values in parentheses refer to corresponding residues in PfFTase (Glenn, et al., Structurally simple farnesyltransferase inhibitors arrest the growth of malaria parasites. *Angew. Chem., Int. Ed.* 2005, 44, 4903-4906; Glenn, et al., Structurally simple, potent, *Plasmodium* selective farnesyltransferase inhibitors that arrest the growth of malaria parasites. *J. Med. Chem.* 2006, 49, 5710-5727).
Figure 3:
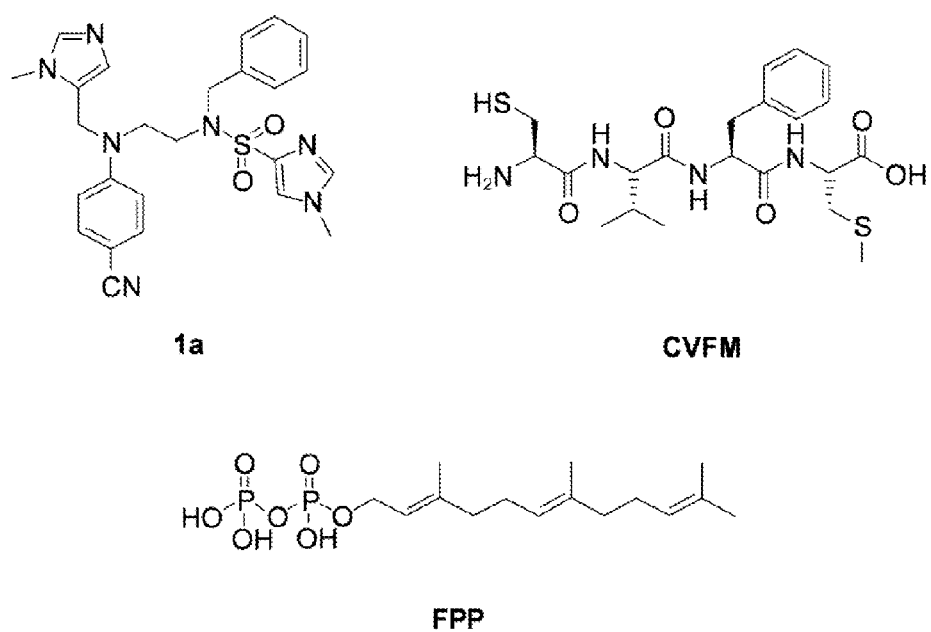
FIG. 3 is an illustration of three compounds, compound 1a, CVFM, and FPP.

Compounds based on this scaffold, including 1a, seen in FIGS. 1-3, in which the choice of four substituents (para-benzonitrile, imidazolylmethyl, arylmethyl, and heterocycle-substituted sulfonyl) was influenced by the BMS series of tetrahydrobenzodiazepine-based (Eastman, et al., Resistance to a protein farnesyltransferase inhibitor in *Plasmodium falciparum. J. Biol. Chem.* 2005, 280, 13554-13559) and tetrahydroquinoline (THQ)-based (GOLD reference) FTase inhibitors, proved particularly potent inhibitors of PfFTase, both in vitro and in infected erythrocytes (Qian, et al., Probing the hydrophobic pocket of farnesyltransferase: aromatic substitution of CAAX peptidomimetics leads to highly potent inhibitors. *Bioorg. Med. Chem.* 1999, 7, 3011-3024; Vasudevan, et al., Potent, highly selective, and non-thiol inhibitors of protein geranylgeranyltransferase-I. *J. Med. Chem.* 1999, 42, 1333-1340; Sun, et al. Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. *Cancer Res.* 1999, 59, 4919-4926; Ohkanda, et al., Design and synthesis of potent nonpeptidic farnesyltransferase inhibitors based on a terphenyl scaffold. *J. Med. Chem.* 2002, 45, 177-188). Although PfFTase is significantly larger than rat FTase (rFTase) in both the R- (472 vs 379 residues) and β-subunits (621 vs 437 residues), the differences are mainly due to insertions in the PfFTase protein sequence, and overall there is minimal difference in the residues that form the active site (Qian, et al., Probing the hydrophobic pocket of farnesyltransferase: aromatic substitution of CAAX peptidomimetics leads to highly potent inhibitors. *Bioorg. Med. Chem.* 1999, 7, 3011-3024; Glenn, et al., Structurally simple farnesyltransferase inhibitors arrest the growth of malaria parasites. *Angew. Chem., Int. Ed.* 2005, 44, 4903-4906; Glenn, et al., Structurally simple, potent, *Plasmodium* selective farnesyltransferase inhibitors that arrest the growth of malaria parasites. *J. Med. Chem.* 2006, 49, 5710-5727). Of the sequence segments in the model of PfFTase, there is 23% identity (53% similarity) for the R-subunit between PfFTase and rat FTase isoforms and 37% (56%) for the β-subunit. Therefore, it was anticipated that the PfFTase inhibitors may also inhibit mammalian FTase, binding in the same subdomains but, in certain instances, with differing active site residues (i.e., PfFTase→rFTase (PDB ID:1JCR):S150→N165α, F151→Y166α, N317→H201α) (Glenn, et al., Structurally simple farnesyltransferase inhibitors arrest the growth of malaria parasites. *Angew. Chem., Int. Ed.* 2005, 44, 4903-4906; Glenn, et al., Structurally simple, potent, *Plasmodium* selective farnesyltransferase inhibitors that arrest the growth of malaria parasites. *J. Med. Chem.* 2006, 49, 5710-5727; Long, et al., The crystal structure of human protein farnesyltransferase reveals the basis for inhibition by CaaX tetrapeptides and their mimetics. *Proc. Natl. Acad. Sci. U.S.A.* 2001, 98, 12948-12953), providing a route to inhibitor selectivity for the mammalian isoform of the enzyme.

Figure 4:
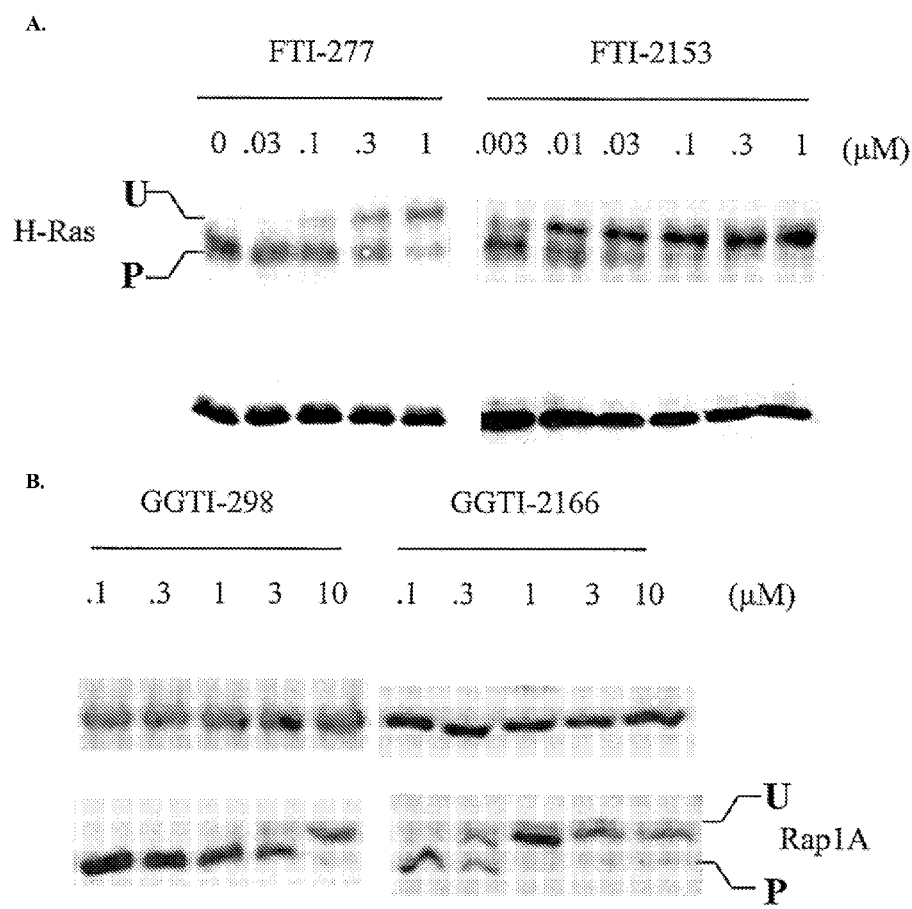
FIGS. 4A and B are blots showing inhibition of H-Ras and Rap1A processing by farnesyltransferase inhibitors and geranygeranyltransferase-I inhibitors. Oncogenic H-Ras-transformed NIH-3T3 cells were treated with the indicated concentrations of FTI-277, FTI-2153, GGTI-298, and GGTI-2166, harvested and processed for SDS-PAGE, and immunoblotted with either Ras or Rap1A antibodies as described in "Materials and Methods." U and P, unprocessed and processed proteins, respectively. Data are representative of at least three independent experiments.

Specifically, as with an almost identical analogue of 1a in the homology model of the active site of PfFTase, as seen in FIGS. 4A and B, it was hypothesized that the more basic of the two imidazoles, the 3-methyl-3H-imidazol-4-ylmethyl substituent of 1a, would bind the zinc ion (itself held in place by D297β (D659), C661β (C299), and H362β (H838), where the labels in parentheses represent the corresponding residues in PfFTase). In addition, the para-benzonitrile moiety was envisioned to bind in the mostly hydrophobic pocket constructed from the tetramethylene portion of the side chain of K164α (K149) and Y166α (F151) and whose deepest point forms a hydrophilic domain (H201α (N317) and N165α (S150)). It was considered that the benzyl moiety would bind in the hydrophobic pocket comprising W102β (W452), W106β (W456), and Y361β (Y837), and finally that the sulfonylimidazole would bind in the hydrophilic domain formed by R202β (R564) and three water molecules participating in a hydrogen-bonded network between S99β (S449) and Q167α (Q152).

To maintain consistency with the GOLD docking experiments of ethylenediamine-based inhibitors in the homology model of the active site of PfFTase (Qian, et al., Probing the hydrophobic pocket of farnesyltransferase: aromatic substitution of CAAX peptidomimetics leads to highly potent inhibitors. *Bioorg. Med. Chem.* 1999, 7, 3011-3024; Vasudevan, et al., Potent, highly selective, and non-thiol inhibitors of protein geranylgeranyltransferase-I. *J. Med. Chem.* 1999, 42, 1333-1340; Sun, et al., Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. *Cancer Res.* 1999, 59, 4919-4926; Ohkanda, et al., Design and synthesis of potent nonpeptidic farnesyltransferase inhibitors based on a terphenyl scaffold. *J. Med. Chem.* 2002, 45, 177-188), the only constraint imposed in the flexible ligand GOLD docking with compound 1a in the active site of rFTase (PDB ID: 1JCR) was that the more basic, nonsulfonylated imidazole should again bind the $Zn^{2+}$ ion. Because of the flexible nature of the ethylenediamine scaffold in 1a, it was undesirable to bias the docking results any further and no further constraints were used. Moreover, despite the similarities of the pendant groups in 1a and the former clinical candidate (R)-7-cyano-2,3,4,5-tetrahydro-1-(1H-imidazol-4-ylmethyl)-3-(phenylmethyl)-4-(2-thienylsulfonyl)-1H-1,4-benzodiazepine (BMS-214662, 2, (Eastman, et al., Resistance to a protein farnesyltransferase inhibitor in *Plasmodium falciparum*. *J. Biol. Chem.* 2005, 280, 13554-13559)), the knowledge of the crystal structure of 2 (Vogt, et al., Protein geranylgeranylation, not farnesylation, is required for the G1 to S phase transition in mouse fibroblasts. *Oncogene*, 1996, 13, 1991-1999) was not used given its more rigid tetrahydrobenzodiazepine scaffold. As was anticipated owing to the similarities in the active sites of PfFTase and rFTase, several low energy GOLD docked poses of compound 1a in rFTase demonstrated an almost identical binding mode to that observed with a very close analogue of 1a in PfFTase, with the biggest difference being that the nonsulfonylated imidazole binds the $Zn^{2+}$ ion in a cation-π-stacking fashion, as opposed to a direct interaction of the nonmethylated τ-N lone pair of electrons, which may be compared between FIGS. 4A and B and FIG. 1. FIG. 1 illustrates one such high scoring (low energy) docked pose of compound 1a by atom type, using the graphical representation (Connoly analytical surface, Insight II (Sun, et al., Both farnesyltransferase and geranylgeranyltransferase I inhibitors are required for inhibition of oncogenic K-Ras prenylation but each alone is sufficient to suppress human tumor growth in nude mouse xenografts. *Oncogene*, 1998, 16, 1467-1473)) employed in previous publications. The binding surface of rFTase incorporates the co-substrate farnesyl pyrophosphate (FPP: farnesyl; pyrophosphate). This binding mode of 1a overlays well with the tetrapeptide inhibitor CVFM from the rFTase crystal structure as shown in FIG. 2, in which an alternative graphical representation ("cartoon", PyMOL; (Hast, et al., Structural basis for binding and selectivity of antimalarial and anticancer ethylenediamine inhibitors to protein farnesyltransferase. *Chem. Biol.* 2009, 16, 181-192)) was used. Given the highly flexible nature of the ligand, coupled with the fact that the other high scoring poses from studies (data not shown) were generally posed such that the scaffold projected functionalities to positions similar to those seen in FIG. 2, it is believed that the molecule, in solution, would occupy pockets as previously predicted as part of an ensemble of binding motifs.

Figure 5:
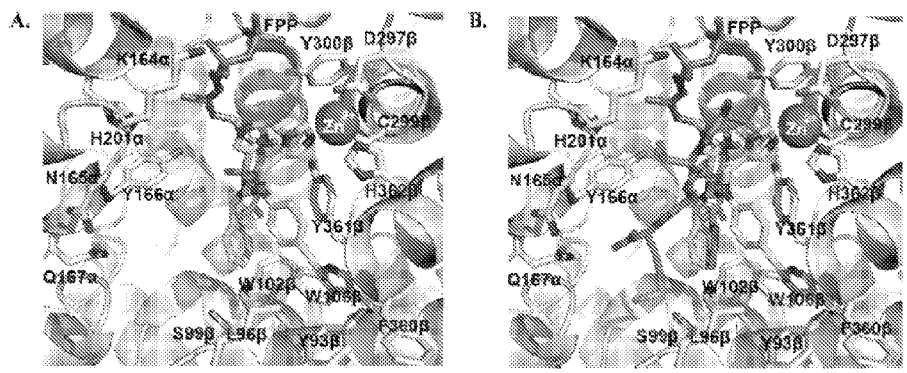
FIG. 5 are crystal structures of (A) inhibitor 1a, seen in the center of the image, bound to rFTase (PDB ID: 3E32) (Vogt. et al., Protein geranylgeranylation, not farnesylation, is required for G1 to S phase transition in mouse fibroblasts. *Oncogene.* 1996; 13:1991-1999), and (B) inhibitor 1a overlaid with the tetrapeptide inhibitor CVFM, molecule on outside of the image, from PDB ID 1JCR.

The crystal structure of the 1a:FPP:rFTase ternary complex, seen in FIG. 5A; PDB ID: 3E32, was recently reported (Hast, et al. Structural basis for binding and selectivity of antimalarial and anticancer ethylenediamine inhibitors to protein farnesyltransferase. *Chem. Biol.* 2009, 16, 181-192). As a comparison, in FIG. 5B the crystal structure of 1a was superimposed with that of the tetrapeptide substrate CVFM (PDB ID: 1JCR). Interestingly, the crystal structure shows that the ethylenediamine-based FTIs actually adopt a different binding mode to that predicted, as seen in FIG. 2. FIG. 5A illustrates that the para-benzonitrile substituent of 1a is oriented toward the product exit groove and is partially stabilized by a stacking interaction with Y361β. The rings are approximately 30° offset from parallel, with the distance between them ranging from 3.8 to 4.9 Å. The binding pocket also consists of F360β (not shown in Figure), Y9313, L96β, and W106β, creating a generally hydrophobic environment for this moiety. Inhibitor 1a possesses two N-methylimidazole groups: one coordinates the catalytic zinc ion (2.0 Å distance) through its non-methylated τ-nitrogen in place of the $C_{ala2}X$ box cysteine residue, while the second (at the sulfonamide position) is stacked between the first N-methylimidazole (3.7 Å distance) and the first isoprene of FPP (4.1 Å distance). The nonmethylated τ-nitrogen of the N-methylimidazole-4-sulfonyl group also makes a single, weak polar contact (3.7 Å distance) to the side chain hydroxyl of Y361β. The phenyl substituent of 1a binds in a pocket formed by W106β, W102β, and L96β, essentially the $a_2$ residue binding site of the $C_{ala2}X$ substrate, and occupying almost exactly the same space as the phenylalanine side chain of CVFM, as seen in FIG. 5B.

Figure 6:
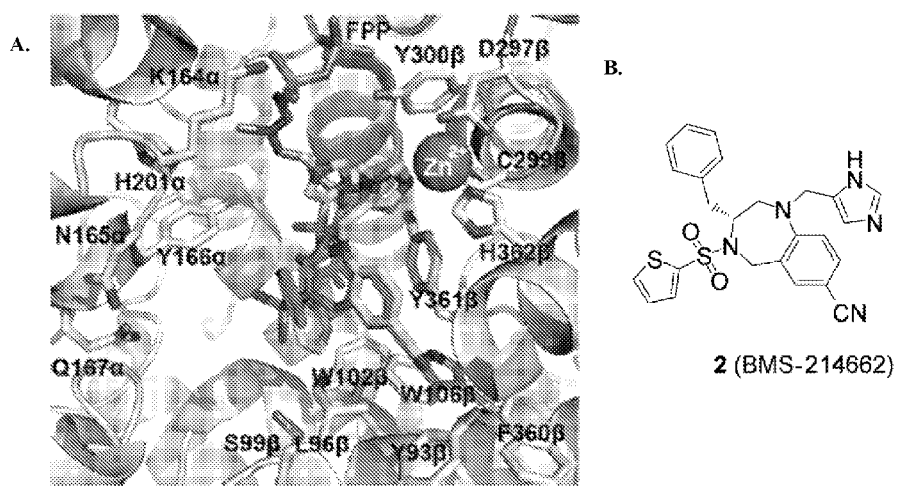
FIGS. 6(A) and (B) show (A) the overlay of the crystal structures of the ternary complexes of 1a (Vogt. et al., Protein geranylgeranylation, not farnesylation, is required for G1 to S phase transition in mouse fibroblasts. *Oncogene.* 1996; 13:1991-1999), dark grey molecule in center of image, and 2 (Vogt, et al., Protein geranylgeranylation, not farnesylation, is required for the G1 to S phase transition in mouse fibroblasts. *Oncogene,* 1996, 13, 1991-1999), light grey molecule on the outside of the image, with FPP in rFTase and (B) the structure of compound 2.

Several similarities exist between the chemical substituents and binding mode of the ethylenediamine inhibitor 1a with tetrahydrobenzodiazepine 2 whose crystal structures are overlaid in FIGS. 6A and B. The binding modes of the para-benzonitrile group and the nonsulfonylated N-methylimidazole group of the ethylenediamine inhibitor 1a are nearly indistinguishable from the similar substituents in 2, with the imidazole of 2 coordinating the catalytic zinc ion like the nonsulfonylated N-methylimidazole of the 1a. The scaffold nitrogen atoms bearing these substituents in both 1a and 2 occupy similar locations. The para-benzonitrile groups extends into the exit groove, with the positions of the cyano group nitrogen atoms from the two molecules differing by only ~0.4 Å, a value close to the estimated error in crystallographic coordinates. Finally, the phenyl substituents of both compounds take advantage of the aromatic character of the $C_{ala2}X$ $a_2$ residue site, interacting with tryptophan residues 102β and 106β. The sulfonamide positions of both compounds exhibit the greatest differences in binding modes. As a consequence, the scaffold nitrogen bearing this group in the tetrahydrobenzodiazepine ring of 2 is not oriented in a spatially similar location to the nitrogen bearing the second, sulfonylated N-methylimidazole of 1a, which is sandwiched between the first isoprene of the lipid substrate and the zinc-coordinating N-methylimidazole moiety.

By contrast, the thienyl group of 2 is largely solvent-exposed and binds in a manner resembling the $a_1$ residue of the $C_{ala2}X$ motif. This ring is primarily stabilized by stacking on the tetrahydrobenzodiazepine ring scaffold itself, as opposed to interacting with the enzyme active site or lipid substrate.

The crystal structure of the ternary complex of 1a:FPP:FTase:FPP was solved toward the end of this research; the medicinal chemistry research program that follows was driven by piggybacking on the inhibitors of PfFTase and, to a lesser extent, the GOLD docking result presented in FIG. 1.

Example

Solvents $CH_2Cl_2$, $CH_3CN$ and DMF were dried on an Innovative Techonology SPS-400 dry solvent system. Anhydrous MeOH and DMSO (Sigma-Aldrich Co. LLC., St. Louis, Mo.) and used as obtained from the manufacturer. Molecular sieves were activated by heating to 300° C. under vacuum overnight. All reactions were performed under an atmosphere of dry nitrogen in oven-dried glassware and were monitored for completeness by thin-layer chromatography (TLC) using silica gel (visualized by UV light, or developed by treatment with $KMnO_4$ stain or Hanessian's stain).

$^1H$ and $^{13}C$ NMR spectra were recorded on Bruker AM 400 MHz and Bruker AM 500 MHz spectrometers in either $CDCl_3$, MeOH-$d_4$ or DMSO-$d_6$. Chemical shifts (B) are reported in parts per million after calibration to residual isotopic solvent. Coupling constants (J) are reported in Hz. Mass spectrometry was performed using electrospray ionization on either a Varian MAT-CH-5 (HRMS) or Waters Micromass ZQ (LRMS).

Before biological testing, all new target molecules (1b, 1c, 1ah-1an, 1aw, 10-13, 18a-18h, 20a-20c) were subjected to further purification by reversed-phase HPLC (rpHPLC). Analysis and purification by rpHPLC were performed using either Phenonenex Luna 5 μm C18 (2) 250×21 mm column run at 15 mL/min (preparative) or a Microsorb-MV 300 A C18 250 mm×4.6 mm column run at 1 mL/min (analytical), using gradient mixtures of (A) water with 0.1% TFA and (B) 10:1 acetonitrile/water with 0.1% TFA. Appropriate product fractions were pooled and lyophilized to dryness, affording the inhibitors as fluffy white powders as their TFA salts. Inhibitor purity was confirmed by analytical rpHPLC using linear gradients from 100% A to 100% B, with changing solvent composition of either (I) 4.5% or (II) 1.5% per min after an initial 2 min of 100% A. For reporting HPLC data, percentage purity is given in parentheses after the retention time for each condition.

In vitro inhibition assays for FTase and GGTase-I were conducted by measuring the incorporation of $[^3H]FPP$ and $[^3H]GGPP$ into recombinant H-Ras-CVLS and H-Ras-CVLL, respectively, as previously described (Vogt, et al., Protein geranylgeranylation, not farnesylation, is required for the G1 to S phase transition in mouse fibroblasts. *Oncogene*, 1996, 13, 1991-1999). The in vivo inhibition of farnesylation and geranylgeranylation was determined based on the level of inhibition by synthetic compounds of H-Ras and Rap1A processing, respectively (Sun, et al., Both farnesyltransferase and geranylgeranyltransferase I inhibitors are required for inhibition of oncogenic K-Ras prenylation but each alone is sufficient to suppress human tumor growth in nude mouse xenografts. *Oncogene*, 1998, 16, 1467-1473). Briefly, oncogenic H-Ras-transformed NIH3T3 cells were treated with various concentrations of inhibitors, and the cell lysates were isolated and proteins separated on a 12.5% SDS-PAGE gel. The separated proteins were transferred to nitrocellulose and immunoblotted using an anti-Ras antibody (Y13-258) or an anti-Rap1A antibody (SantaCruz Biotechnology, Santa Cruz, Calif.), respectively. Antibody reactions were visualized using either peroxidase-conjugated goat anti-rat IgG or goat anti-rabbit IgG (Jackson ImmunoResearch, West Grove, Pa.) and an enhanced chemiluminescence detection system.

Figure 7:
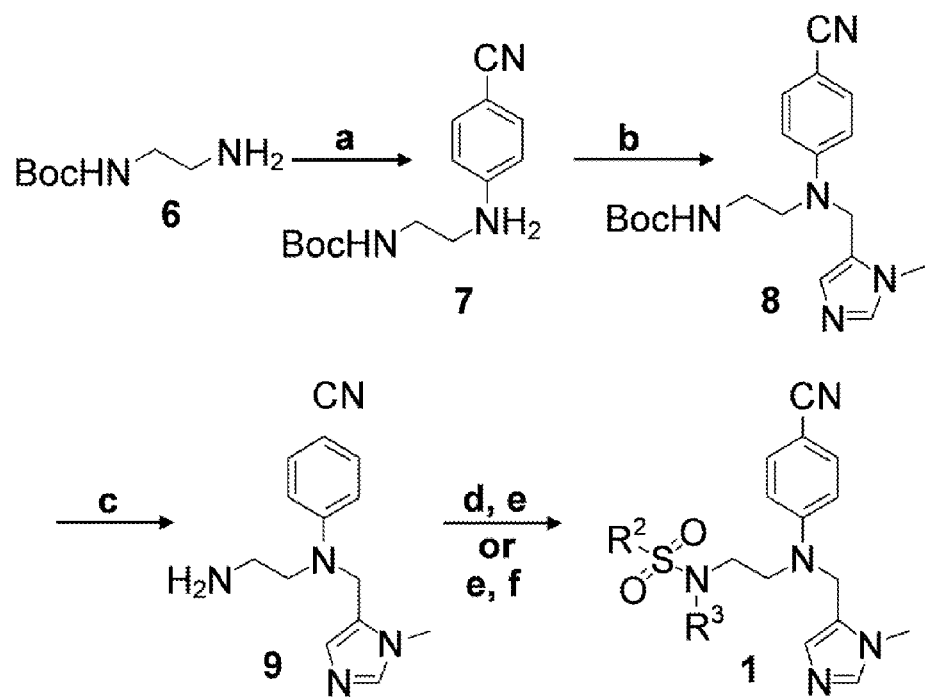
FIG. 7 is an illustration of reaction scheme 1 for the present invention. Reagents and conditions are: (a) para-fluorobenzonitrile, DIPEA, DMSO, 120° C., 48 hr, 89%; (b) (1) LDA, THF, −78° C., 30 min, (2) 5-cholomethyl-1-methyl-1-H-imidazole.HCl, (Qian, Y.; et al., Probing the hydrophobic pocket of farnesyltransferase: aromatic substitution of CAAX peptidomimetics leads to highly potent inhibitors. *Bioorg. Med. Chem.* 1999, 7, 3011-3024) NaH, −78° C., 1 hr, 52% (98% brsm); (c) TFA-CH$_2$—Cl$_2$ at 1:1, rt, 30 min, 99%; (d) (1) R$^2$CHO, AcOH, 4 Å MS, MeOH, rt, 1 hr, (2) NaCNBH$_3$, rt 16 hr, 72-84%; (e) R$^2$SO$_2$Cl, DIPEA, CH$_3$CN, 0° C.→rt, 16 hr, 82-93%; (f) R$^3$Br, Cs$_2$CO$_3$, DMF, rt, 16 hr, 79-82%.
Figure 8:
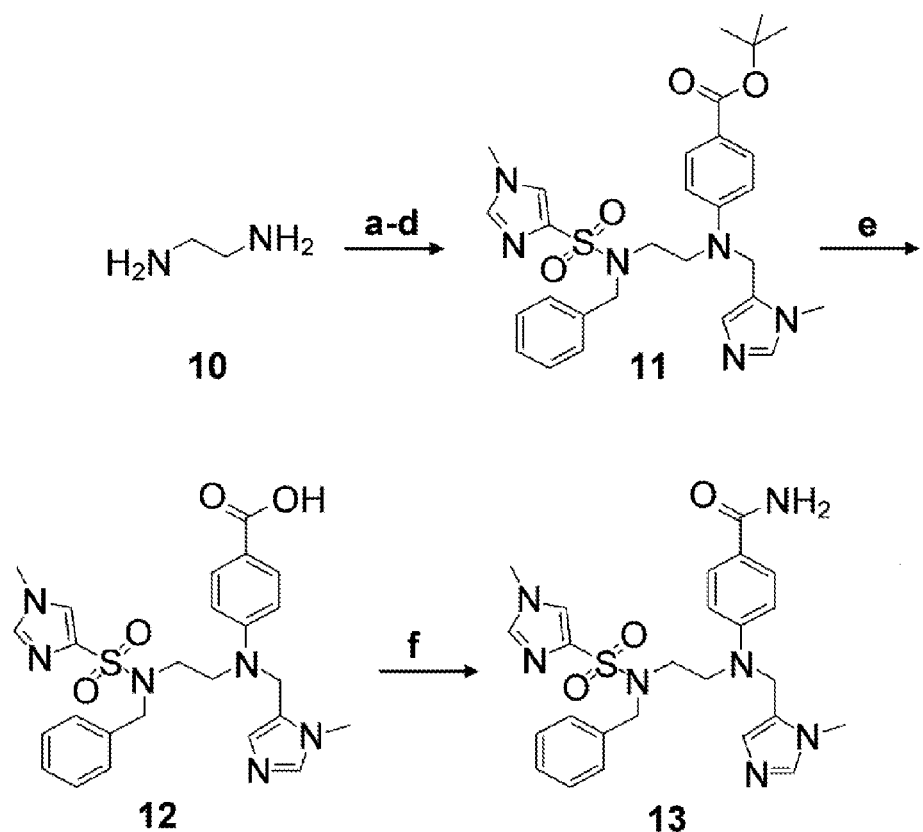
FIG. 8 is an illustration of reaction scheme 2 for the present invention. Reagents and conditions are: (a) tert-butyl-para-fluorobenzoate, DMSO, 120° C., 24 hr, 96%; (b) 1-methyl-1H-imidazole-4-sulfonyl chloride, DIPEA, CH$_3$CN, 0° C.→rt, 12 hr, 90%; (c) BnBr, Cs$_2$CO$_3$, DMF, rt, 16 hr, 92%; (d) (1) NaH, DMF, 0° C., 30 min, (2) 5-chloromethyl-1-methyl-1H-imidazole.HCl, (Qian, Y.; et al., Probing the hydrophobic pocket of farnesyltransferase: aromatic substitution of CAAX peptidomimetics leads to highly potent inhibitors. *Bioorg. Chem.* 1999, 7, 3011-3024) 0° C.→rt, 3 hr, 76%; (e) TFA-CH$_2$Cl$_2$ at 1:1, 3 hr, 96%; (f) NH$_4$Cl, HBTU, DIPEA, DMF, rt, 16 hr, 89%.
Figure 9:
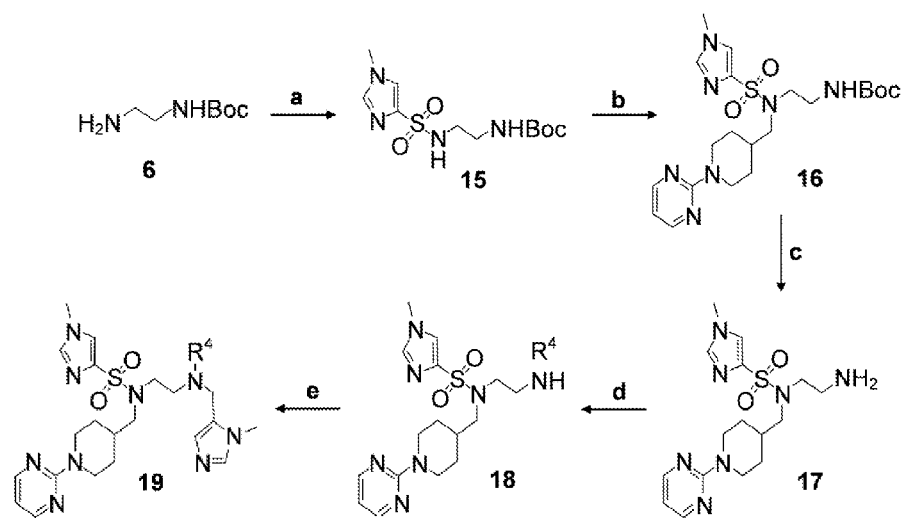
FIG. 9 is an illustration of reaction scheme 3 for the present invention. Reagents and conditions are: (a) 1-methyl-1H-imidazole-4-sulfonyl chloride, DIPEA, CH$_3$CN, 0° C.→rt, 16 hr, 95%; (b) 4-bromomethyl-N-(2-pyrimidinyl)-piperidine, Cs$_2$CO$_3$, DMF, rt, 4 days, 94%; (c) TFA-CH$_2$Cl$_3$-TIPS.H$_2$O at 47.5:47.5:2.5:2.5, rt, 1 hr, 100%; (d) R$^4$F, DIPEA, DMSO, 120° C., 24-48 hr, 48-97%; (e) (1) NaH, 0° C., 30 min, (2) 5-chloromethyl-1-methyl-1H-imidazole.HCl, (Qian, Y.; et al., Probing the hydrophobic pocket of farnesyltransferase: aromatic substitution of CAAX peptidomimetics leads to highly potent inhibitors. *Bioorg. Med. Chem.* 1999, 7, 3011-3024) 0° C.→rt, 2-3 hr, 63-96%.

"Piggyback" mammalian FTase inhibitors (FTIs) were prepared as described previously (Qian, et al., Probing the hydrophobic pocket of farnesyltransferase: aromatic substitution of CAAX peptidomimetics leads to highly potent inhibitors. *Bioorg. Med. Chem.* 1999, 7, 3011-3024), with new FTIs furnished by synthetic routes depicted in Schemes 1-3, seen in FIGS. 7-9 respectively. Inhibitors incorporating the para-benzonitrile moiety were accessed by the route in Scheme 1, seen in FIG. 7. Briefly, mono-N-Boc-ethylenediamine (6) was arylated with para-fluorobenzonitrile at 120° C. for 48 h in DMSO, affording secondary aniline 7. To arylate primary amines, a solution of primary amine was stirred and (1 equiv) in DMSO (0.2 M) added the aryl fluoride (1.2 equiv) and DIPEA (3 equiv). The reaction mixture was heated to 120° C. for 48 h. After allowing the reaction to cool, $H_2O$ was added, and the crude product was extracted with EtOAc (×3). The EtOAc extractions were combined, washed with water (×3), brine, dried ($Na_2SO_4$), filtered and concentrated. Installation of the imidazole was achieved by double deprotonation of 7 with LDA at −78° C. and subsequent chemoselective alkylation with 5-chloromethyl-1-methyl-1H-imidazole 3HCl, (Qian, Y.; et al., Probing the hydrophobic pocket of farnesyltransferase: aromatic substitution of CAAX peptidomimetics leads to highly potent inhibitors. *Bioorg. Med. Chem.* 1999, 7, 3011-3024) affording 8 in a moderate yield. After Boc deprotection, completion of the syntheses of FTase inhibitors 1 was conducted in one of two ways: either sulfonylation of 9, followed by alkylation of the resultant sulfonamide, or reductive amination of 9, and then sulfonylation of the resultant secondary amine. To alkylate the sulfonamides, a solution of the sulfonamide (1 equiv) had $Cs_2CO_3$ (2 equiv) in DMF (0.1 M) at 0° C. added the appropriate alkyl bromide or chloride (1.1 equiv). The resulting mixture was stirred at room temperature overnight. The reaction was diluted with water, then extracted into EtOAc (×3). The combined EtOAc extractions were washed with 5% $NaHCO_3$ (×3), brine, dried ($Na_2SO_4$), filtered and concentrated. For reductive amination of amines, a solution of 8 (1 equiv) in dry methanol (0.2 M) with 4 Å molecular sieves had an appropriate aldehyde (1.1 equiv) and acetic acid (1.3 eq) added. The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. Finally, purification of the FTIs was achieved by rpHPLC.

Initially, a focused set of PfFTase inhibitors were selected and analyzed their abilities to inhibit human FTase (hFTase), as well as GGTase-I, both in vitro and in whole cells, as seen in Table 1. The amino acid sequences of rat and human T1 FTase are 95% identical with complete sequence and structural conservation around the active site (Long, et al., The crystal structure of human protein farnesyltransferase reveals the basis for inhibition by CaaX tetrapeptides and their mimetics. *Proc. Natl. Acad. Sci. U.S.A.* 2001, 98, 12948-12953), so it is reasonable to analyze inhibition of hFTase with respect to docking studies in rFTase. Briefly, in vitro inhibition assays for hFTase and GGTase-I were carried out by measuring the incorporation of [$^3$H]FPP and [$^3$H]GGPP into recombinant H-Ras-CVLS and H-Ras-CVLL, respectively, as described previously (Vogt et al., Protein geranylgeranylation, not farnesylation, is required for G1 to S phase transition in mouse fibroblasts. *Oncogene*. 1996; 13:1991-1999). Whole cell inhibition of farnesylation and geranylgeranylation were determined based on the level of inhibition by synthetic compounds of H-Ras and Rap1A processing, respectively (Sun, et al., Both farnesyltransferase and geranylgeranyltransferase I inhibitors are required for inhibition of oncogenic K-Ras prenylation but each alone is sufficient to suppress human tumor growth in nude mouse xenografts. *Oncogene*. 1998; 16:1467-1473). In all cases, $IC_{50}$ data represents the average of three independent assays (n=3), unless otherwise stated, and errors are given as standard deviations.

TABLE 1

Enzyme Inhibition and Whole Cell Data of a Focused Set of Ethylenediamine-Based PfFTase Inhibitors

| compound | | | $IC_{50}$ (nM)[a] | | | processing $IC_{50}$ (μM)[c] | |
|---|---|---|---|---|---|---|---|
| no. | X | R[1] | hFTase | GGTase-1 | selectivity[b] | H-Ras | Rap1A |
| 3 (FTI-2581) | H | H | 6300 ± 360 | >10000 | 1.6 | >10 | >10 |
| 4 (FTI-2584) | Br | H | 730 ± 20 | 4400 | 6.0 | 5.7 ± 1.2 | >10 |
| 4 (FTI-2586) | Br | Me | 79 ± 30 | 530 ± 170 | 6.7 | 1.6 ± 1.3 | >10 |
| 4 (FTI-2585) | CN | Me | 56 ± 29 | 2700 ± 2200 | 48 | 1.9 ± 1.2 | >10 |

[a]$IC_{50}$ = inhibitor concentration required to achieve 50% inhibition of hFTase or GGTase-I in vitro.
[b]Ratio of GGTase-I to FTase IC50s.
[c]Processing $IC_{50}$ = inhibitor concentration required to achieve 50% inhibition of farnesylation of H-Ras or geranylgeranylation of Rap1A in whole cells.
In all cases, $IC_{50}$ data represents the average of three independent assays (n = 3), unless otherwise stated, and errors are given as standard deviations.

The importance of both the para-substitution of the aniline component and $N^\pi$-methylation (R1=Me) of the imidazole that was observed during the inhibition of PfFTase was reflected in the mammalian isoform of the enzyme. Unsubstituted aniline 3 exhibited little activity toward the inhibition of hFTase. Incorporation of bromine into the para position of the aniline ring, however, led to an order of magnitude increase in potency with in vitro $IC_{50}$'s for hFTase improving from 6300±360 nM for 3 to 730±20 nM for 4. Additionally, H-Ras processing $IC_{50}$s of FTIs were enhanced from >10 μM to 5.7±1.2 04. A further order of magnitude increase in FTase inhibition in vitro was achieved upon $N^\pi$-methylation of the imidazole, with 5 (FTI-2586) exhibiting an $IC_{50}$ of 79±30 nM, and an associated increase in whole cell activity (H-Ras processing $IC_{50}$=1.6±1.3 μM) was also observed. Even greater hFTase inhibitory activity was achieved by the replacement of bromine with cyano in the para position of the aniline ring (1a: $IC_{50}$=56±29 nM). It is interesting to note that a considerable improvement in selectivity for hFTase over GGTase-I was also observed; 1a was approximately 7-fold more selective for hFTase than was 5. In addition, the trends observed here in the inhibition of the mammalian isoform of FTase are mirrored by those observed in the disruption of the plasmodial isoform (Qian, Y.; et al., Probing the hydrophobic pocket of farnesyltransferase: aromatic substitution of CAAX peptidomimetics leads to highly potent inhibitors. *Bioorg. Med. Chem.* 1999, 7, 3011-3024). Given these very encouraging data, a SAR study of ethylenediamine-based inhibitors was conducted in order to optimize the inhibitory activity of 1a against hFTase.

Example

To perform sulfonyl $R^2$ SAR studies, $R^1$ was constrained as methyl and $R^3$ as benzyl, a series of eight $R^2$ sulfonyl groups were surveyed, seen in Table 2, all of which proved potent inhibitors of hFTase. The largest and most basic 5-dimethylamino-naphthalene-1-sulfonyl derivative 1 h was the least active inhibitor (hFTase $IC_{50}$=160±110 nM) of this series, with the most potent being the pyridine-2-sulfonyl compound 1f (hFTase $IC_{50}$=25±20 nM). Additionally, these inhibitors were more selective for hFTase over GGTase-I, with selectivities ranging from around 8-fold to greater than 333-fold. Many of these compounds also demonstrated very good whole cell activity, with pyridine-2-sulfonyl derivative if one of the most effective inhibitors (H-Ras processing $IC_{50}$=0.09±0.06 μM). Despite its potent in vitro inhibition of hFTase ($IC_{50}$=56±29 nM), 1-methyl-1H-imidazole-4-sulfonyl derivative 1a had the poorest H-Ras processing $IC_{50}$ (1.9±1.2 μM). This might be a consequence of the basicity of imidazole, and its protonation could hinder cellular entry. Regardless of this, the potent in vitro activity of 1a against hFTase, coupled with the fact that several inhibitors were functionalized with the 1-methyl-1H-imidazole-4-sulfonyl group developed from the PfFTase project, (Qian, Y.; et al., Probing the hydrophobic pocket of farnesyltransferase: aromatic substitution of CAAX peptidomimetics leads to highly potent inhibitors. *Bioorg. Med. Chem.* 1999, 7, 3011-3024) led us to retain this particular sulfonyl group as a baseline while varying other parts of the molecule. Selectivity of these FTIs for the hFTase isoform over the PfFTase isoform might then later be achieved by taking advantage of the previously mentioned three amino acid differences in the subpocket that is predicted to bind the para-benzonitrile ring.

TABLE 2

Enzyme Inhibition and Whole Cell Data of Ethylenediamine-Based FTIs Exhibiting a Range of $R^2$ Sulfonyl Groups[a]

| compound | | $IC_{50}$ (nM) | | | processing $IC_{50}$ (μM) | |
|---|---|---|---|---|---|---|
| no. | $R^2$ | hFTase | GGTase-1 | selectivity | H-Ras | Rap1A |
| 1a (FTI-2585) | (1-methylimidazol-4-yl) | 56 ± 29 | 2700 ± 2200 | 48 | 1.9 ± 1.2 | >10 |
| 1b (FTI-2640) | (n-propyl) | 48 ± 35 | 4100 ± 1700 | 85 | 0.07 | >10 |
| 1c (FTI-2644) | (cyclopropyl) | 85 ± 0.7 | 5500 ± 2700 | 65 | ND | ND |
| 1d (FTI-2592) | (phenyl) | 41 ± 26 | 310 ± 50 | 7.6 | 0.3 ± 0.1 | >10 |

TABLE 2-continued

Enzyme Inhibition and Whole Cell Data of Ethylenediamine-Based FTIs Exhibiting a Range of R² Sulfonyl Groups[a]

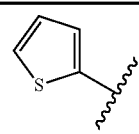

| compound | | IC$_{50}$ (nM) | | | processing IC$_{50}$ (μM) | |
|---|---|---|---|---|---|---|
| no. | R² | hFTase | GGTase-1 | selectivity | H-Ras | Rap1A |
| 1e (FTI-2589) | 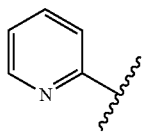 [SMILES: *c1ccccn1] | 50 ± 13 | 10,000 | 200 | 0.5 ± 0.2 | >10 |
| 1f (FTI-2587) | 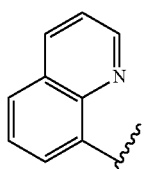 | 25 ± 20 | 820 ± 240 | 113 | 0.09 ± 0.06 | >10 |
| 1g (FTI-2590) | | 30 ± 14 | 10,000 | 333 | 0.6 ± 0.3 | >10 |
| 1h (FTI-2591) | 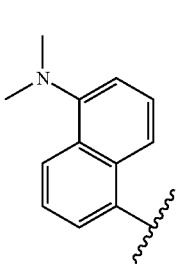 [SMILES: *c1cccc2c(N(C)C)cccc12] | 160 ± 110 | 10,000 | 63 | 0.5 ± 0.3 | >10 |

[a]ND = not determined

Example

To perform sulfonamide R³ SAR studies, R² was constrained as 1-methyl-1H-imidazole-4-sulfonyl, and the R³ group investigated with a broad series of derivatives, which included previously reported (Qian, et al., Probing the hydrophobic pocket of farnesyltransferase: aromatic substitution of CAAX peptidomimetics leads to highly potent inhibitors. *Bioorg. Med. Chem.* 1999, 7, 3011-3024) and novel inhibitors, seen in Table 3. Replacement of T3 benzyl in the parent inhibitor 1a with a propargyl group (1aa) led to a reduction in both in vitro activity (IC$_{50}$=720±200 nM, cf. 56±29 nM) and whole cell activity, as well as in GGTase-I/FTase selectivity. However, the unsubstituted allyl derivative (1ab) was tolerated in vitro (IC$_{50}$=54±30 nM), although not in whole cells (H-Ras processing IC$_{50}$>10 μM).

TABLE 3

Enzyme Inhibition and Whole Cell Data of Ethylenediamine-Based FTIs Exhibiting a Range of R³ Sulfonamides

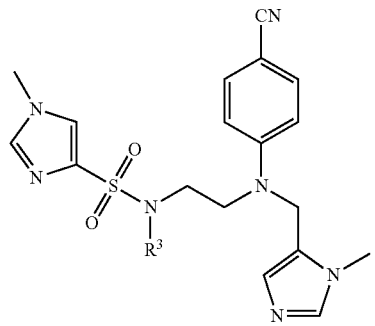

| compound | | IC₅₀ (nM) | | | processing IC₅₀ (μM) | |
|---|---|---|---|---|---|---|
| no. | R² | hFTase | GGTase-1 | selectivity | H-Ras | Rap1A |
| 1aa (FTI-2630) | propargyl | 720 ± 200 | >10,000 | >14 | 6 (n = 2) | >10 |
| 1ab (FTI-2600) | allyl | 54 ± 30 | >10,000 | >14 | >10 | >10 |
| 1ac (FTI-2606) | methallyl | 114 ± 80 | 600 ± 300 | 5.3 | >10 | >10 |
| 1ad (FTI-2611) | 2-bromoallyl | 180 ± 100 | 5500 ± 1900 | 31 | 5.7 ± 1.5 | >10 |
| 1ae (FTI-2607) | tBuNHC(O)CH₂ | 1400 ± 900 | >10,000 | 7.1 | >10 | >10 |
| 1a (FTI-2585) | benzyl | 56 ± 29 | 2700 ± 2200 | 48 | 1.9 ± 1.2 | >10 |
| 1af (FTI-2601) | 4-pyridylmethyl | 72 ± 20 | >10,000 | >139 | >10 | >10 |
| 1ag (FTI-2602) | 2-(pyrrol-1-yl)ethyl | 30 ± 33 | 510 ± 270 | 17 | 4.3 ± 1.5 | >10 |
| 1ah (FTI-2635) | 3-furylmethyl | 320 ± 190 | 6100 ± 1600 | 19 | 0.65 (n = 2) | >10 |
| 1ai (FTI-2636) | 3-thienylmethyl | 67 ± 38 | 940 ± 20 | 14 | 0.4 (n = 2) | >10 |

TABLE 3-continued

Enzyme Inhibition and Whole Cell Data of Ethylenediamine-Based FTIs Exhibiting a Range of R³ Sulfonamides

| compound | | IC$_{50}$ (nM) | | | processing IC$_{50}$ (μM) | |
|---|---|---|---|---|---|---|
| no. | R² | hFTase | GGTase-1 | selectivity | H-Ras | Rap1A |
| 1aj (FTI-2638) | furan-CH₂ | 870 ± 120 | 13,400 (n = 2) | 15 | 0.8 (n = 2) | >10 |
| 1ak (FTI-2639) | thiophene-CH₂ | 2300 ± 1500 | 5900 ± 3000 | 2.6 | 0.4 (n = 2) | >10 |
| 1al (FTI-2633) | 3,5-dimethylisoxazole-CH₂ | 510 ± 460 | 1360 ± 740 | 2.7 | >10 | >10 |
| 1am (FTI-2637) | 2,4-dimethylthiazole-CH₂ | 6200 ± 920 | >10,000 | >1.6 | >10 | >10 |
| 1an (FTI-2642) | 1,5-dimethylpyrazole-CH₂ | 5300 ± 1700 | >10,000 | >1.9 | ND | ND |
| 1ao (FTI-2614) | 2-methylbenzyl | 51 ± 26 | 780 ± 320 | 15 | 1 ± 0 | >10 |
| 1ap (FTI-2615) | 3-methylbenzyl | 54 ± 30 | 630 ± 240 | 12 | 0.3 ± 0.2 | >10 |
| 1aq (FTI-2623) | 4-methylbenzyl | 370 ± 210 | 580 ± 200 | 1.6 | 2 ± 1 | >10 |

TABLE 3-continued

Enzyme Inhibition and Whole Cell Data of Ethylenediamine-Based FTIs Exhibiting a Range of R³ Sulfonamides

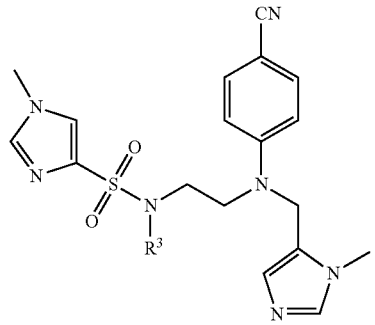

| compound | | IC₅₀ (nM) | | | processing IC₅₀ (μM) | |
|---|---|---|---|---|---|---|
| no. | R² | hFTase | GGTase-1 | selectivity | H-Ras | Rap1A |
| 1ar (FTI-2624) | 3-CN-benzyl | 78 ± 12 | ND | — | 5 ± 3 | >10 |
| 1as (FTI-2625) | 4-CN-benzyl | 370 ± 370 | 6500 ± 2900 | 18 | >10 | >10 |
| 1at (FTI-2610) | 3-biphenyl-CH₂ | 230 ± 150 | 550 ± 120 | 2.4 | 3 ± 0 | >10 |
| 1au (FTI-2612) | 4-biphenyl-CH₂ | 1700 ± 900 | 7300 ± 2200 | 4.3 | 5 ± 1 | >10 |
| 1av (FTI-2615) | 4-(pyrrol-1-yl)benzyl | 390 ± 100 | 5800 ± 3500 | 15 | 4 ± 1 | >10 |
| 1aw (FTI-2631) | cyclopropylmethyl | 590 ± 300 | >10,000 | >17 | >10 | >10 |
| 1ax (FTI-2602) | cyclohexylmethyl | 60 ± 10 | 530 ± 120 | 8.8 | 0.1 ± 0.07 | >10 |

TABLE 3-continued

Enzyme Inhibition and Whole Cell Data of Ethylenediamine-Based FTIs Exhibiting a Range of $R^3$ Sulfonamides

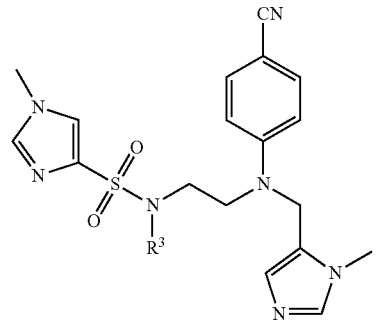

| compound | | IC$_{50}$ (nM) | | | processing IC$_{50}$ (μM) | |
|---|---|---|---|---|---|---|
| no. | $R^2$ | hFTase | GGTase-1 | selectivity | H-Ras | Rap1A |
| 1ay (FTI-2670) | *tert*-butyl piperidine-4-ylmethyl carbamate | 3700 ± 790 | >10,000 | >2.7 | >2 | >2 |
| 1az (FTI-2722) | 2-(pyrimidin-2-yl)piperidin-4-ylmethyl | 510 ± 62 | >10,000 | >20 | >10 | >10 |

Substitution of the allyl moiety with a methyl group at position-2 (1ac) led to a reduction in hFTase in vitro activity and, at the same time, led to improved inhibition of GGTase-I, resulting in a reduced GGTase-I/FTase selectivity of about 5-fold. Again, whole cell activity was poor but this was recovered somewhat by replacement of the methyl in 1ac with a bromine atom, giving an H-Ras processing IC$_{50}$ of 5.7±1.5 μM for inhibitor 1ad. Extension of this sp$^2$-hybridized series to the bulky tert-butylacetamido derivative 1ae was not tolerated, neither in vitro nor in whole cells. Incorporation of nitrogen into the para position of benzyl to give pyridine derivative 1af maintained activity in vitro (IC$_{50}$=72±20 nM), although it showed little activity in whole cells. Nonetheless, 1af exhibited substantially improved selectivity toward hFTase, with a GGTase-I/FTase selectivity of >139-fold.

A focused set of five-membered heteroaromatics 1ag-1an were examined. Pyrrole 1ag was around twice as active as the parent inhibitor 1a, disrupting hFTase with an IC$_{50}$ value of 30±33 nM. Conversely, the series of furans and thiophenes typically proved much poorer inhibitors and FTase inhibitory activity was found to be sensitive to heteroatom position. Furan 1ah was more than twice as potent as isomeric 1aj, and thiophene 1ai was more than 34 times as potent as isomeric 1ak and approximately as active as 1a. Despite these moderate to poor in vitro data for hFTase (except for 1ai) all members of this series exhibited reasonable H-Ras processing whole cell data and in all cases the IC$_{50}$ values were more potent than 1a. The remaining heteroaromatics (1al-1an) containing two heteroatoms were poor inhibitors of hFTase.

Introduction of a methyl group on the benzyl ring of 1a was tolerated in the ortho (1ao) and meta (1ap) positions (in vitro hFTase IC$_{50}$s of 51±26 nM and 54±30 nM, respectively) but not in the para (1aq) position (IC$_{50}$=370±210 nM). A similar trend was observed in whole cell activity, with meta-derivative 1ap the most potent (H-Ras processing IC$_{50}$=0.3±0.2 μM). The members of this series demonstrated GTase-I IC$_{50}$ values between 580 and 780 nM, considerably reducing the FTase/GGTase-I selectivities relative to that of the parent benzyl inhibitor 1a. The greater potency of meta-substituted benzyl groups over their para counterparts was also observed for the cyano derivatives 1ar and 1as and for the phenyl derivatives 1at and 1au, a finding that was reflected in their corresponding H-Ras processing whole cell activities. Additionally, the same trend was noticed in the in vitro data of GGTase-I inhibition. The poor in vitro inhibition of hFTase by para-phenyl derivative 1au (IC$_{50}$=1700±900 nM) was recovered somewhat by replacement of the terminal phenyl group with the smaller pyrrole heterocycle (1av; IC$_{50}$=390±210 nM), which was also reflected in the whole cell assays (IC$_{50}$=5±1 μM (1au) vs 4±1 μM (1av)).

The small cyclopropylmethyl derivative 1aw was less active than the parent benzyl inhibitor 1a, but the larger cyclohexylmethyl derivative 1ax, a closer match to benzyl, proved a potent inhibitor in vitro (hFTase IC$_{50}$=60±10 nM) and was one of the most potent inhibitors in whole cells (H-Ras processing IC$_{50}$=0.1±0.07 μM)). However, inhibitor 1ax was also quite active toward GGTase-I (IC$_{50}$=530±120 nM), giving a much-reduced hFTase/GGTase-I selectivity of about 9-fold. The binding pocket that was predicted to bind the $R^3$ group was probed deeper by modifying the cyclohexylmethyl substituent to a 4-piperidinylmethyl group; the piperidine nitrogen provided a handle from which to achieve further functionalization. Accordingly, N-Boc-piperidin-4-ylmethyl derivative 1ay and N-(2-pyrimidinyl)-4-ylmethyl derivative 1az were synthesized. Introduction of the N-Boc group at the 4 position of the cyclohexyl group (1ay) caused more than a 60-fold drop in hFTase inhibition relative to 1ax. Activity was recovered by more than 7-fold through replacement of the bulky tert-butoxycarbonyl group with the planar 2-pyrimidinyl group (1az: $IC_{50}$=510±62 nM; cf. 1ay: $IC_{50}$=3700±790 nM) although both piperidinylmethyl derivatives exhibited poor whole cell activities.

Example

For aniline $R^4$ SAR studies, the para-position (X) was substituted. At the deepest point of the predominantly hydrophobic pocket of rFTase in which GOLD docking studies consistently predicted the para-benzonitrile moiety (the aniline "$R^4$ group") of the inhibitors would bind, there is a hydrophilic domain formed by N165α, Y166α, and H201α. To probe this site further, the cyano group (X) of the para-benzonitrile moiety was replaced with alternative polar groups, such as a carboxylic acid or a carboxamide, in the anticipation that such groups might be able to participate in additional hydrogen-bonding interactions and so furnish more potent hFTase inhibitors. Nonpolar substituents were also investigated in the para position, such as Br, Ph and $CO_2$t-Bu, which, provided the aniline group binds as predicted, would be expected to inhibit hFTase less well. Accordingly, para-(tert-butyl ester) derivative 11 was prepared in a similar manner to the synthetic route in Scheme 1 but employing tert-butyl para-fluorobenzoate in place of para-fluorobenzonitrile, seen in Example 1. Treatment of 11 with TFA furnished the para-carboxylic acid 12, which was then converted to para-carboxamide 13 using HBTU and ammonium chloride. para-Phenylderivative 14 was prepared from the previously reported intermediate 1-tert-butoxycarbonylamino-2-[biphenyl-4-yl-(3-methyl-3H-imidazol-4-ylmethyl)amino]-ethane, listed as compound 9a in Qian, Y.; et al., Probing the hydrophobic pocket of farnesyltransferase: aromatic substitution of CAAX peptidomimetics leads to highly potent inhibitors. Bioorg. Med. Chem. 1999, 7, 3011-3024; see Example 1 and the protocols for specific compounds for full details). As illustrated in Table 4, all replacements for the cyano group afforded compounds that provided less inhibition of hFTase in vitro. Interestingly, FTIs with bulky X groups (11: X=$CO_2$t-Bu; 14: X=Ph) exhibited a reversed selectivity for GGTase-I over hFTase, suggesting the aniline-binding domain may be larger in GGTase-I than in hFTase.

TABLE 4

Enzyme Inhibition and Whole Cell Data of Ethylenediamine-Based FTIs Exhibiting a Range of para-Substituted Anilines

| compound no. | X | $IC_{50}$ (μM) hFTase | $IC_{50}$ (μM) GGTase-1 | selectivity | processing $IC_{50}$ (μM) H-Ras | processing $IC_{50}$ (μM) Rap1A |
|---|---|---|---|---|---|---|
| 4 (FTI-2586) | Br | 79 ± 30 | 530 ± 170 | 6.7 | 1.6 ± 1.3 | >10 |
| 1a (FTI-2585) | CN | 56 ± 29 | 2700 ± 2200 | 48 | 1.9 ± 1.2 | >10 |
| 11 (FTI-2720) | $CO_2$tBu | 5400 (n = 2) | 4900 (n = 2) | 0.9 | ND | ND |
| 12 (FTI-2721) | COOH | >10000 | >10000 | 48 | ND | ND |
| 13 (FTI-2728) | $CONH_2$ | 5300 (n = 2) | >10000 | >2 | ND | ND |
| 14 (FTI-2527) | Ph | 6850 (n = 2) | 5000 ± 2600 | 0.7 | ND | ND |

Example

Figure 10:
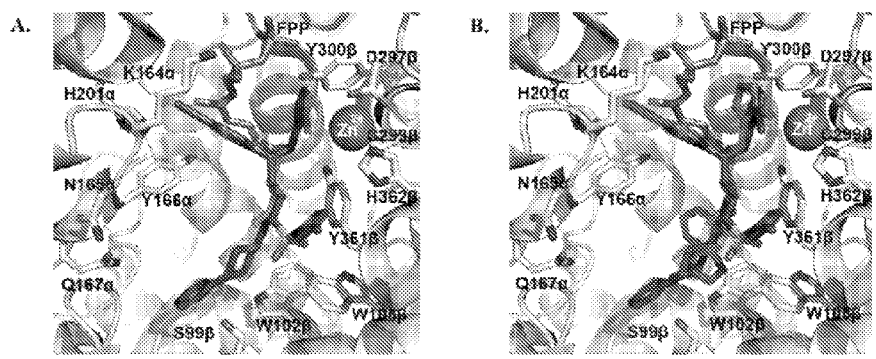
FIGS. 10(A) and (B) are overlays of the inhibitor structures showing high scoring rFTase active site conformation of (A) inhibitor 1az, dark grey molecule in center of image by atom type) as identified by flexible ligand GOLD$^{32}$ docking experiments and (B) overlaid with the high scoring active site conformation of inhibitor 1a that was presented in FIG. 1B.

To perform aniline $R^4$ SAR studies, the aromatic ring was further analyzed using GOLD docking. The GOLD docking studies suggested that two of the polar amino acids within the para-benzonitrile-binding pocket might influence binding of the aniline ring itself. Specifically, Y166α could make contact with hydrogen bonding acceptor or donor groups in the ortho and meta positions of the aniline to improve inhibitor binding in mammalian FTase, and likewise, H201α can be exploited with an appropriate group in the meta position. Accordingly, a series of FTase inhibitors was prepared in which the para-benzonitrile portion was modified to attempt to target these two amino acids; the synthetic route that was pursued is shown in Scheme 3, seen in FIG. 8. Compound 1ax bearing the N-(2-pyrimidinyl)-piperidin-4-ylmethyl $R^3$ group was selected as the baseline, anticipating that its moderate activity would better highlight the effects of modifying the para-benzonitrile component. Again, with the only constraint being that the nonmethylated τ-nitrogen of the N-methylimidazolylmethyl group should bind the active site $Zn^{2+}$ ion, several GOLD docking experiments of compound 1az were performed. While the $R^3$=N-(2-pyrimidinyl)-piperidin-4-ylmethyl and the 1-methyl-1H-imidazole-4-sulfonyl groups in 1az bound differently to the corresponding groups in 1a, the $R^4$=para-benzonitrile group under investigation bound in the same subpocket (tetra-methylene side chain of K164α and side chain of Y166α) as the corresponding motif in 1a in four out of the five highest scoring (lowest energy) docking solutions, such as for example FIG. 10A. Furthermore, in most of those cases, the para-benzonitrile moieties in each inhibitor overlaid excellently, as illustrated in FIG. 10B.

Briefly, mono-N-Boc-ethylenediamine (6) was sulfonylated with 1-methyl-1H-imidazole-4-sulfonyl chloride to give 15 in 95% yield. Chemoselective alkylation of the more acidic and less hindered sulfonamide NH was then readily accomplished by treatment of 15 with N-(2-pyrimidinyl)-piperidin-4-ylmethyl bromide in the presence of cesium carbonate in DMF. After TFA-mediated Boc deprotection of 16, arylation of the resultant primary amine was achieved by heating 17 at 120° C. in DMSO with a series of aryl fluorides, giving the secondary anilines 18 in a range of yields from 48 to 97%. Finally, these secondary anilines were then smoothly alkylated in good to excellent yields by deprotonation with NaH in DMF. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% $NaHCO_3$ (×3), brine, dried ($Na_2SO_4$), filtered and concentrated. This was followed by reaction with 5-chloro-methyl-1-methyl-1H-imidazole 3HCl (Qian, Y.; et al., Probing the hydrophobic pocket of farnesyltransferase: aromatic substitution of CAAX peptidomimetics leads to highly potent inhibitors. *Bioorg. Med. Chem.* 1999, 7, 3011-3024) to furnish the FTase inhibitors 19a-19h, seen in Table 5.

TABLE 5

Enzyme Inhibition and Whole Cell Data of Ethylenediamine-Based FTIs Exhibiting a Range of $R^4$ Anilines

| compound no. | $R^4$ | $IC_{50}$ (μM) hFTase | GGTase-1 | selectivity |
|---|---|---|---|---|
| 1az (FTI-2722) | CN-phenyl | 510 ± 62 | >10000 | >20 |
| 19a (FTI-2718) | CN-chlorophenyl | 550 ± 110 | >10000 | >18 |
| 19b (FTI-2733) | CN-pyridyl | 520 ± 320 | >10000 | >19 |

TABLE 5-continued
Enzyme Inhibition and Whole Cell Data of Ethylenediamine-Based FTIs Exhibiting a Range of R⁴ Anilines
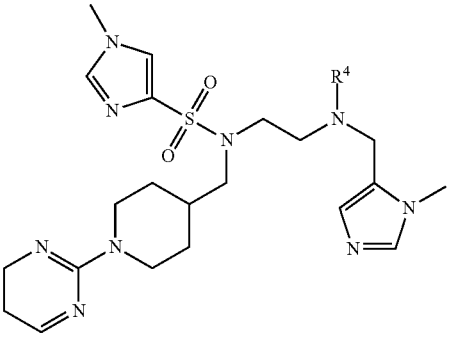
| compound | | IC$_{50}$ (μM) | | |
|---|---|---|---|---|
| no. | R⁴ | hFTase | GGTase-1 | selectivity |
| 19c (FTI-2707) | 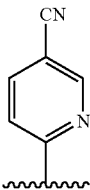 | 110 ± 26 | >10000 | >91 |
| 19d (FTI-2709) | 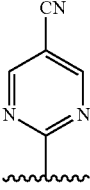 [SMILES: *c1ncc(C#N)cn1] | 620 ± 100 | >10000 | >16 |
| 19e (FTI-2712) | 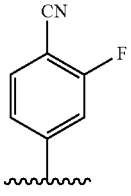 [SMILES: *c1ccc(C#N)c(F)c1] | 230 ± 110 | 9400 (n = 2) | 41 |
| 19f (FTI-2713) | 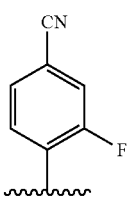 [SMILES: *c1ccc(C#N)cc1F] | 64 ± 8.6 | >10000 | >156 |

TABLE 5-continued

Enzyme Inhibition and Whole Cell Data of Ethylenediamine-Based FTIs Exhibiting a Range of $R^4$ Anilines

| compound | | IC$_{50}$ (µM) | | |
|---|---|---|---|---|
| no. | $R^4$ | hFTase | GGTase-1 | selectivity |
| 19g (FTI-2715) | CN, 3,5-difluorophenyl | 290 ± 180 | >10000 | >34 |
| 19h (FTI-2719) | CN, tetrafluorophenyl | 490 ± 70 | 8750 ± 750 | 18 |

Positioning a chlorine (19a) at the ortho position had little effect relative to the parent compound 1az on the inhibition of hFTase. Conversely, replacement of an ortho-CH unit with nitrogen to give pyridine 19c conferred an approximate 4-fold improvement in hFTase enzymatic inhibitory activity (19c 110±26 nM vs 1az 510±320 nM), while meta-substituted pyridine 19b offered no enhancement in activity, suggesting an important role for a hydrogen-bonding acceptor group in the ortho position. However, incorporation of nitrogens at both ortho positions, as in pyrimidine 19d, caused a reduction in the IC$_{50}$ value back to approximately the same as that exhibited by the parent compound 1az. Inhibitor 19e with a fluorine at one of the meta positions was around twice as potent as 1az, while a fluorine at the ortho position led to an especially potent inhibitor (19f) with an hFTase IC$_{50}$ of 64±8.6 nM, approximately 8-fold as active as 1az and twice as potent as the ortho-pyridine 19c. Introduction of a second fluorine atom at the other ortho position (inhibitor 19g) caused a reduction in inhibition potency relative to the singly ortho-substituted inhibitor 19f, as was observed with the pyridine derivatives 19c and 19d (pyrimidine), respectively. Replacement of all four ring hydrogens in 19h offered no benefit to hFTase inhibition, relative to parent 1az. Finally, it is noteworthy that all derivatives based on the parent compound 1az generally exhibited very good to excellent selectivity for inhibition of hFTase over GGTase-I, particularly for ortho-pyridine 19c and ortho-fluoride 19f.

Example

The ethylenediamine scaffold was then analyzed for optimization using a variety of alternative diamino-based scaffolds, whose structures are depicted in Table 6 and whose syntheses have been described elsewhere (Vasudevan, A.; Qian, Y.; Vogt, A.; Blaskovich, M. A., Ohkanda, J.; Sebti, S. M.; Hamilton, A. D. Potent, highly selective, and non-thiol inhibitors of protein geranylgeranyltransferase-I. *J. Med. Chem.* 1999, 42, 1333-1340; (b) Sun, J.; Blaskovich, M. A.; Knowles, D.; Qian, Y.; Ohkanda, J.; Bailey, R. D.; Hamilton, A. D.; Sebti, S. M. Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. *Cancer Res.* 1999, 59, 4919-4926; (c) Ohkanda, J.; Lockman, J. W.; Kothare, M. A.; Qian, Y.; Blaskovich, M. A.; Sebti, S. M.; Hamilton, A. D. Design and synthesis of potent nonpeptidic farnesyltransferase inhibitors based on a terphenyl scaffold. *J. Med. Chem.* 2002, 45, 177-188). 1,3-Diaminopropane-based inhibitor 20a has increased conformational flexibility relative to the corresponding ethylenediamine-based inhibitor 1a. The data in Table 6 suggest that increasing the flexibility in this way caused more than a 7-fold drop in hFTase inhibitory activity. Likewise, reducing the conformational flexibility of the scaffold with the 1,2- and 1,3-diaminocyclopentyl derivatives 20b-20e also led to a decrease in hFTase inhibitor potency, with the cis-configurations exhibiting half the potencies of their trans-counterparts. Similar trends were observed in PfFTase.[30] Of all the different scaffolds examined, the ethylenediamine unit was found to be optimal at delivering the four substituents into the proposed subpockets as well as furnishing the greatest hFTase/GGTase-I selectivity.

TABLE 6

Enzyme Inhibition Data of FTIs Exhibiting a Range of Ethylenediamine-Analogue Scaffolds

| compound no. | X | IC$_{50}$ ($\mu$M) hFTase | GGTase-1 | selectivity |
|---|---|---|---|---|
| 1a | (propylene linker) | 56 ± 29 | 2700 ± 2200 | 48 |
| 20a | (butylene linker) | 420 ± 210 | 4600 (n = 2) | 11 |
| 20b | (cyclopentyl, cis) ± | 1000 ± 350 | >10000 | >10 |
| 20c | (cyclopentyl, trans) ± | 450 ± 70 | 9150 (n = 2) | 20 |

TABLE 6-continued

Enzyme Inhibition Data of FTIs Exhibiting a Range of Ethylenediamine-Analogue Scaffolds

| compound no. | X | IC$_{50}$ ($\mu$M) hFTase | GGTase-1 | selectivity |
|---|---|---|---|---|
| 20d | (cyclopentyl, cis) ± | 650 ± 220 | >10000 | >15 |
| 20e | (cyclopentyl, trans) ± | 380 ± 100 | 7050 (n = 2) | 19 |

Example

Three ethylenediamine-based inhibitors incorporating optimized $R^1$, $R^2$, $R^3$, $R^4$ were designed, and X substituents that were identified from SAR studies, as illustrated by compounds 21a-21c in Table 7. Primary data considered in the selection of moieties that were believed to furnish optimized inhibitors were in vitro FTase inhibition, whole cell H-Ras processing data, and to a lesser extent, GGTase-I/hFTase selectivity. The $R^1$ group selected was methyl, seen in Table 1, $R^2$ was 2-pyridinesulfonyl, seen in Table 2, $R^3$ was cyclohexylmethyl, seen in Table 3, $R^4$ was para-benzonitrile, seen in Table 4, substituted at the ortho position, seen in Table 5, and the core scaffold incorporated was the simple ethylenediamine unit, seen in Table 6, leading to inhibitors 21a, 21b, and 21c in Table 7. As a comparison, three of the most potent "unoptimized" FTIs were also included in Table 7: 1a, 1ax, and 1f. The trend observed in Table 5 upon varying the ortho-CH unit to CF and to N was reproduced with these optimized inhibitors, however none of compounds 21a-21c exhibited improved activity over the leads 1a, 1ax, and 1f, possibly due to the adoption of different binding geometries. Much reduced selectivities for hFTase over GGTase-I were also observed. Nonetheless, 21b was equipotent with 1ax in whole cells, whereby both inhibitors disrupted H-Ras processing with IC$_{50}$ values of about 90 nM.

TABLE 7

Enzyme Inhibition and Whole Cell Data of Optimized, Ethylenediamine-Based FTIs

[Core structure: R²S(O)₂N(R³)-CH₂CH₂-N(R⁴)-CH₂-(1-methylimidazol-5-yl)]

| compound | | | | IC₅₀ (μM) | | | Processing IC₅₀ (μM) | |
|---|---|---|---|---|---|---|---|---|
| no. | R² | R³ | R⁴ | hFTase | GGTase-1 | Selec. | H-Ras | Rap1A |
| 1a (FTI-2585) | 1-methylimidazol-4-yl | benzyl | 4-cyanophenyl | 56 ± 29 | 2700 ± 2200 | 48 | 1.9 ± 1.2 | >10 |
| 1ax (FTI-2602) | 1-methylimidazol-4-yl | cyclohexylmethyl | 4-cyanophenyl | 60 ± 10 | 530 ± 120 | 8.8 | 0.1 ± 0.07 | >10 |
| 1f (FTI-2587) | pyridin-2-yl | benzyl | 4-cyanophenyl | 25 ± 20 | 820 ± 240 | 33 | 0.09 ± 0.06 | >10 |
| 21a (FTI-2736) | pyridin-2-yl | cyclohexylmethyl | 4-cyanophenyl | 400 ± 160 | 610 ± 160 | 1.5 | 0.268 ± 0.212 | 6.2 ± 1.2 |
| 21b (FTI-2734) | pyridin-2-yl | cyclohexylmethyl | 4-cyano-2-fluorophenyl | 250 ± 190 | 520 ± 90 | 2.1 | 0.0887 ± 0.0258 | 2.7 ± 1.5 |
| 21c (FTI-2735) | pyridin-2-yl | cyclohexylmethyl | 5-cyanopyridin-2-yl | 350 ± 170 | 690 ± 92 | 2 | 0.288 ± 0.251 | 19 |

Figure 11:
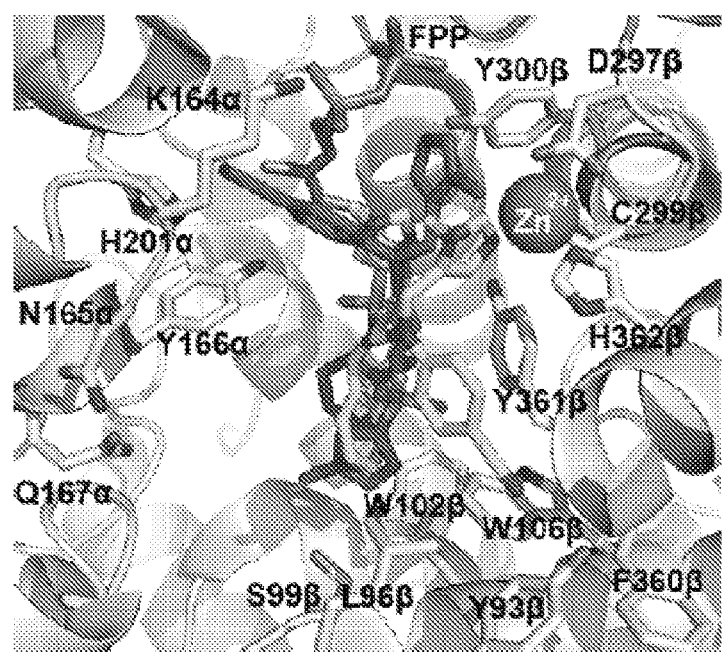
FIG. 11 is an overlay of the crystal structure of 1a, seen as a light grey molecule; PDB ID: 3E3239) with a high scoring (low energy) GOLD docked pose of 1a, dark grey molecule, in the active site of rFTase.

FIG. 11 shows the crystal structure of 1a, seen as a light grey molecule in the center of the image; taken from FIG. 5A, overlaid with the flexible ligand GOLD docking of 1a, seen as a dark grey molecule in the center of the image; taken from FIG. 2. More basic imidazole 3-methyl-3H-imidazol-4-ylmethyl were found to bind the zinc ion (which was the only constraint implemented in the GOLD docking experiments), and GOLD subsequently correctly placed the benzyl moiety of 1a in the subpocket formed by W102β, W106β, and Y361β. However, as FIG. 11 illustrates, the para-benzonitrile and the sulfonylimidazole substituents were found to bind in different manners to those predicted. Specifically, the para-benzonitrile moiety was predicted to bind in the subpocket created by K164α, N165α, H201α, Y166α, but was actually found engaged in a weak π-π interaction with Y361β in the product exit groove, F360β, Y93β, L96β, W106β, while the sulfonylimidazole group was predicted to bind the Arg202β, yet was found stacked between Zn-binding imidazole and the first isoprene of FPP.

Despite the GOLD prediction of a very different binding mode for the para-benzonitrile moiety, several potent inhibitors, such as compound 19f seen in Table 5, were serendipitously identified as a consequence of the para-benzonitrile making alternative but still significant contacts. The observed π-π stacking of the para-benzonitrile moiety against the Y361β residue suggests an explanation for the observed in vitro SAR data for the modifications made to the para-benzonitrile ring of 1a, seen in Tables 1 and 4, and 1az, seen in Table 5. π-π Stacking interactions are known to be energetically more favorable between an electron-rich arene, here Y361β, and an electron-poor arene, here the para-benzonitrile of inhibitor 1a. For the series of inhibitors in Table 4, substitution of the para position of the aniline with a strongly electron-withdrawing cyano group led to the most potent inhibitor (1a) while eliminating all substitution from the aniline ring of 1a and with $R^1$=H essentially abolished activity, as seen in compound 2 seen in Table 1. Additionally, the product exit groove where the para-benzonitrile binds is of limited size and mostly hydrophobic, suggesting that substituents larger than the linear cyano unit, such as the bulky tert-butyl ester in 11 or the phenyl ring in 14, and more polar than the cyano group, such as the acid in 12 and the carboxamide in 13, would be poorly tolerated. This was confirmed experimentally, seen in Table 4. For the series of inhibitors in Table 5, replacement of the ortho (with respect to the aniline nitrogen) CH (1az) with either N (19c) or CF (19l) led to an approximate 5-fold or 8-fold improvement in inhibitor activity, respectively. This may be due to the introduced electron-withdrawing groups that render the aniline even more electron-poor, thereby enhancing its interaction with Y361β. On the other hand, replacement of the meta-CH (1az) with N (19b) resulted in no improvement in activity, while substitution of the meta-CH with a CF group (19e) led to only a 2-fold increase in inhibitor potency, as opposed to the 8-fold enhancement achieved by ortho-fluoride 19f. Without being bound to any specific theory, the crystal structure of 1a suggests that the incorporation of electronegative groups in the meta position might be poorly tolerated due to a clash with the anionic side chain of D359β, explaining the reduced enhancement in potency of inhibitors 19b and 19e as a means of avoiding this unfavorable interaction, 180° rotation about the N—C aniline bond would direct the introduced N or CF group into a hydrophobic domain comprising L96β and W106β and would therefore also be unfavorable. Replacement of both ortho-CH groups with either two nitrogens (19d) or two CF groups (19g) was not tolerated relative to the mono-ortho-substituted inhibitors (19b and 19e, respectively). This observation may be a consequence of one of the electronegative groups being forced into the hydrophobic L96β/W106β region in order that the energetically favorable π-π (stacking between the aniline ring of the inhibitor and Y361β is maintained.

Generally, there was little variation in activity among the $R^2$ sulfonyl derivatives shown in Table 2, which may be a consequence of this moiety exhibiting insignificant interactions with the protein itself, being found stacked between the zinc-binding imidazole and FPP. However, there were clear trends in the hFTase inhibition data for the $R^3$ series of sulfonamide analogues, seen in Table 3. The crystal structure of 1a illustrates that the $R^3$ phenyl ring can access the $a_2$ residue binding site (W106β/W102β/L96β) of the $C_{ala2}X$ substrate. For the most part, small, hydrophobic $R^3$ groups afforded potent hFTase inhibitors, likely due to the $R^3$ group making van der Waals contacts with W106β, W102β, and/or L96β. Within a particular series of $R^3$ substituent, for example the ortho-, meta-, and para-tolyl derivatives 1ao, 1ap, and 1aq, respectively, ortho- and meta-functionalized compounds were tolerated, whereas para-functionalization was not. This may be a consequence of the para derivative being too large to access the $a_2$ residue binding site. Indeed, the crystal structure of 1ay shows that the large N-Boc-piperidin-4-ylmethyl group traverses, rather than binds in, the $a_2$ residue binding site and instead reaches into the X residue binding site. The relative selectivities of the ethylenediamine-based inhibitors was previously reported for the *Plasmodium* isoform of FTase over the mammalian isoform (Qian, Y.; et al., Probing the hydrophobic pocket of farnesyltransferase: aromatic substitution of CAAX peptidomimetics leads to highly potent inhibitors. *Bioorg. Med. Chem.* 1999, 7, 3011-3024; Vasudevan, A.; Qian, Y.; Vogt, A.; Blaskovich, M. A., Ohkanda, J.; Sebti, S. M.; Hamilton, A. D. Potent, highly selective, and non-thiol inhibitors of protein geranylgeranyltransferase-I. *J. Med. Chem.* 1999, 42, 1333-1340; (b) Sun, J.; Blaskovich, M. A.; Knowles, D.; Qian, Y.; Ohkanda, J.; Bailey, R. D.; Hamilton, A. D.; Sebti, S. M. Antitumor efficacy of a novel class of non-thiol-containing peptidomimetic inhibitors of farnesyltransferase and geranylgeranyltransferase I: combination therapy with the cytotoxic agents cisplatin, Taxol, and gemcitabine. *Cancer Res.* 1999, 59, 4919-4926; (c) Ohkanda, J.; Lockman, J. W.; Kothare, M. A.; Qian, Y.; Blaskovich, M. A.; Sebti, S. M.; Hamilton, A. D. Design and synthesis of potent nonpeptidic farnesyltransferase inhibitors based on a terphenyl scaffold. *J. Med. Chem.* 2002, 45, 177-188). With this crystal structure data in hand, the compounds were tailored to become more selective for one enzyme isoform over the other.

Figure 12:
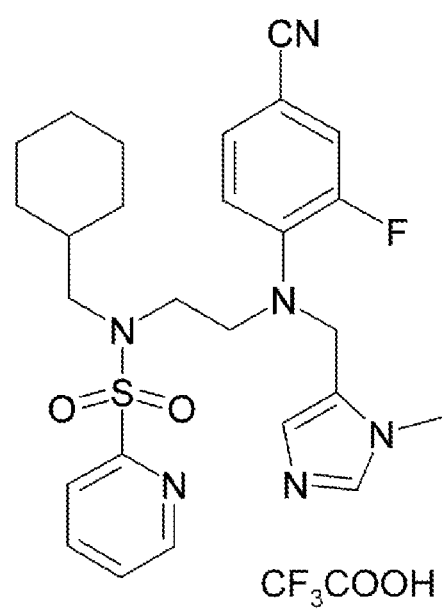
FIG. 12 is a chemical structure diagram of dual FTase and GGTase I inhibitor FGTI-2734.

Additional experiments have been performed to further characterize one of the dual FT/GGT inhibitors. Most of the inhibitors are highly potent and selective for FT, but some are dual inhibitors of both FT and GGT-1. Examples of these are FTI-2586, FTI-2592, FTI-2614, FTI-2602, FTI-2636, FTI-2614, FTI-2615, FTI-2623, FTI-2610, FTI-2586, FTI-2736, FTI-2734, FTI-2735. Three of these, FTI-2734, FTI-2735 and FTI-2736 inhibited FT and GGT-1 in vitro as well as in whole cells. FTI-2734, also called FGTI-2734, seen in FIG. 12 was further focused upon.

FGTI-2734 inhibits both protein farnesylation and geranylgeranylation in human cancer cells.

Figure 13:
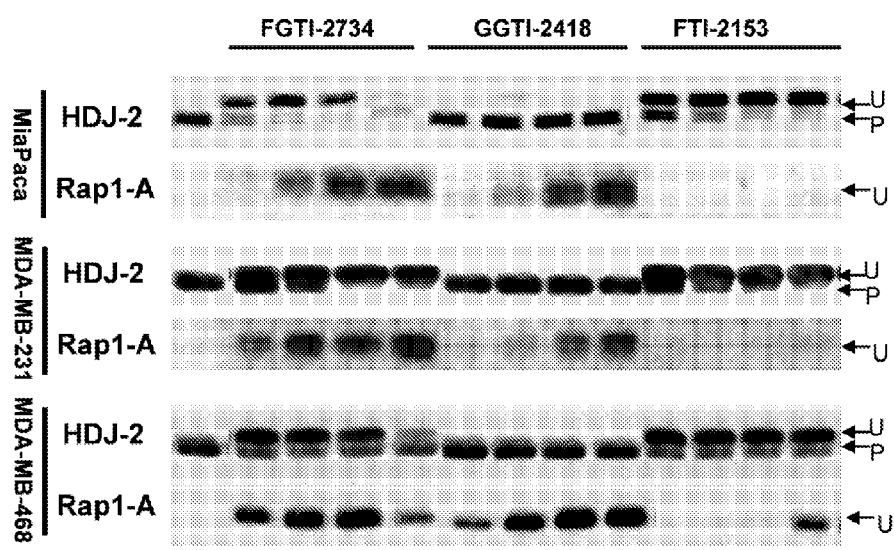
FIG. 13 is a blot showing FGTI-2734 inhibition of both protein farnesylation and geranygeranylation in human cancer cell lines.

FGTI-2734 was shown above to inhibit FT and GGT-I in vitro with $IC_{50}$ values of 250±190 nM and 520±90 nM, respectively. In intact mouse NIH 3T3 cells, FGTI-2734 inhibited H-Ras farnesylation and Rap-1A geranylgeranylation with $IC_{50}$ values of 89±26 nM and 2.7±1.5 µM, respectively. The ability of FGTI-2734 to inhibit HDJ-2 farnesylation and Rap-1A geranylgeranylation in human cancer cells was determined next. To this end, the MiaPaca pancreatic cancer cell line and 2 breast cancer cell lines (MDA-MB-468 and MDA-MB-231) were treated with various concentration of the dual inhibitor FGTI-2734, the GGT-1 inhibitor GGTI-2418 or the FT inhibitor FTI-2153 and processed for Western blotting. FIG. 13 shows that whereas FGTI-2734 inhibited both HDJ-2 farnesylation (as determined by gel shift) and Rap1-A geranylgeranylation (as determined by an antibody that recognizes specifically un-geranylgeranylated Rap-1A), GGTI-2418 inhibited selectively Rap-1A geranylgernylation and FTI-2153 inhibited selectively HDJ-2 farnesylation, seen in FIG. 13.

To determine if FGTI-2734 is more efficacious than FT or GGT-1 inhibitors, 10 human cancer pancreatic cell lines, 2 human breast cancer cell lines, 2 human lung cancer cell lines and one human prostate cancer cell line were treated with these inhibitors and determined their effects on the proliferation of these cells by MTT assay. Table 8 shows that in all cell lines studied except MiaPaca FGTI-2734 was more potent than GGTI-2418, FTI-2153 and FTI-2148.

expected, GGTI-2417 inhibited the processing of Rap1 but not HDJ-2 whereas FTI-2153 inhibited the processing of HDJ-2 but not Rap1.

Figure 16:
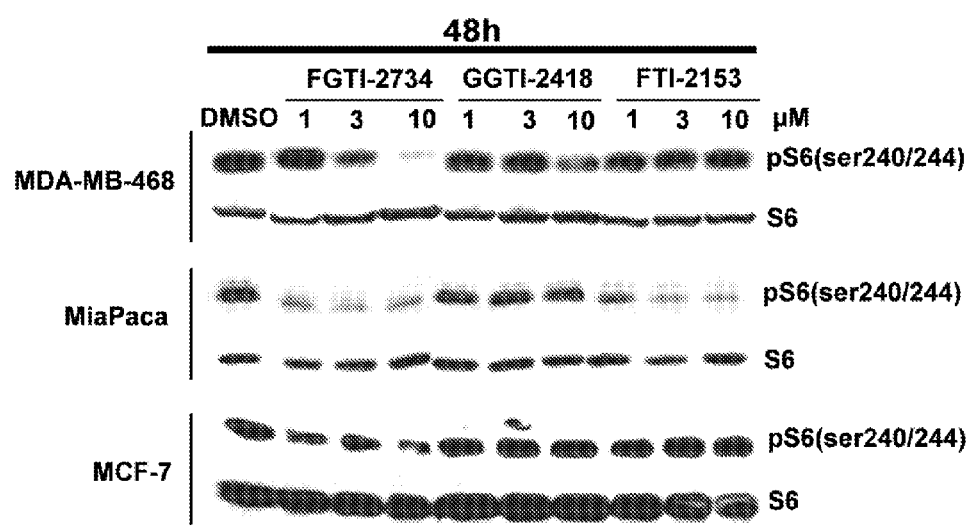
FIG. 16 is a blot showing FGTI-2734 inhibits endogenous mTOR signaling pathway in human cancer cell lines.

Mammalian target of rapamycin (mTOR) is a serine/threonine phosphatidylinositol 3-kinase-related kinase responsible for cell growth, proliferation, cell survival, protein synthesis, and transcription. Alteration of the mTOR pathway, either through activation of oncogenes or inactivation of tumor suppressors, disrupts a signaling equilibrium and causes malignant transformation. Studies have shown that phosphorylated S6 (pS6) is related to mTOR pathway alterations, and is useful in determining PI3K-based cancer therapies (Aziz, et al. Phosphatidylinositol-3-Kinase as a Therapeutic Target in Melanoma. Clin Cancer Res. 2009, 15; 3029-3036). Two breast adenocarcinoma and a pancreatic carcinoma cell line were treated with indicated concentrations of FGTI-2734, GGTI-2417 or FTI-2153. Protein extracts were run on a Western Blot using antibody against pS6 (ser240/244) (Cell Signaling Technology, Inc., Danvers, Mass.). FIG. 16 shows that the dual farnesyltransferase and geranygeranyltransferase-I inhibitors (FGTIs) FGTI-2734

TABLE 8

The inhibition effectiveness of FGTI-2734, GGTI-2418, FTI-2153, and FTI-2148 on the proliferation/viability of human cancer cell lines.

| | | IC50 values (µM) | | | |
|---|---|---|---|---|---|
| Origin | Cell lines | FGTI-2734 | GGTI-2418 | FTI-2153 | FTI-2148 |
| Pancreas | Panc-1 | 20.49 ± 3.18 (n = 6) | >100 (n = 6) | >100 (n = 6) | >100 (n = 4) |
| Pancreas | SW1990 | 26.3, 24.2 (n = 2) | >100 (n = 2) | >100 (n = 2) | >100 (n = 2) |
| Pancreas | ASPC-1 | 11.2, 12.6 (n = 2) | >100 (n = 2) | 41, 40.5 (n = 2) | >100 (n = 2) |
| Pancreas | Capan-2 | 24, 30 (n = 2) | >100 (n = 2) | >100 (n = 2) | >100 (n = 2) |
| Pancreas | MiaPaca | 2.65 ± 0.30 (n = 6) | >100 (n = 4) | 0.33 ± 0.18 (n = 6) | 1.2, 1.2 (n = 2) |
| Pancreas | BxPC3 | 17.2, 17.8 (n = 2) | >100 (n = 2) | 81, 87 (n = 3) | >100 (n = 2) |
| Pancreas | HPNE | 13.5 ± 1.72 (n = 3) | >100 (n = 3) | 54.83 ± 34.21 (n = 3) | >100 (n = 3) |
| Pancreas | HPNE-K-ras | 14.7 ± 0.89 (n = 3) | >100 (n = 3) | 34.21 ± 25.90 (n = 3) | >100 (n = 3) |
| Pancreas | HPDE-C7 | 7.5 | >100 | 68 | >100 |
| Pancreas | HPDE-C7-Kras | 6.6, 8.7 | >100, >100 | 74, 76.5 | >100 (n = 2) |
| Lung | A549 | 13.21 ± 3.64 (n = 8) | >100 (n = 6) | 75 ± 24.94 (n = 4) | >100 (n = 2) |
| Lung | NCI-H460 | 7.19 ± 1.18 (n = 4) | >100 (n = 4) | 13.80 ± 4.12 (n = 4) | NT |
| Breast | MDA-MB-231 | 12.23 ± 0.97 (n = 6) | >30 (n = 2), >50 (n = 2), >100 (n = 2) | >30, >30, >30, >30, 91.5, 87 | NT |
| Breast | MCF-7 | 4.42 ± 0.92 (n = 6) | >100 (n = 4) | 26.57 ± 8.72 (n = 4) | >100, 50 (n = 2) |
| Prostate | DU-145 | 11.23 ± 6.09 (n = 6) | >100 (n = 2), >50 (n = 2) | >100 (n = 2), >30 (n = 2) | NT |

NT = Not determined

Figure 14:
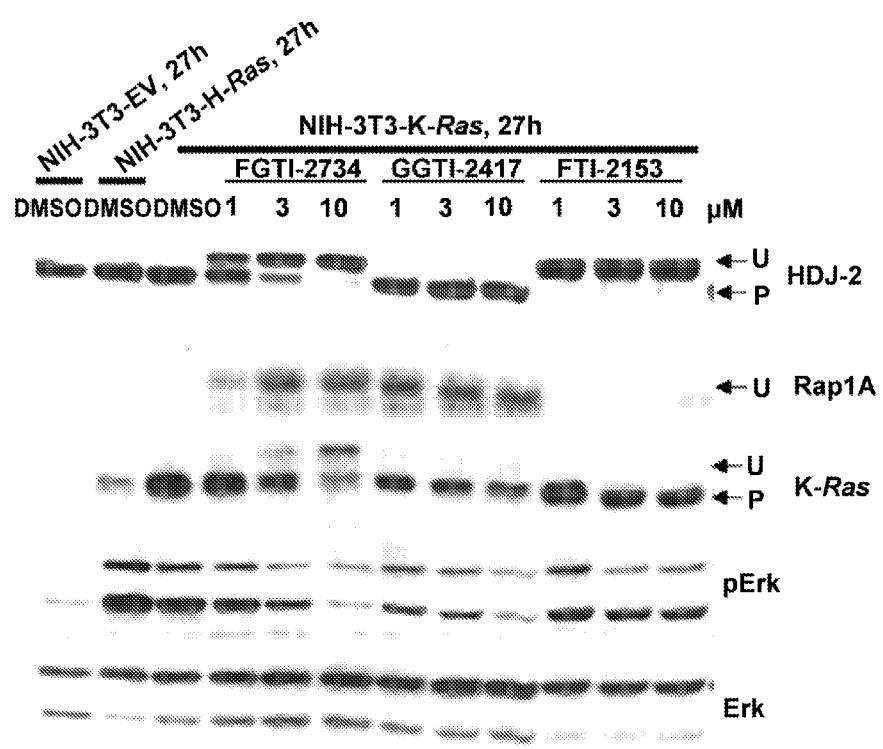
FIG. 14 is a blot showing disruption of oncogenic K-Ras processing/prenylation by FGTI-2734 in NIH 3T3 overexpressing mutant K-Ras.
Figure 15:
FIG. 15 is a blot showing disruption of oncogenic K-Ras processing/prenylation by FGTI-2734 in MDA-MB-231 breast cancer cells that harbor mutant K-Ras.
Figure 17:
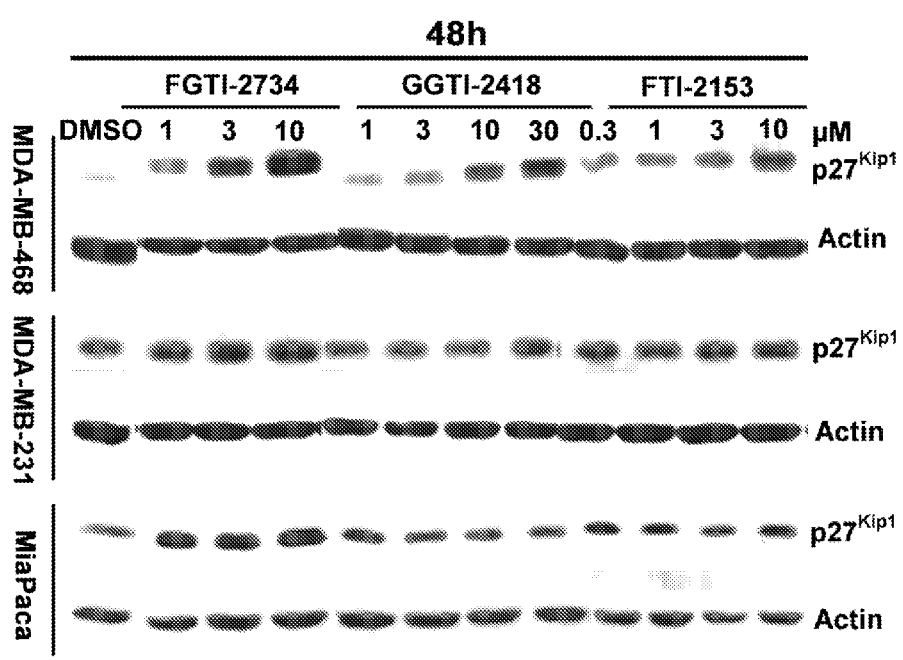
FIG. 17 is a blot showing FGTI-2734 induces p27Kip1 protein levels in human cancer cells.
Figure 18:
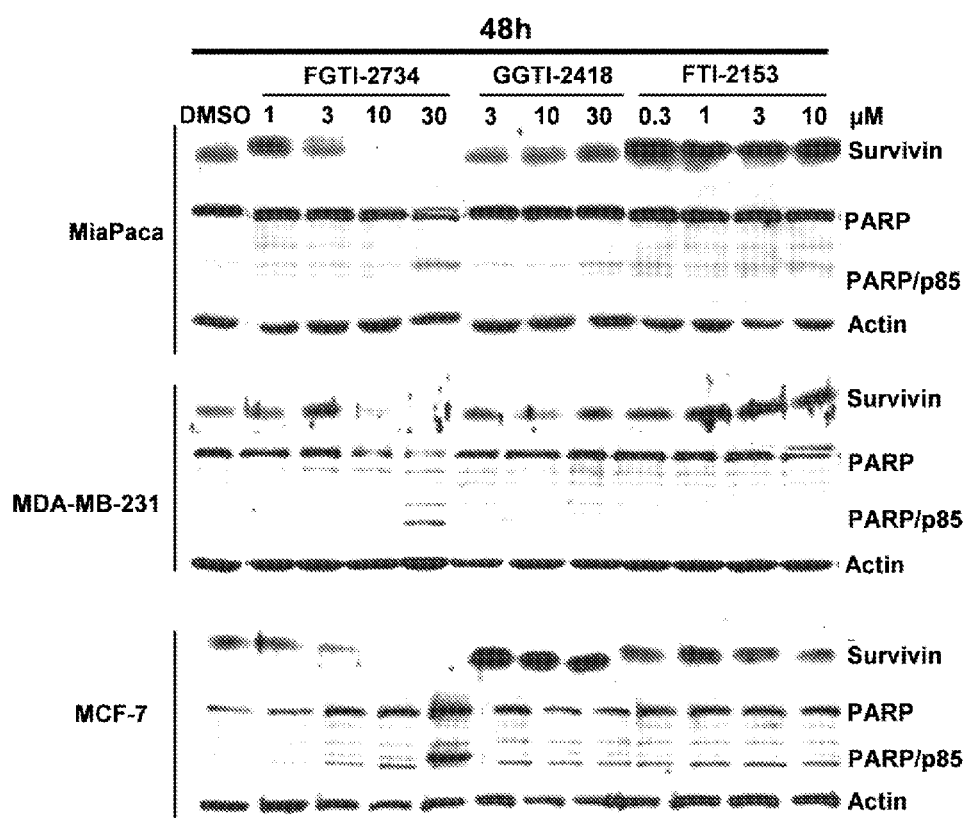
FIG. 18 is a blot showing FGTI-2734 reduces survivin protein levels and induces apoptosis in human cancer cells.

Testing has shown that the dual farnesyltransferase and geranygeranyltransferase-I inhibitors are effective on pancreatic tumors (90% of all cases), colonic tumors (30% of all cases), lung tumors (30% of all cases), and breast tumors (10% of all cases). NIH-3T3 cells that overexpress oncogenic mutant K-Ras, seen in FIG. 14, and MDA-MB-231 breast cancer cells with a naturally occurring K-Ras mutation, seen in FIG. 15, were treated with indicated concentrations of FGTI-2734, GGTI-2417 or FTI-2153. FGTI-2734 but not FTI-2153 or GGTI-2417 inhibited K-Ras prenylation. As blocks mTOR pathway signaling, reducing the levels of pS6. Likewise, the dual farnesyltransferase and geranygeranyltransferase-I inhibitors were found to induce $p27^{Kip1}$ gene, which encodes for cyclin-dependent kinase inhibitors that bind to and prevent the activation of cyclins, as seen in FIG. 17. Blots of breast adenocarcinomas and pancreatic carcinomas treated with the dual farnesyltransferase and geranygeranyltransferase-I inhibitors also show a reduction in surviving protein levels, as seen in FIG. 18. Because survivin inhibits caspase activation, disruption of survivin induction pathways leadis to increased apoptosis and decreased tumour growth, indicating that survivin is a useful target for cancer therapy. In concordance with this, reduction of survivin by FGTI-2734 showed phosphorylation of the pro-apoptotic protein PARP. Antibodies used were HDJ-2 (Lab Vision Corporation, Fremont, Calif.), Rapt (Santa Cruz Biotechnology, Santa Cruz, Calif.), K-Ras (EMD4 Biosciences (Calbiochem), Gibbstown, N.J.), P27 (BD Biosciences, San Jose, Calif.), Actin (Sigma-Aldrich, St. Louis, Mo.), Survivin (Santa Cruz Biotechnology, Santa Cruz, Calif.), and PARP (Roche, Indianapolis, Ind.).

In summary, a potent series of mammalian farnesyltransferase inhibitors (FTIs) was developed based on an ethylenediamine scaffold. This class of compounds was identified by a "piggy-back" approach on potent antimalarial inhibitors of *plasmodium* FTase. The simple and cost-effective ethylenediamine core allowed facile access to a diverse array of inhibitors, greatly facilitating lead inhibitor optimization. Several inhibitors with double-digit nanomolar inhibition of hFTase in vitro were identified, the most potent compound being if ($IC_{50}$=25 nM). In most cases, potent inhibition of hFTase in vitro was accompanied by potent whole cell data (inhibition of H-Ras processing); for example, inhibitor if displayed a whole cell $IC_{50}$ of 90 nM, one of the most active of the entire series. Moreover, in all but two cases inhibitors were selective for hFTase over GGTase-I, with the greatest selectivity (333-fold) exhibited by inhibitor 1g. Finally, the crystal structure of one ethylenediamine-based FTIs (1a) was determined for the active site of rFTase, which assisted in the design of more potent and isoform-selective mammalian farnesyltransferase inhibitors.

4-[(2-Aminoethyl)-(3-methyl-3₁−/−imidazol-4-ylmethyl)-amino]-benzonitrile (8)

To a solution of 4-[(2-{N-tert-butoxycarbonyl}-aminoethyl)-(3-methyl-3H-imidazol-4-ylmethyl)-amino]-benzonitrile, seen as compound 9c in Glenn, et al., Structurally simple, potent, *Plasmodium* selective farnesyltransferase inhibitors that arrest the growth of malaria parasites. *J. Med. Chem.* 2006, 49, 5710-5727, (8.0 g, 30.6 mmol) in $CH_2Cl_2$ (75 mL) cooled to 0° C. was added TFA (75 mL). The reaction was warmed to room temperature and stirred for 30 min, after which time the solvent was evaporated to afford the di-trifluoroacetic acid salt of 8 as a light brown solid (14.8 g, 100%): $δ_H$ (500 MHz, MeOH-$d_4$) 3.20 (t, J=7.1 Hz, 2H, $CH_2CH_2NH_2$), 3.81 (t, J=7.1 Hz, 2H, $CH_2CH_2NH_2$), 3.87 (s, 3H, $CH_3$ (Im)), 4.82 (s, 2H, $CH_2$Im), 6.96 (d, J=9.0 Hz, 2H, 2 CH (Ar)), 7.19 (s, 1H, CH (Im)), 7.56 (d, J=9.0 Hz, 2H, 2 CH (Ar)), 8.88 (s, 1H, CH (Im)); $δ_C$ (125 MHz, MeOH-$d_4$) 33.9, 37.1, 45.3, 48.2, 100.8, 114.0, 118.4, 120.4, 132.3, 134.6, 137.5, 151.0; HRMS (ESI) m/z calculated for [$C_{14}H_{17}N_5$+H] 256.1562. found 256.1559. Subsequently, the free base of 8, which is the form used for all subsequent reactions, was furnished by passing the di-TFA salt through a short pad of silica gel (eluent $CH_2Cl_2$/MeOH/$NH_4OH$, 92:7:1).

N-Benzyl, N-{2-[(4-cyanophenyl)-(3-methyl-3H-imidazol-4-ylmethyl)-amino]-ethyl}propane-1-sulfonamide (1b)

Compound 8 was treated with propane-1-sulfonyl chloride, on a 0.15 mmol scale. The appropriate sulfonyl chloride (1.2 equiv) was added to a solution of the amine (1 equiv) and DIPEA (2 equiv) in anhydrous $CH_3CN$ (0.1 M) at 0° C. The reaction was warmed to room temperature and stirred for 16 h, at which time the solvent was evaporated. The residue was re-dissolved in $CH_2Cl_2$, washed with 5% $NaHCO_3$, water, brine, dried ($Na_2SO_4$), filtered and concentrated. The crude material was purified by silica gel flash column chromatography (eluent $CH_2Cl_2$/MeOH/$NH_4OH$, 92:7:1) to give N-{2-[(4-cyanophenyl)-(3-methyl-3H-imidazol-4-ylmethyl)-amino]-ethyl}propane-1-sulfonamide as a colorless film (46 mg, 85%): $δ_H$ (500 MHz, MeOH-$d_4$) 0.98 (t, J=7.5 Hz, 3H, $CH_2CH_2CH_3$), 1.71 (sextet, J=7.5 Hz, 2H, $CH_2CH_2CH_3$), 2.96 (m, 2H, $NHCH_2CH_2N$), 3.21-3.26 (m, 2H, $CH_2CH_2CH_3$), 3.61 (t, J=6.5 Hz, 2H, $NHCH_2CH_2N$), 3.84 (s, 3H, $CH_3$ (Im)), 4.79 (s, 2H, $CH_2$Im), 6.91 (d, J=9.1 Hz, 2H, 2 CH (Ar)), 7.20 (s, 1H, CH (Im)), 7.47 (d, J=9.1 Hz, 2H, 2 CH (Ar)), 8.82 (s, 1H, CH (Im)); $δ_C$ (125 MHz, MeOH-$d_4$) 11.7, 16.9, 32.8, 39.7, 44.4, 50.6, 53.2, 98.9, 112.6, 117.7, 119.4, 131.5, 133.3, 136.2, 150.4; LRMS (ESI) 384.2 [$C_{17}H_{23}N_5O_2S$+Na]. Subsequently, the sulfonamide (36 mg, 0.1 mmol) was treated with benzyl bromide. To a solution of the sulfonamide (1 equiv) and $Cs_2CO_3$ (2 equiv) in DMF (0.1 M) at 0° C. was added the appropriate alkyl bromide or chloride (1.1 equiv). The resulting mixture was stirred at room temperature overnight. The reaction was diluted with water, then extracted into EtOAc (×3). The combined EtOAc extractions were washed with 5% $NaHCO_3$ (×3), brine, dried ($Na_2SO_4$), filtered and concentrated. After the usual work-up and flash chromatography over silica gel (eluent $CH_2Cl_2$/MeOH/$NH_4OH$, 192:7:1) the title compound 1b was furnished as a glassy film (37 mg, 82%): $δ_H$ (400 MHz, MeOH-$d_4$) 1.20 (t, J=7.4 Hz, 3H, $CH_2CH_2CH_3$), 1.99 (m, 2H, $CH_2CH_2CH_3$), 3.24 (t, J=7.8 Hz, 2H, N(Bn)$CH_2CH_2N$), 3.40 (obscured, 4H, $NHCH_2CH_2N$, $CH_2CH_2CH_3$), 3.94 (s, 3H, $CH_3$ (Im)), 4.52 (s, 2H, $CH_2$Ph), 4.65 (s, 2H, $CH_2$Im), 6.75 (d, J=8.9 Hz, 2H, 2 CH (Ar)), 7.25 (s, 1H, CH (Im)), 7.55 (m, 7H, 5 CH (Ph), 2 CH (Ar)), 9.00 (s, 1H, CH (Im)); $δ_C$ (125 MHz, MeOH-$d_4$) 13.7, 18.6, 34.6, 45.4, 46.8, 51.6, 53.4, 55.1, 100.3, 114.1, 119.6, 121.2, 129.8, 130.7, 133.1, 135.1, 138.2, 138.7, 151.9, 152.9; HRMS (ESI) m/z calculated for [$C_{24}H_{29}N_5O_2S$+H] 452.2120. found 452.2108; HPLC (I) $t_R$=13.45 min (100%), (II) $t_R$=19.72 min (100%).

N-Benzyl, N-{2-[(4-cyanophenyl)-(3-methyl-3H-imidazol-4-ylmethyl)-amino]-ethyl}cyclopropanesulfonamide (1c)

First, amine 8 was reacted with cyclopropanesulfonyl chloride, on a 0.15 mmol scale. The appropriate sulfonyl chloride (1.2 equiv) was added to a solution of the amine (1 equiv) and DIPEA (2 equiv) in anhydrous $CH_3CN$ (0.1 M) at 0° C. The reaction was warmed to room temperature and stirred for 16 h, at which time the solvent was evaporated. The residue was re-dissolved in $CH_2Cl_2$, washed with 5% $NaHCO_3$, water, brine, dried ($Na_2SO_4$), filtered and concentrated. After work-up and flash column chromatography (eluent $CH_2Cl_2$/MeOH/$NH_4OH$, 92:7:1), N-{2-[(4-cyanophenyl)-(3-methyl-3H-imidazol-4-ylmethyl)-amino]-ethyl}cyclopropanesulfonamide was yielded as a colorless film (44 mg, 82%): $δ_H$ (500 MHz, MeOH-$d_4$) 0.98 (m, 4H, 2 $CH_2$ (cyclopropyl)), 2.51 (m, 1H, CH (cyclopropyl)), 3.33 (t, J=5.8 Hz, 2H, NH$\underline{CH_2}$$CH_2$N), 3.67 (t, J=5.8 Hz, 2H, NH$CH_2$$\underline{CH_2}$N), 3.88 (s, 3H, $CH_3$ (Im)), 4.76 (s, 2H, $CH_2$Im), 6.95 (d, J=8.83 Hz, 2H, 2 CH (Ar)), 7.25 (s, 1H, CH (Im)), 7.53 (d, J=8.84 Hz, 2H, 2 CH (Ar)), 8.86 (s, 1H, CH (Im)); $δ_C$ (125 MHz, MeOH-$d_4$) 4.1, 29.0, 32.8, 39.9, 44.5, 50.5, 99.1, 112.7, 117.8, 119.4, 131.6, 133.4, 136.3, 150.4; LRMS (ESI) 382.1 [$C_{17}H_{21}N_5O_2S$+Na]. Subsequently, the sulfonamide (36 mg, 0.1 mmol) was treated with benzyl bromide. To a solution of the sulfonamide (1 equiv) and $Cs_2CO_3$ (2 equiv) in DMF (0.1 M) at 0° C. was added the appropriate alkyl bromide or chloride (1.1 equiv). The resulting mixture was stirred at room temperature overnight. The reaction was diluted with water, then extracted into EtOAc (×3). The combined EtOAc extractions were washed with 5% NaHCO$_3$ (×3), brine, dried (Na$_2$SO$_4$), filtered and concentrated. The crude material was dry-loaded onto silica gel and purified by flash column chromatography (eluent CH$_2$Cl$_2$/MeOH/NH$_4$OH, 192:7:1) to give 1c as a white foam (40 mg, 89%): δ$_H$ (500 MHz, MeOH-d$_4$) 0.95 (m, 4H, 2 CH$_2$ (cyclopropyl)), 2.55 (m, 1H, CH (cyclopropyl)), 3.31 (m, 4H, NCH$_2$CH$_2$N), 3.71 (s, 3H, CH$_3$ (Im)), 4.32 (s, 2H, CH$_2$Ph), 4.43 (s, 2H, CH$_2$Im), 6.51 (d, J=8.89 Hz, 2H, 2 CH (Ar)), 7.02 (s, 1H, CH (Im)), 7.26-7.33 (m, 7H, 5 CH (Ph), 2 CH (Ar)), 8.76 (s, 1H, CH (Im)); δ$_C$ (125 MHz, MeOH-d$_4$) 5.3, 28.1, 34.3, 45.1, 46.3, 51.1, 54.9, 100.3, 113.7, 119.1, 120.8, 129.4, 129.9, 130.3, 132.7, 134.7, 137.8, 138.2, 151.5; HRMS (ESI) m/z calculated for [C$_{24}$H$_{27}$N$_5$O$_2$S+H] 450.1964. found 450.1985; HPLC (I) t$_R$=12.70 min (100%), (II) t$_R$=18.99 min (100%).

[N-(Furan-3-ylmethyl), N-{2-[(4-cyanophenyl)-(3-methyl-3H-imidazol-4-ylmethyl)-amino]-ethyl}]1-methyl-1H-imidazole-4-sulfonamide (1ah, 4.38)

Furan-3-carbaldehyde was reductively aminated with amine 8, on a 0.15 mmol scale. To a solution of 8 (1 equiv) in dry methanol (0.2 M) with 4 Å molecular sieves was added the appropriate aldehyde (1.1 equiv) and acetic acid (1.3 eq). The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. Purification by flash column chromatography (eluent CH$_2$Cl$_2$/MeOH/NH$_4$OH, 92:7:1) then gave 4-[{2-[(furan-3-ylmethyl)-amino]-ethyl}-(3-methyl-3H-imidazol-4-ylmethyl)-amino]-benzonitrile as a film (39 mg, 78%): δ$_H$ (400 MHz, MeOH-d$_4$) 3.24 (obscured t, 2H, NHCH$_2$CH$_2$N), 3.78 (m, 5H, NHCH$_2$CH$_2$N, CH$_3$ (Im)), 4.07 (s, 2H, CH$_2$-furan), 4.75 (s, 2H, CH$_2$Im), 6.50 (s, 1H, CH (furan)), 6.88 (d, J=9.0 Hz, 2H, 2 CH (benzonitrile)), 7.11 (s, 1H, CH (furan)), 7.42-7.53 (m, 3H, 2 CH (benzonitrile), CH (Im)), 7.62 (s, 1H, CH (furan)), 8.82 (s, 1H, CH (Im)); δ$_C$ (100 MHz, MeOH-d$_4$) 34.5, 43.5, 44.7, 45.9, 47.7, 101.7, 111.9, 114.5, 117.3, 119.0, 120.8, 132.9, 135.2, 138.2, 145.1, 146.0, 151.5; LRMS (ESI) m/z 358.2 [C$_{19}$H$_{21}$N$_5$O+Na]. This secondary amine (34 mg, 0.1 mmol) was reacted with 1-methyl-1H-imidazole-4-sulfonyl chloride to yield the title compound 1ah as a white foam (43 mg, 90%). The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated.

δ$_H$ (500 MHz, MeOH-d$_4$) 3.38 (obscured t, 2H, ((furan-3-ylmethyl)NHCH$_2$CH$_2$N)), 3.56 (t, J=7.0 Hz, 2H, ((furan-3-ylmethyl)NHCH$_2$CH$_2$N)), 3.81 (s, 3H, CH$_3$ (Im)), 3.89 (s, 3H, CH$_3$ (Im)), 4.19 (s, 2H, CH$_2$-furan), 4.70 (s, 2H, CH$_2$Im), 6.57 (s, 1H, CH (furan)), 6.77 (d, J=8.94 Hz, 2H, 2 CH (benzonitrile)), 7.25 (s, 1H, CH (furan)), 7.46*-7.52 (m, 4H, 2 CH (benzonitrile), 2 CH (Im)), 7.78 (s, 1H, CH (furan)), 7.81 (s, 1H, CH (Im)), 8.91 (s, 1H, CH (Im)); δ$_C$ (125 MHz, MeOH-d$_4$) 34.3, 34.4, 45.3, 45.5, 45.9, 51.0, 100.4, 111.9, 113.8, 119.3, 120.8, 122.0, 126.8, 132.9, 134.8, 137.9, 139.1, 141.5, 143.2, 145.3, 151.7; HRMS (ESI) m/z calculated for [C$_{23}$H$_{25}$N$_7$O$_3$S+H] 480.1818. found 480.1809; HPLC (I) t$_R$=12.62 min (100%).

[N-(Thiophen-3-ylmethyl), N-{2-[(4-cyanophenyl)-(3-methyl-3H-imidazol-4-ylmethyl)-amino]-ethyl}]1-methyl-1H-imidazole-4-sulfonamide (1ai, 4.39)

Thiophene-3-carbaldehyde was reductively aminated with amine 8 (38 mg, 0.15 mmol). To a solution of 8 (1 equiv) in dry methanol (0.2 M) with 4 Å molecular sieves was added the appropriate aldehyde (1.1 equiv) and acetic acid (1.3 eq). The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. The amination provided, after flash column chromatography (eluent CH$_2$Cl$_2$/MeOH/NH$_4$OH, 92:7:1), 4-((3-methyl-3H-imidazol-4-ylmethyl)-{2-[(thiophen-3-ylmethyl)-amino]-ethyl}-amino)-benzonitrile as a glassy film (40 mg, 76%): δ$_H$ (400 MHz, MeOH-d$_4$) 3.20 (obscured t, 2H, NHCH$_2$CH$_2$N), 3.70-3.75 (m, 5H, NHCH$_2$CH$_2$N, CH$_3$ (Im)), 4.16 (s, 2H, CH$_2$-thiophene), 4.69 (s, 2H, CH$_2$Im), 6.74 (d, J=9.0 Hz, 2H, 2 CH (benzonitrile)), 7.06 (s, 1H, CH (Im)), 7.09 (d, J=3.9 Hz, 1H, CH (thiophene)), 7.41-7.48 (m, 4H, 2 CH (benzonitrile), 2 CH (thiophene)), 8.77 (s, 1H, CH (Im)); δ$_C$ (100 MHz, MeOH-d$_4$) 34.7, 45.0, 46.1, 47.4, 47.9, 102.0, 114.7, 119.2, 120.9, 129.0, 129.1, 129.5, 133.1, 133.2, 135.4, 138.4, 151.6; LRMS (ESI) m/z 374.2 [C$_{19}$H$_{21}$N$_5$S+Na]. This secondary amine (35 mg, 0.1 mmol) was then reacted with 1-methyl-1H-imidazole-4-sulfonyl chloride, after purification by silica gel flash column chromatography (eluent CH$_2$Cl$_2$/MeOH/NH$_4$OH, 192:7:1), compound 1ai as a white foam (46 mg, 93%). The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated.

δ$_H$ (400 MHz, MeOH-d$_4$) 3.29 (obscured t, 2H, ((thiophen-3-ylmethyl)NCH$_2$CH$_2$N)), 3.39 (t, J=6.9 Hz, 2H, ((thiophen-3-ylmethyl)NCH$_2$CH$_2$N)), 3.69 (s, 3H, CH$_3$ (Im)), 3.75 (s, 3H, CH$_3$ (Im)), 4.20 (s, 2H, 2 CH(CH$_2$-thiophene)), 4.50 (s, 2H, CH$_2$Im), 6.57 (d, J=9.1 Hz, 2H, 2 CH (benzonitrile)), 6.95 (d, J=3.8 Hz, 1H, CH (thiophene)), 7.09 (s, 1H, CH (thiophene)), 7.22 (s, 1H, CH (Im)), 7.31 (m, 1H, CH (thiophene)), 7.36 (d, J=9.1 Hz, 2H, 2 CH (benzonitrile)), 7.65 (s, 1H, CH (Im)), 7.70 (s, 1H, CH (Im)), 8.79 (s, 1H, CH (Im)); δ$_C$ (125 MHz, MeOH-d$_4$) 34.7, 34.8, 45.5, 46.7, 50.3, 51.5, 100.7, 114.1, 119.6, 121.2, 126.2, 127.2, 128.3, 129.7, 133.2, 135.2, 138.2, 139.0, 139.5, 141.9, 152.0; HRMS (ESI) m/z calculated for [C$_{23}$H$_{25}$N$_7$O$_2$S$_2$+H] 496.1589. found 496.1576; HPLC (I) t$_R$=12.64 min (99.0%), (II) t$_R$=18.84 min (98.2%).

[N-(Furan-2-ylmethyl), N-{2-[(4-cyanophenyl)-(3-methyl-3H-imidazol-4-ylmethyl)-amino]-ethyl}]1-methyl-1H-imidazole-4-sulfonamide (1aj, 4.41)

Furan-2-carbaldehyde was reductively aminated with amine 8, on a 0.15 mmol scale. To a solution of 8 (1 equiv) in dry methanol (0.2 M) with 4 Å molecular sieves was added the appropriate aldehyde (1.1 equiv) and acetic acid (1.3 eq). The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. Purification by silica gel flash column chromatography (eluent CH$_2$Cl$_2$/MeOH/NH$_4$OH, 92:7:1)

afforded 4-[{2-[(furan-2-ylmethyl)-amino]-ethyl}-(3-methyl-3H-imidazol-4-ylmethyl)-amino]-benzonitrile as a film (39 mg, 78%): δ$_H$ (500 MHz, MeOH-d$_4$) 3.31 (obscured t, 2H, NHCH$_2$CH$_2$N), 3.84 (t, J=7.4 Hz, 2H, NHCH$_2$CH$_2$N), 3.87 (s, 3H, CH$_3$ (Im)), 4.33 (s, 2H, CH$_2$-furan), 4.81 (s, 2H, CH$_2$Im), 6.48 (m, 1H, CH (furan)), 6.61 (d, J=3.19 Hz, 1H, CH (furan)), 6.95 (d, J=8.9 Hz, 2H, 2 CH (benzonitrile)), 7.18, (s, 1H, CH (Im)), 7.54 (d, J=8.9 Hz, 2H, 2 CH (benzonitrile)), 7.60 (m, 1H, CH (furan)), 8.88 (s, 1H, CH (Im)); δ$_C$ (125 MHz, MeOH-d$_4$) 32.8, 43.0, 43.1, 44.2, 46.0, 100.1, 110.7, 112.4, 113.0, 117.4, 119.0, 131.2, 133.5, 136.5, 144.5, 144.8, 149.7; LRMS (ESI) m/z 358.2 [C$_{19}$H$_{21}$N$_5$O+Na]. This secondary amine was reacted with 1-methyl-1H-imidazole-4-sulfonyl chloride on a 0.1 mmol scale. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated. After work-up, the crude material was purified by silica gel flash column chromatography (eluent CH$_2$Cl$_2$/MeOH/NH$_4$OH, 192:7:1) to furnish the title compound 1aj as a white foam (43 mg, 90% 47.91818): δ$_H$ (500 MHz, MeOH-d$_4$) 3.34 (t, J=6.9 Hz, 2H, ((furan-3-ylmethyl)NCH$_2$CH$_2$N)), 3.46 (t, J=6.9 Hz, 2H, ((furan-3-ylmethyl)NCH$_2$CH$_2$N)), 3.67 (s, 3H, CH$_3$ (Im)), 3.79 (s, 3H, CH$_3$ (Im)), 4.23 (s, 2H, CH$_2$-furan), 4.63 (s, 2H, CH$_2$Im), 6.18 (m, 1H, CH (furan)), 6.23 (m, 1H, CH (furan)), 6.73 (d, J=9.1 Hz, 2H, 2 CH (benzonitrile)), 7.15 (s, 1H, CH (Im)), 7.29 (s, 1H, CH (furan)), 7.41 (d, J=9.1 Hz, 2H, 2 CH (benzonitrile)), 7.59 (s, 1H, CH (Im)), 7.64 (s, 1H, CH (Im)), 8.79 (s, 1H, CH (Im)); δ$_C$ (125 MHz, MeOH-d$_4$) 34.3, 45.4, 46.5, 47.1, 49.6 (obscured), 50.8, 100.4, 111.3, 111.7, 113.9, 119.3, 120.9, 126.8, 132.9, 134.8, 137.8, 139.1, 141.4, 144.4, 150.9, 151.8; HRMS (ESI) m/z calculated for [C$_{23}$H$_{25}$N$_7$O$_3$S+H] 480.1818. found 480.1833; HPLC (I) t$_R$=12.51 min (100%).

[N-(Thiophen-2-ylmethyl), N-{2-[(4-cyanophenyl)-(3-methyl-3H-imidazol-4-ylmethyl)-amino]-ethyl}] 1-methyl-1H-imidazole-4-sulfonamide (1ak, 4.42)

Thiophene-2-carbaldehyde was reductively aminated with amine 8 (38 mg, 0.15 mmol). To a solution of 8 (1 equiv) in dry methanol (0.2 M) with 4 Å molecular sieves was added the appropriate aldehyde (1.1 equiv) and acetic acid (1.3 eq). The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. The amination provided, after flash column chromatography (eluent CH$_2$Cl$_2$/MeOH/NH$_4$OH, 92:7:1), 4-((3-methyl-3H-imidazol-4-ylmethyl)-{2-[(thiophen-2-ylmethyl)-amino]-ethyl}-amino)-benzonitrile as a colorless film (38 mg, 72%): δ$_H$ (500 MHz, MeOH-d$_4$) 3.37 (obscured t, 2H, NHCH$_2$CH$_2$N), 3.88-3.92 (m, 5H, NHCH$_2$CH$_2$N, CH$_3$ (Im)), 4.54 (s, 2H, CH$_2$-thiophene), 4.86, (s, 2H, CH$_2$Im), 6.87 (m, 1H, CH (thiophene)), 7.00 (d, J=8.8 Hz, 2H, 2 CH (benzonitrile)), 7.13 (m, 1H, CH (thiophene)), 7.23 (s, 1H, CH (Im)), 7.34 (m, 1H, CH (thiophene)), 7.59 (d, J=8.8 Hz, 2H, 2 CH (benzonitrile)), 8.93 (s, 1H, CH (Im)); δ$_C$ (125 MHz, MeOH-d$_4$) 32.8, 42.9, 44.2, 45.0, 45.9, 100.2, 113.0, 117.4, 119.0, 127.3, 128.2, 130.6, 131.2, 131.5, 133.5, 136.6, 149.7; LRMS (ESI) m/z 374.2 [C$_{19}$H$_{21}$N$_5$S+Na]. This secondary amine (35 mg, 0.1 mmol) was reacted with 1-methyl-1H-imidazole-4-sulfonyl chloride. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated. The usual work-up and purification by flash column chromatography (eluent CH$_2$Cl$_2$/MeOH/NH$_4$OH, 192:7:1) gave 1ak as a glassy film (44 mg, 89%): δ$_H$ (400 MHz, MeOH-d$_4$) 3.31 (t, J=7.1 Hz, 2H, ((thiophen-2-yl) NCH$_2$CH$_2$N)), 3.47 (t, J=7.1 Hz, 2H, ((thiophen-2-yl) NCH$_2$CH$_2$N)), 3.69 (s, 3H, CH$_3$ (Im)), 3.75 (s, 3H, CH$_3$ (Im)), 4.41 (s, 2H, CH$_2$-thiophene), 4.55 (s, 2H, CH$_2$Im), 6.61, (d, J=9.0 Hz, 2H, 2 CH (benzonitrile)), 6.85 (m, 1H, CH (thiophene)), 6.89 (d, J=2.70 Hz, 1H), 7.11 (s, 1H, CH (Im)), 7.29 (m, 1H, CH (thiophene)), 7.37 (d, J=9.0 Hz, 2H, 2 CH (benzonitrile)), 7.67 (s, 1H, CH (Im)), 7.69 (s, 1H, CH (Im)), 8.78 (s, 1H, CH (Im)); δ$_C$ (100 MHz, MeOH-d$_4$) 34.7, 34.8, 45.7, 46.6, 50.3 (obscured), 51.0, 100.9, 114.2, 119.6, 121.2, 126.5, 127.2, 128.5, 130.0, 133.2, 135.2, 138.2, 139.5, 140.7, 141.9, 152.0; HRMS (ESI) m/z calculated for [C$_{23}$H$_{25}$N$_7$O$_2$S$_2$+H] 496.1589. found 496.1585; HPLC (I) t$_R$=12.90 min (100%).

[N-(3,5-Dimethyl-isoxazol-4-ylmethyl), N-{2-[(4-cyanophenyl)-(3-methyl-3H-imidazol-4-ylmethyl)-amino]-ethyl}]1-methyl-1H-imidazole-4-sulfonamide (1al, 4.36)

Amine 8 was reacted with 1-methyl-1H-imidazole-4-sulfonyl chloride, on a 0.15 mmol scale. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated.

Flash column chromatography of the crude material over silica gel (eluent CH$_2$Cl$_2$/MeOH/NH$_4$OH, 92:7:1) afforded 1-methyl-1H-imidazole-4-sulfonic acid {2-[(4-cyano-phenyl)-(3-methyl-3H-imidazol-4-ylmethyl)-amino]-ethyl}-amide as a white powder (55 mg, 92%): δ$_H$ (400 MHz, MeOH-d$_4$) 3.19 (t, J=6.3 Hz, 2H, NHCH$_2$CH$_2$N), 3.64 (t, J=6.3 Hz, 2H, NHCH$_2$CH$_2$N), 3.72 (s, 3H, CH$_3$ (Im)), 3.88 (s, 3H, CH$_3$ (Im)), 4.81 (s, 2H, CH$_2$Im), 6.89 (d, J=9.0 Hz, 2H, 2 CH (benzonitrile)), 7.22 (s, 1H, CH (Im)), 7.50 (d, J=9.0 Hz, 2H, 2 CH (benzonitrile)), 7.62 (s, 1H, CH (Im)), 7.71 (s, 1H, CH (Im)), 8.87 (s, 1H, CH (Im)); δ$_C$ (100 MHz, MeOH-d$_4$) 33.8, 33.9, 40.7, 45.4, 50.9, 99.5, 113.5, 118.5, 120.5, 125.3, 132.3, 134.2, 137.2, 139.9, 140.7, 151.2; HRMS (ESI) m/z calculated for [C$_{18}$H$_{21}$N$_7$O$_2$S+H] 400.1556. found 400.1545. This secondary sulfonamide was then alkylated with 4-chloromethyl-3,5-dimethyl-isoxazole, on a 0.1 mmol scale. To a solution of the sulfonamide (1 equiv) and Cs$_2$CO$_3$ (2 equiv) in DMF (0.1 M) at 0° C. was added the appropriate alkyl bromide or chloride (1.1 equiv). The resulting mixture was stirred at room temperature overnight. The reaction was diluted with water, then extracted into EtOAc (×3). The combined EtOAc extractions were washed with 5% NaHCO$_3$ (×3), brine, dried (Na$_2$SO$_4$), filtered and concentrated. After work-up, purification was accomplished by silica gel flash column chromatography (eluent CH$_2$Cl$_2$/MeOH/NH$_4$OH, 192:7:1) to furnish the title compound 1al as a white foam (40 mg, 79%): δ$_H$ (500 MHz, MeOH-d$_4$) 2.15 (s, 3H, CH$_3$ (isoxazole)), 2.20 (s, 3H, CH$_3$ (isoxazole)), 3.23 (t, J=6.7 Hz, 2H, ((isoxazol-4-ylmethyl)NCH$_2$CH$_2$N)), 3.53 (t, J=6.7 Hz, 2H, ((isoxazol-4-ylmethyl)NCH$_2$CH$_2$N)), 3.77 (s, 3H, CH$_3$ (Im)), 3.82 (s, 3H, CH$_3$ (Im)), 4.02 (s, 2H, CH$_2$-isoxazole), 4.56 (s, 2H, CH$_2$Im), 6.66 (d, J=8.7 Hz, 2H, 2 CH (benzonitrile)), 7.17 (s, 1H, CH (Im)), 7.45 (d, J=8.7 Hz, 2H, 2 CH (benzonitrile)), 7.74 (s, 1H, CH (Im)), 7.78 (s, 1H, CH (Im)), 8.85 (s, 1H, CH (Im)); $\delta_C$ (125 MHz, MeOH-d$_4$) 10.2, 10.9, 34.3, 34.4, 44.4, 45.0, 47.0, 51.2, 100.6, 110.7, 113.7, 119.3, 120.8, 127.1, 132.6, 134.9, 137.9, 138.2, 141.7, 151.4, 161.6, 169.6; HRMS (ESI) m/z calculated for [C$_{24}$H$_{28}$N$_8$O$_3$S+H] 509.2083. found 509.2072; HPLC (I) t$_R$=12.27 min (100%), (II) t$_R$=17.76 min (100%).

[N-(2,4-Dimethyl-thiazol-5-ylmethyl), N-{2-[(4-cyanophenyl)-(3-methyl-3H-imidazol-4-ylmethyl)-amino]-ethyl}]1-methyl-1H-imidazole-4-sulfonamide (1am, 4.40)

2,4-Dimethyl-thiazole-5-carbaldehyde was reductively aminated with amine 8 (38 mg, 0.15 mmol). To a solution of 8 (1 equiv) in dry methanol (0.2 M) with 4 Å molecular sieves was added the appropriate aldehyde (1.1 equiv) and acetic acid (1.3 eq). The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. The amination provided, after flash column chromatography (eluent CH$_2$Cl$_2$/MeOH/NH$_4$OH, 92:7:1), 4-[{2-[(2,4-dimethyl-thiazol-5-ylmethyl)-amino]-ethyl}-(3-methyl-3H-imidazol-4-ylmethyl)-amino]-benzonitrile as a glassy film (42 mg, 74%): $\delta_H$ (500 MHz, MeOH-d$_4$) 2.34 (s, 3H, CH$_3$ (thiazole)), 2.60 (s, 3H, CH$_3$ (thiazole)), 3.32 (t, J=7.06 Hz, 2H, NHCH$_2$CH$_2$N), 3.83 (m, 5H, NHCH$_2$CH$_2$N, CH$_3$ (Im)), 4.39 (s, 2H, CH$_2$-thiazole), 4.78 (s, 2H, CH$_2$Im), 6.92 (d, J=9.0 Hz, 2H, 2 CH (benzonitrile)), 7.14 (s, 1H, CH (Im)), 7.51 (d, J=9.0 Hz, 2H, 2 CH (benzonitrile)), 8.85 (s, 1H, CH (Im)); LRMS (ESI) m/z 403.2 [C$_{20}$H$_{24}$N$_6$S+Na]. The secondary amine (38 mg, 0.1 mmol) was then treated with 1-methyl-1H-imidazole-4-sulfonyl chloride. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated.

Work-up and purification (flash column chromatography (eluent CH$_2$Cl$_2$/MeOH/NH$_4$OH, 192:7:1)) as usual yielded 1am as a white foam (47 mg, 90%): $\delta_H$ (500 MHz, MeOH-d$_4$) 2.21 (s, 3H, CH$_3$ (thiazole)), 2.55 (s, 3H, CH$_3$ (thiazole)), 3.39 (t, J=6.5 Hz, 2H, ((thiazol-5-ylmethyl)NCH$_2$CH$_2$N)), 3.64 (t, J=6.5 Hz, 2H, ((thiazol-5-ylmethyl)NCH$_2$CH$_2$N)), 3.77 (s, 3H, CH$_3$ (Im)), 3.86 (s, 3H, CH$_3$ (Im)), 4.38 (s, 2H, CH$_2$-thiazole), 4.73 (s, 2H, CH$_2$Im), 6.71 (d, J=9.1 Hz, 2H, 2 CH (benzonitrile)), 7.20 (s, 1H, CH (Im)), 7.46 (d, J=9.1 Hz, 2H, 2 CH (benzonitrile)), 7.76 (s, 1H, CH (Im)), 7.79 (s, 1H, CH (Im)), 8.87 (s, 1H, CH (Im)); $\delta_C$ (125 MHz, MeOH-d$_4$) 14.8, 18.9, 34.7, 34.8, 45.9, 47.3, 47.6, 51.3, 100.8, 114.0, 119.6, 121.1, 127.5, 128.6, 133.2, 135.2, 138.3, 138.8, 142.0, 142.1, 150.9, 151.8; HRMS (ESI) m/z calculated for [C$_{24}$H$_{28}$N$_8$O$_2$S$_2$+H] 525.1855. found 525.1828; HPLC (I) t$_R$=12.14 min (96.61%), (II) t$_R$=17.00 min (96.03%).

[N-(1,3,5-Trimethyl-1H-pyrazol-4-ylmethyl), N-{2-[(4-cyanophenyl)-(3-methyl-3H-imidazol-4-ylmethyl)-amino]-ethyl}]1-methyl-1H-imidazole-4-sulfonamide (1an, 4.49)

Trimethyl-1H-pyrazole-4-carbaldehyde was reductively aminated with amine 8, on a 0.15 mmol scale. To a solution of 8 (1 equiv) in dry methanol (0.2 M) with 4 Å molecular sieves was added the appropriate aldehyde (1.1 equiv) and acetic acid (1.3 eq). The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. The crude material was chromatographed over silica gel (eluent CH$_2$Cl$_2$/MeOH/NH$_4$OH, 92:7:1) to give 4-((3-Methyl-3H-imidazol-4-ylmethyl)-{2-[(1,3,5-trimethyl-1H-pyrazol-4-ylmethyl)-amino]-ethyl}-amino)-benzonitrile as a film (46 mg, 81%): $\delta_H$ (400 MHz, MeOH-d$_4$) 2.28 (s, 3H, CH$_3$ (pyrazole)), 2.34 (s, 3H, CH$_3$ (pyrazole)), 3.39 (t, J=7.5 Hz, 2H, NHCH$_2$CH$_2$N), 3.75 (s, 3H, N—CH$_3$ (pyrazole)), 3.88-3.95 (m, 5H, NHCH$_2$CH$_2$N, CH$_3$ (Im)), 4.15 (s, 2H, CH$_2$-pyrazole), 4.88 (s, 2H, CH$_2$Im), 7.01 (d, J=8.9 Hz, 2H, 2 CH (benzonitrile)), 7.22 (s, 1H, CH (Im)), 7.59 (d, J=8.9 Hz, 2H, 2 CH (benzonitrile)), 8.94 (s, 1H, CH (Im)); $\delta_C$ (125 MHz, MeOH-d$_4$) 9.8, 11.4, 34.3, 36.1, 42.3, 44.7, 45.6, 47.5, 99.9, 108.3, 114.3, 118.8, 120.6, 132.8, 135.0, 138.0, 142.6, 148.5, 151.3; LRMS (ESI) m/z 400.2 [C$_{21}$H$_{27}$N$_7$+Na]. This secondary amine (38 mg, 0.1 mmol) was then reacted with 1-methyl-1H-imidazole-4-sulfonyl chloride. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated. Work-up then the usual purification (silica gel flash column chromatography (eluent CH$_2$Cl$_2$/MeOH/NH$_4$OH, 192:7:1)) furnished the title compound 1an as a white foam (44 mg, 84%): $\delta_H$ (500 MHz, MeOH-d$_4$) 2.00 (s, 3H, CH$_3$ (pyrazole)), 2.06 (s, 3H, CH$_3$ (pyrazole)), 3.15 (t, J=6.5 Hz, 2H, ((pyrazole-4-ylmethyl)NCH$_2$CH$_2$N)), 3.44 (t, J=6.5 Hz, 2H, ((pyrazole-4-ylmethyl)NCH$_2$CH$_2$N)), 3.51 (s, 3H, N—CH$_3$ (pyrazole)), 3.73 (s, 3H, CH$_3$ (Im)), 3.78 (s, 3H, CH$_3$ (Im)), 3.92 (s, 2H, CH$_2$-pyrazole), 4.48 (s, 2H, CH$_2$Im), 6.50 (d, J=8.9 Hz, 2H, 2 CH (benzonitrile)), 7.11 (s, 1H, CH (Im)), 7.39 (d, J=8.9 Hz, 2H, 2 CH (benzonitrile)), 7.72 (s, 1H, CH (Im)), 7.75 (s, 1H, CH (Im)), 8.80 (s, 1H, CH (Im)); $\delta_C$ (125 MHz, MeOH-d$_4$) 9.5, 11.7, 34.3, 34.4, 36.0, 45.1, 45.4, 46.5, 51.2, 100.2, 111.8, 113.4, 119.2, 120.8, 127.1, 132.7, 134.8, 137.9, 138.1, 141.2, 141.7, 147.9, 151.4; HRMS (ESI) m/z calculated for [C$_{25}$H$_{31}$N$_9$O$_2$S+H] 522.2400. found 522.2377; HPLC (I) t$_R$=12.49 min (95.83%), (II) t$_R$=17.78 min (96.33%).

[N-(Cyclopropylmethyl), N-{2-[(4-cyanophenyl)-(3-methyl-3H-imidazol-4-ylmethyl)-amino]-ethyl}]1-methyl-1H-imidazole-4-sulfonamide (1aw, 4.34)

First, cyclopropanecarbaldehyde was reductively aminated with amine 8 (38 mg, 0.15 mmol). To a solution of 8 (1 equiv) in dry methanol (0.2 M) with 4 Å molecular sieves was added the appropriate aldehyde (1.1 equiv) and acetic acid (1.3 eq). The reaction was stirred under nitrogen at room temperature for 30 minutes. Sodium cyanoborohydride (1.5 eq) was added and the resulting suspension was stirred at room temperature overnight. The reaction mixture was decanted and then dry-loaded onto silica gel. Flash column chromatography (eluent CH$_2$Cl$_2$/MeOH/NH$_4$OH, 92:7:1) purified the material to give 4-[[2-(cyclopropylmethyl-amino)-ethyl]-(3-methyl-3H-imidazol-4-ylmethyl)-amino]-benzonitrile as a colorless film (39 mg, 84%): $\delta_H$ (400 MHz, CDCl$_3$) 0.07 (m, 2H, 2 CH (cyclopropyl)), 0.46 (m, 2H, 2 CH (cyclopropyl)), 0.78 (m, 1H, CHCH$_2$NHCH$_2$CH$_2$N), 2.41

(m, 2H, CH$_2$-cyclopropyl), 2.75 (s, 2H, NHCH$_2$CH$_2$N), 3.50 (m, 2H, NHCH$_2$CH$_2$N), 3.55 (s, 3H, CH$_3$ (Im)), 4.88 (s, 2H, CH$_2$Im), 6.68 (d, J=8.8 Hz, 2H, 2 CH (benzonitrile)), 6.86 (s, 1H, CH (Im)), 7.26 (s, 1H, CH (Im)), 7.46 (d, J=8.8 Hz, 2H, 2 CH (benzonitrile); LRMS (ESI) m/z 332.2 [C$_{18}$H$_{23}$N$_5$+Na]. This secondary amine was then reacted with 1-methyl-1H-imidazole-4-sulfonyl chloride, on a 0.1 mmol scale. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated. After work-up, the crude material was purified by silica gel flash column chromatography (eluent CH$_2$Cl$_2$/MeOH/NH$_4$OH, 192:7:1) to furnish 1aw as a white powder (39 mg, 86%): δ$_H$ (500 MHz, MeOH-d$_4$) 0.14 (m, 2H, 2 CH (cyclopropyl)), 0.43 (m, 2H, 2 CH (cyclopropyl)), 0.84 (m, 1H, CHCH$_2$NCH$_2$CH$_2$N), 2.50 (d, J=6.9, 2H, CH$_2$-cyclopropyl), 2.99 (t, J=6.9 Hz, 2H ((cyclopropylmethyl) NCH$_2$CH$_2$N)), 3.73 (s, 3H, CH$_3$ (Im)), 3.81 (t, J=6.9 Hz, 2H, ((cyclopropylmethyl) NCH$_2$CH$_2$N)), 3.88 (s, 3H, CH$_3$ (Im)), 4.85 (s, 2H, CH$_2$Im), 6.97 (d, J=9.1 Hz, 2H, 2 CH (benzonitrile)), 7.28 (s, 1H, CH (Im)), 7.62 (d, J=9.1 Hz, 2H, 2 CH (benzonitrile)), 7.67 (s, 1H, CH (Im)), 7.71 (s, 1H, CH (Im)), 8.87 (s, 1H, CH (Im)); δ$_C$ (125 MHz, MeOH-d$_4$) 4.6, 11.0, 34.3, 34.4, 45.8, 46.8, 51.6, 55.9, 100.4, 114.1, 119.3, 120.9, 126.5, 133.1, 134.9, 137.9, 139.5, 141.4, 151.9; HRMS (ESI) m/z calculated for [C$_{22}$H$_{27}$N$_7$O$_2$S+H] 454.2025. found 454.2009; HPLC (I) t$_R$=12.55 min (99.05%), (II) t$_R$=18.46 min (98.47%).

tert-Butyl 4-[{2-[benzyl-(1-methyl-1H-imidazole-4-sulfonyl)-amino]-ethyl}-(3-methyl-3H-imidazol-4-ylmethyl)-amino]-benzoate (10, SF-7-138)

tert-Butyl p-fluorobenzoate (750 mg, 3.93 mmol, 1 equiv) was dissolved in ethylenediamine (4 mL), and heated to 120° C. for 24 h. All solvent was evaporated, and then the residue was dry-loaded onto silica gel and purified by flash column chromatography (eluent CH$_2$Cl$_2$/MeOH/NH$_4$OH, 92:7:1) to furnish tert-butyl 4-(2-amino-ethylamino)-benzoate as a white powder (891 mg, 96%): δ$_H$ (400 MHz, CD$_2$Cl$_2$) 1.59 (s, 9H, CO$_2$(CH$_3$)$_3$), 2.98 (t, J=5.8 Hz, 2H, H$_2$NCH$_2$CH$_2$NH), 3.23 (q, J=5.8 Hz, 2H, H$_2$NCH$_2$CH$_2$NH), 4.67 (br, 1H, H$_2$NCH$_2$CH$_2$NH), 6.62 (d, J=8.6 Hz, 2H, 2 CH (Ar)), 7.81 (d, J=8.6 Hz, 2H, 2 CH (Ar)); δ$_C$ (125 MHz, CD$_2$Cl$_2$) 28.9, 41.7, 46.6, 80.3, 112.1, 120.9, 131.9, 152.9, 166.7; HRMS (EI+) m/z calcd for [C$_{13}$H$_{20}$N$_2$O$_2$] 236.1525. found 236.1527. tert-Butyl 4-(2-amino-ethylamino)-benzoate (700 mg, 3.03 mmol, 1 equiv) was then sulfonylated with 1-methyl-1H-imidazole-4-sulfonyl chloride. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated. The crude material was dry-loaded onto silica gel, and then purified by flash column chromatography (eluent CH$_2$Cl$_2$/MeOH/NH$_4$OH, 192:7:1) to give tert-butyl 4-[2-(1-methyl-1H-imidazole-4-sulfonylamino)-ethylamino]-benzoate as a white powder (1.04 g, 90%): δ$_H$ (500 MHz, CDCl$_3$) 1.56 (s, 9H, CO$_2$(CH$_3$)$_3$), 3.17 (m, 2H, SO$_2$NHCH$_2$CH$_2$NH), 3.28 (m, 2H, SO$_2$NHCH$_2$CH$_2$NH), 3.67 (s, 3H, CH$_3$ (Im)), 6.51 (d, J=8.5 Hz, 2H, 2 CH (Ar)), 7.46 (s, 1H, CH (Im)), 7.51 (s, 1H, CH (Im)), 7.75 (d, J=8.5 Hz, 2H, 2 CH (Ar)); δ$_C$ (125 MHz, MeOH-d$_4$) 28.7, 34.6, 42.4, 43.1, 80.8, 111.9, 120.5, 125.2, 131.8, 140.1, 140.3, 152.4, 167.4; HRMS (ES+) calcd for [C$_{17}$H$_{24}$N$_4$O$_4$S+H] 381.1597. found 381.1573. tert-Butyl 4-[2-(1-methyl-1H-imidazole-4-sulfonylamino)-ethylamino]-benzoate (610 mg, 1.63 mmol, 1 equiv) was then chemoselectively benzylated on the sulfonamide NH with benzyl bromide. To a solution of the sulfonamide (1 equiv) and Cs$_2$CO$_3$ (2 equiv) in DMF (0.1 M) at 0° C. was added the appropriate alkyl bromide or chloride (1.1 equiv). The resulting mixture was stirred at room temperature overnight. The reaction was diluted with water, then extracted into EtOAc (×3). The combined EtOAc extractions were washed with 5% NaHCO$_3$ (×3), brine, dried (Na$_2$SO$_4$), filtered and concentrated. The crude material was then flash chromatographed over silica gel to furnish tert-butyl 4-{2-[benzyl-(1-methyl-1H-imidazole-4-sulfonyl)-amino]-ethylamino}-benzoate as a white solid (703 mg, 92%): δ$_H$ (400 MHz, CDCl$_3$) 1.52 (s, 9H, CO$_2$(CH$_3$)$_3$), 3.13 (t, J=6.2 Hz, 2H, (Bn)NCH$_2$CH$_2$NH), 3.43 (t, J=6.2 Hz, 2H, (Bn)NCH$_2$CH$_2$NH), 3.68 (s, 3H, CH$_3$ (Im)), 4.32 (s, 2H, CH$_2$Ph), 6.30 (d, J=8.8 Hz, 2H, 2 CH (Ar)), 7.23-7.30 (m, 5H, 5 CH (Ph)), 7.42 (s, 1H, CH (Im)), 7.49 (s, 1H, CH (Im)), 7.70 (d, J=8.8 Hz, 2H, 2 CH (Ar)); δ$_C$ (500 MHz, CDCl$_3$) 28.1, 33.9, 41.6, 46.6, 52.6, 79.6, 111.1, 119.9, 124.4, 127.9, 128.3, 128.6, 131.1, 136.0, 139.0, 139.8, 151.1, 166.1; HRMS (ES+) calcd for [C$_{24}$H$_{30}$N$_4$O$_4$S+H] 471.2066. found 471.2053. tert-Butyl 4-{2-[benzyl-(1-methyl-1H-imidazole-4-sulfonyl)-amino]-ethylamino}-benzoate (220 mg, 0.473 mmol, 1 equiv) was alkylated on the aniline NH with 5-chloromethyl-1-methyl-1H-imidazole.HCl. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. The crude material was flash chromatographed over silica gel (eluent CH$_2$Cl$_2$/MeOH/NH$_4$OH, 192:7:1) to afford the title compound 10 as a colourless foam (200 mg, 76%): δ$_H$ (500 MHz, CDCl$_3$) 1.53 (s, 9H, C(CH$_3$)$_3$), 3.09-3.15 (m, 2H, CH$_2$CH$_2$NSO$_2$), 3.29-3.34 (m, 2H, CH$_2$CH$_2$NSO$_2$), 3.43 (s, 3H, CH$_3$), 3.73 (s, 3H, CH$_3$), 4.26 (s, 2H, CH$_2$Ph), 4.30 (s, 2H, CH$_2$Im), 6.35 (d, J=9.0 Hz, 2H, 2 CH (Ar)), 6.69 (s, 1H, CH (Im)), 7.31-7.37 (m, 5H, 5 CH (Ph)), 7.39 (s, 1H, CH (Im)), 7.42 (s, 1H, CH (Im)), 7.46 (s, 1H, CH (Im)), 7.68 (d, J=9.0 Hz, 2H, 2 CH (Ar)); δ$_C$ (125 MHz, CDCl$_3$) 28.2, 31.6, 33.9, 44.1, 45.0, 49.7, 54.3, 79.8, 111.0, 120.0, 124.4, 127.5, 128.1, 128.6, 128.7, 128.9, 131.1, 136.2, 138.5, 139.0, 139.1, 150.3, 165.8; HRMS calcd for [C$_{29}$H$_{36}$N$_6$O$_4$S+H] 565.2597. found 565.2576; HPLC (I) t$_R$=12.53 min (100%), (II) t$_R$=18.77 min (100%).

4-[{2-[Benzyl-(1-methyl-1H-imidazole-4-sulfonyl)-amino]-ethyl}-(3-methyl-3H-imidazol-4-ylmethyl)-amino]-benzoic acid (11, SF-7-144)

TFA (1.5 mL) was added to a solution of 10 (150 mg, 0.268 mmol, 1 equiv) in CH$_2$Cl$_2$ (1.5 mL), and the resulting mixture was stirred for 3 hours at room temperature, after which time all solvents were evaporated. Residual TFA was removed by repeated co-evaporation with a 2:1 mixture of CHCl$_3$/MeOH, then the residue was purified by silica gel flash column chromatography (eluent CH$_2$Cl$_2$/MeOH/NH$_4$OH, 25:7:1) to afford the title compound as a sticky foam (131 mg, 96%): δ$_H$ (500 MHz, $d_4$-MeOH) 3.34-3.39 (m, 2H, $CH_2CH_2NSO_2$), 3.42-3.46 (m, 2H, $CH_2CH_2NSO_2$), 3.81 (s, 3H, $CH_3$), 3.84 (s, 3H, $CH_3$), 4.30 (s, 2H, $CH_2Ph$), 4.55 (s, 2H, $CH_2Im$), 6.53 (d, J=9.0 Hz, 2H, 2 CH (Ar)), 7.15 (s, 1H, CH (Im)), 7.34-7.38 (m, 5H, 5 CH (Ph)), 7.76-7.79 (m, 3H, 2 CH (Ar), CH (Im)), 7.82 (s, 1H, CH (Im)), 8.87 (s, 1H, CH (Im)); $\delta_C$ (125 MHz, $d_4$-MeOH) 34.3, 34.4, 45.0, 46.5, 51.2, 55.2, 112.8, 119.3, 120.3, 126.8, 129.3, 129.9 (2 CH), 132.7, 133.1, 137.7, 137.9, 139.1, 141.5, 152.0, 170.1; HRMS (ES+) calcd for $[C_{25}H_{28}N_6O_4S+H]$ 509.1971. found 509.1953; HPLC (I) $t_R$=11.24 min (100%), (II) $t_R$=15.21 min (100%).

4-[{2-[Benzyl-(1-methyl-1H-imidazole-4-sulfonyl)-amino]-ethyl}-(1-methyl-1H-imidazol-4-ylmethyl)-amino]-benzamide (12, CCB2277)

To a solution of acid 11 (50 mg, 0.0984 mmol, 1 equiv), $NH_4Cl$ (10.5 mg, 0.197 mmol, 2 equiv) and DIPEA (34 L) in DMF (1 mL) was added HBTU (48.5 mg, 0.128 mmol, 1.3 equiv). The reaction mixture was stirred for 1 h, after which time TLC indicated the reaction was complete. Water (25 mL) was added, and then the crude product was extracted into EtOAc (5×5 mL). The EtOAc extractions were combined, washed with water (3×5 mL), brine (5 mL), dried ($Na_2SO_4$), filtered and concentrated. The residue was dry-loaded onto silica gel, then flash chromatographed (eluent $CH_2Cl_2$/MeOH/$NH_4OH$, 92:7:1) to furnish primary amide 12 as a white powder (44 mg, 89%): $\delta_H$ (500 MHz, $CDCl_3$) 3.15 (m, 2H, (Bn)$NCH_2CH_2N$), 3.31 (m, 2H, (Bn)$NCH_2CH_2N$), 3.41 (s, 3H, $CH_3$ (Im)), 3.71 (s, 3H, $CH_3$ (Im)), 4.23 (s, 2H, $CH_2Ph$), 4.29 (s, 2H, $CH_2Im$), 6.02 (br, 2H, $NH_2$), 6.42 (d, J=9.0 Hz, 2H, 2 CH (Ar)), 6.66 (s, 1H, CH (Im)), 7.29-7.34 (m, 6H, 5 CH (Ph), CH (Im)), 7.41 (s, 1H, CH (Im)), 7.45 (s, 1H, CH (Im)), 7.56 (d, J=9.0 Hz, 2H, 2 CH (Ar)); $\delta_C$ (125 MHz, $CDCl_3$) δ1.3, 33.7, 43.9, 44.8, 49.4, 50.2, 54.0, 111.1, 121.0, 124.2, 127.2, 127.9, 128.4, 128.6, 128.9, 136.0, 138.4, 138.8, 138.9, 149.8, 168.9; HRMS (ES+) calcd for $[C_{25}H_{29}N_7O_3S+H]$ 508.2137. found 508.2131; HPLC (I) $t_R$=11.72 min (100%), (II) $t_R$=16.29 min (100%).

[N-Benzyl, N-{2-[(biphenyl-4-yl)-(3-methyl-3H-imidazol-4-ylmethyl)-amino]-ethyl}]1-methyl-1H-imidazole-4-sulfonamide (13, CCB2263)

Previously reported 1-tert-butoxycarbonylamino-{2-[biphenyl-4-yl-(3-methyl-3H-imidazol-4-ylmethyl)-amino]}-ethane (compound 9a in reference 31b) (30 mg, 0.0739 mmol) was deprotected by stirring in a 1:1 mixture of TFA-$CH_2Cl_2$ (1 mL) for 30 minutes. After removal of all solvent in vacuo, the residue (23 mg, 0.0739 mmol) was sulfonylated with 1-methyl-1H-imidazole-4-sulfonyl chloride, but with 5 equiv of DIPEA. Generally, the appropriate sulfonyl chloride (1.2 equiv) was added to a solution of the amine (1 equiv) and DIPEA (2 equiv) in anhydrous $CH_3CN$ (0.1 M) at 0° C. The reaction was warmed to room temperature and stirred for 16 h, at which time the solvent was evaporated. The residue was re-dissolved in $CH_2Cl_2$, washed with 5% $NaHCO_3$, water, brine, dried ($Na_2SO_4$), filtered and concentrated. After the usual work-up, the residue was purified by silica gel flash column chromatography (eluent $CH_2Cl_2$/MeOH/$NH_4OH$, 92:7:1) to afford 1-methyl-1H-imidazole-4-sulfonic acid benzyl-[2-(biphenyl-4-ylamino)-ethyl]-amide as a colorless film (30 mg, 91%) Next, the secondary aniline of 1-methyl-1H-imidazole-4-sulfonic acid benzyl-[2-(biphenyl-4-ylamino)-ethyl]-amide (30 mg, 0.067 mmol, 1 equiv) was alkylated with the HCl salt of 5-chloromethyl-1-methyl-1H-imidazole. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% $NaHCO_3$ (×3), brine, dried ($Na_2SO_4$), filtered and concentrated. After the usual work-up, the crude material was dry-loaded onto silica gel and purified by flash column chromatography (eluent $CH_2Cl_2$/MeOH/$NH_4OH$, 92:7:1) to give 11 as a glassy film (24 mg, 65%): $\delta_H$ (500 MHz, $CDCl_3$) 3.16 (m, 2H, (Bn)$NCH_2CH_2N$), 3.33 (m, 2H, (Bn)$NCH_2CH_2N$), 3.44 (s, 3H, $CH_3$ (Im)), 3.75 (s, 3H, $CH_3$ (Im)), 4.27 (s, 2H, $CH_2Ph$), 4.38 (s, 2H, $CH_2Im$), 6.56 (d, J=9.0 Hz, 2H, 2 CH (Ar)), 6.79 (s, 1H, CH (Im)), 7.34-7.51 (m, 15H, 10 CH (Ph), 3 CH (Im), 2 CH (Ar)); $\delta_C$ (125 MHz, $CDCl_3$) δ1.9, 34.2, 44.9, 45.4, 50.0, 54.5, 113.5, 124.6, 126.4, 126.5, 128.1, 128.3 (2), 128.9, 129.0, 129.2, 129.4, 130.5, 136.8, 138.8, 139.3, 139.9, 141.1, 147.2; HRMS (ES+) calcd for $[C_{30}H_{32}N_6O_2S+H]$ 541.2380. found 541.2386; HPLC (I) $t_R$=13.01 min (100%), (II) $t_R$=20.24 min (100%).

N-(2-tert-Butoxycarbonylaminoethyl) 1-methyl-1H-imidazole-4-sulfonamide (14, SF-6-086)

Mono-N-Boc-ethylenediamine (5; 5 g, 31.2 mmol, 1 eq) was sulfonylated with 1-methyl-1H-imidazole-4-sulfonyl chloride (6.76 g, 37.4 mmol, 1.2 eq). The appropriate sulfonyl chloride (1.2 equiv) was added to a solution of the amine (1 equiv) and DIPEA (2 equiv) in anhydrous $CH_3CN$ (0.1 M) at 0° C. The reaction was warmed to room temperature and stirred for 16 h, at which time the solvent was evaporated. The residue was re-dissolved in $CH_2Cl_2$, washed with 5% $NaHCO_3$, water, brine, dried ($Na_2SO_4$), filtered and concentrated. After 16 h, the solvent was reduced and then the reaction mixture was dry-loaded onto silica gel and purified by flash column chromatography (eluent $CH_2Cl_2$/MeOH/$NH_4OH$, 1092:7:1) to give the title compound as a white powder (9 g, 95%): $\delta_H$ (500 MHz, $CD_2Cl_2$) 1.37 (s, 9H, $C(CH_3)_3$), 2.99 (t, J=5.8 Hz, 2H, $CH_2NHSO_2$), 3.11 (q, J=5.8 Hz, 2H, $CH_2NHBoc$), 3.71 (s, 3H, $CH_3$), 5.53 (s, 1H, $NHSO_2$), 5.68 (s, 1H, NHBoc), 7.48 (s, 1H, Im), 7.56 (s, 1H, Im); $\delta_C$ (125 MHz, $CD_2Cl_2$) 27.6, 33.5, 39.8, 42.6, 78.9, 124.0, 127.2, 139.2, 156.1; HRMS (ES+) calcd for $[C_{11}H_{20}N_4O_4S+H]$ 305.1284. found 305.1294.

[N-(2-tert-Butoxycarbonylaminoethyl), N-{N-(2-pyrimidinyl)-piperidin-4-ylmethyl}]1-methyl-1H-imidazole-4-sulfonamide (15, SF-6-103)

N-(2-tert-Butoxycarbonylaminoethyl) 1-methyl-1H-imidazole-4-sulfonamide (5.94 g, 19.5 mmol, 1 eq) was chemoselectively alkylated on the sulfonamide NH with N-(2-pyrimidinyl)-piperidin-4-ylmethyl bromide (6 g, 23.4 mmol, 1.2 eq), but the reaction was stirred for 4 d at room temperature. To a solution of the sulfonamide (1 equiv) and $Cs_2CO_3$ (2 equiv) in DMF (0.1 M) at 0° C. was added the appropriate alkyl bromide or chloride (1.1 equiv). The resulting mixture was stirred at room temperature overnight. The reaction was diluted with water, then extracted into EtOAc (×3). The combined EtOAc extractions were washed with 5% $NaHCO_3$ (×3), brine, dried ($Na_2SO_4$), filtered and concentrated. [N-(2-Pyrimidinyl)-piperidin-4-ylmethyl bromide was made from the reaction of N-(2-pyrimidinyl)-piperidin-4-ylmethyl alcohol (5 g, 25.9 mmol, 1 eq) with PPh₃Br₂ (14.2 g, 33.7 mmol, 1.3 eq) in CH₂Cl₂ (130 mL) at 0° C. to room temperature over 6 h. At this point, the reaction was complete. Water (100 mL) was added to quench, then the CH₂Cl₂ layer was diluted further (500 mL total volume). The organic layer was collected, and the aqueous layer was extracted twice further (2×50 mL). The organic layers were collected, dried (Na₂SO₄), filtered and concentrated. The residue was re-dissolved in CH₂Cl₂, dry-loaded onto silica gel, then purified by flash column chromatography (eluent Hex/EtOAc, 7:1) to furnish N-(2-pyrimidinyl)-piperidin-4-ylmethyl bromide as a white powder (6.04 g, 91%).] After work-up, the crude material was dry-loaded onto silica gel, and purified by silica gel flash column chromatography (eluent CH₂Cl₂/MeOH/NH₄OH, 192:7:1), affording the title compound as a white solid (8.81 g, 94%): $\delta_H$ (500 MHz, CDCl₃) 1.09 (qd, J=12.3, 4.0 Hz, 2H, 2 CH (piperidinylmethyl)), 1.36 (s, 9H, C(CH₃)₃), 1.69-1.78 (m, 2H, 2 CH (piperidinylmethyl)), 1.84-1.92 (m, 1H, CH (piperidinylmethyl)), 2.77-2.83 (m, 2H, 2 CH (piperidinylmethyl)), 2.97 (br d, J=8.0 Hz, 2H, 2 CH (piperidinylmethyl)), 3.25-3.34 (m, 4H, CH₂CH₂NHBoc), 3.67 (s, 3H, CH₃), 4.64-4.69 (m, 2H, 2 CH (piperidinylmethyl)), 5.53 (m, 1H, NHBoc), 6.34 (t, J=4.9 Hz, 1H, CH (pyrimidine)), 7.36 (s, 1H, CH (Im)), 7.40 (s, 1H, CH (Im)), 8.20 (t, J=4.9 Hz, 2H, 2 CH (pyrimidine)); $\delta_C$ (125 MHz, CDCl₃) 28.3, 29.4, 34.8, 35.4, 39.6, 43.4, 49.1, 55.2, 79.0, 109.2, 124.2, 138.9, 140.6, 155.9, 157.5, 161.4; HRMS (ES+) calcd for [C₂₁H₃₃N₇O₄S+H] 480.2393. found 480.2409.

[N-(2-Aminoethyl), N-{N-(2-pyrimidinyl)-piperidin-4-ylmethyl}]1-methyl-1H-imidazole-4-sulfonamide (16, SF-6-127)

To a cooled (0° C.), stirring solution of 15/SF-6-103 (8.67 g, 18.1 mmol) in CH₂Cl₂ (50 mL) was added TFA (50 mL). After 5 min, the reaction was removed from the ice bath and allowed to stir for 1 h at room temperature, then all solvents were evaporated. The residue was re-dissolved in CH₂Cl₂ and the minimal required volume of MeOH, then dry-loaded onto silica gel and purified by flash column chromatography (eluent CH₂Cl₂/MeOH/NH₄OH, 92:7:1) to give 16 as a white, sticky foam (7.2 g, 100%): $\delta_H$ (500 MHz, CDCl₃) 1.10 (qd, J=12.2, 4.0 Hz, 2H, 2 CH (piperidinylmethyl)), 1.73-1.78 (m, 2H, 2 CH (piperidinylmethyl)), 1.87-1.95 (m, 1H, CH (piperidinyl)), 2.77-2.83 (m, 2H, 2 CH (piperidinylmethyl)), 2.92 (t, J=6.5 Hz, 2H, CH₂NH₂) 3.00 (br d, J=7.5 Hz, 2H, 2 CH (piperidinylmethyl)), 3.32 (t, J=6.4 Hz, 2H, CH₂CH₂NH₂), 3.46-3.51 (br s, NH₂), 3.69 (s, 3H, CH₃ (Im)), 4.66-4.72 (m, 2H, 2 CH (piperidinylmethyl)), 6.38 (t, J=4.7 Hz, 1H, CH (pyrimidine)), 7.40 (s, 1H, CH (Im)), 7.47 (s, 1H, CH (Im)), 8.22 (t, J=4.7 Hz, 2H, 2 CH (pyrimidine)); $\delta_C$ (125 MHz, CDCl₃) 29.5, 33.8, 35.5, 40.1, 43.4, 52.5, 54.9, 109.2, 124.2, 139.0, 139.4, 158.5, 161.5; HRMS (ES+) calcd for [C₁₆H₂₅N₇O₂S+H] 380.1869. found 380.1886.

[N-{2-(2-Chloro-4-cyanophenyl)-aminoethyl}, N-{N-(2-pyrimidinyl)-piperidin-4-ylmethyl}]1-methyl-1H-imidazole-4-sulfonamide (17a, SF-7-037)

Compound 16 was reacted with 2-chloro-4-fluorobenzonitrile on a 0.338 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H₂O was added, and the crude product was extracted with EtOAc (×3). The EtOAc extractions were combined, washed with water (×3), brine, dried (Na₂SO₄), filtered and concentrated. After the usual work-up, the crude material was purified by silica gel flash column chromatography (eluent CH₂Cl₂/MeOH/NH₄OH, 192:7:1) to give the title compound as a colourless, viscous oil (158 mg, 91%): $\delta_H$ (500 MHz, CDCl₃) 1.08 (qd, J=12.3, 4.0 Hz, 2H, 2 CH (piperidinylmethyl)), 1.68-1.74 (m, 2H, 2 CH (piperidinylmethyl)), 1.77-1.86 (m, 1H, CH (piperidinylmethyl)), 2.72 (td, J=12.5, 2.5 Hz, 2H, 2 CH (piperidinylmethyl)), 3.00 (br d, J=7.5 Hz, 2H, 2 CH (piperidinylmethyl)), 3.48-3.55 (m, 4H, CH₂CH₂NHAr), 3.71 (m, 3H, CH₃ (Im)), 4.63-4.69 (m, 2H, 2 CH (piperidinylmethyl)), 5.77 (t, J=5.3 Hz, 1H, CH₂NHAr), 6.40 (t, J=4.7 Hz, 1H, CH (pyrimidine)), 6.66 (d, J=8.5 Hz, 1H, CH (Ar)), 7.37 (dd, J=8.5, 2.0 Hz, 1H, CH (Ar)), 7.43 (s, 1H, CH (Im)), 7.45 (d, J=2.0 Hz, 1H, CH (Ar)), 7.46 (s, 1H, CH (Im)), 8.22 (t, J=4.7 Hz, 2H, 2 CH (pyrimidine)); $\delta_C$ (125 MHz, CDCl₃) 29.6, 33.9, 36.0, 42.2, 43.4, 48.7, 56.1, 98.7, 109.4, 110.0, 118.6, 119.0, 124.4, 132.4, 132.5, 139.1, 139.5, 147.0, 157.5, 161.4; HRMS (ES+) calcd for [C₂₃H₂₇N₈O₂SCl+H] 515.1744. found 515.1754.

N-(2-(2-Cyanopyridin-5-ylamino)ethyl)-1-methyl-N-((1-(pyrimidin-2-yl)piperidin-4-yl)methyl)-1H-imidazole-4-sulfonamide (17b)

Compound 16 was reacted with 2-cyano-5-fluoropyridine on a 0.791 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H₂O was added, and the crude product was extracted with EtOAc (×3). The EtOAc extractions were combined, washed with water (×3), brine, dried (Na₂SO₄), filtered and concentrated. After the usual work-up, the crude material was purified by silica gel flash column chromatography (eluent CH₂Cl₂/MeOH/NH₄OH, 192:7:1) to give the title compound as a colourless, viscous oil (320 mg, 84%): $\delta_H$ (500 MHz, CDCl₃) 0.95 (qd, J=12.3, 4.0 Hz, 2H, 2 CH (piperidinylmethyl)), 1.63-1.71 (m, 2H, 2 CH (piperidinylmethyl)), 1.74-1.83 (m, 1H, CH (piperidinylmethyl)), 2.72 (td, J=12.5, 2.5 Hz, 2H, 2 CH (piperidinylmethyl)), 2.93 (br d, J=7.5 Hz, 2H, 2 CH (piperidinylmethyl)), 3.23-3.27 (m, 2H, CH₂CH₂NHAr), 3.34-3.36 (m, 2H, CH₂CH₂NHAr), 3.65 (m, 3H, CH₃ (Im)), 4.55-4.59 (m, 2H, 2 CH (piperidinylmethyl)), 6.54 (m, 1H, CH₂NHAr), 6.96 (t, J=4.9 Hz, 1H, CH (pyrimidine)), 7.04 (m, 1H, CH (Ar)), 7.62 (s, 1H, CH (Im)), 7.77-7.78 (m, 2H, CH (Im); CH (Ar)), 8.02 (m, 1H, CH (Ar)), 8.28 (t, J=4.9 Hz, 2H, 2 CH (pyrimidine)); $\delta_C$ (125 MHz, DMSO-d₆) 28.96, 33.34, 34.88, 40.33, 41.20, 43.03, 47.87, 54.82, 109.46, 117.39, 118.92, 124.99, 129.69, 136.90, 137.56, 139.75, 146.98, 157.72, 161.02; HRMS (ES+) calcd for [C₂₂H₂₇N₉O₂S+H] 482.2087. found 482.2086.

[N-{2-(5-Bromopyridin-2-yl)-aminoethyl}, N-{N-(2-pyrimidinyl)-piperidin-4-ylmethyl}]1-methyl-1H-imidazole-4-sulfonamide (17c, SF-7-060)

Compound 16 was reacted with 5-bromo-2-fluoropyridine on a 0.512 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H₂O was added, and the crude product was extracted with EtOAc (×3). The EtOAc extractions were combined, washed with water (×3), brine, dried (Na₂SO₄), filtered and concentrated. After the usual work-up, the crude material was purified by silica gel flash column chromatography (eluent CH₂Cl₂/MeOH/NH₄OH, 192:7:1) to give the title compound as a colourless, viscous oil (200 mg, 73%): δ$_H$ (500 MHz, CDCl$_3$) 1.11 (qd, J=12.3, 4.0 Hz, 2H, 2 CH (piperidinylmethyl)), 1.72-1.78 (m, 2H, 2 CH (piperidinylmethyl)), 1.87-1.97 (m, 1H, CH (piperidinylmethyl)), 2.78 (td, J=12.8, 2.5 Hz, 2H, 2 CH (piperidinylmethyl)), 3.03 (br d, J=8.0 Hz, 2H, 2 CH (piperidinylmethyl)), 3.49-3.57 (m, 4H, CH$_2$CH$_2$NHAr), 3.72 (m, 3H, CH$_3$ (Im)), 4.67-4.73 (m, 2H, 2 CH (piperidinylmethyl)), 5.62 (t, J=5.3 Hz, 1H, CH$_2$NHAr), 6.34 (dd, J=9.0 Hz, 1H, CH (Ar)), 6.41 (t, J=4.9 Hz, 1H, CH (pyrimidine)), 7.40 (dd, J=9.0, 2.5 Hz, 1H, CH (Ar)), 7.42 (s, 1H, CH (Im)), 7.47 (s, 1H, CH (Im)), 8.05 (d, J=2.5 Hz, 1H, CH (Ar)), 8.25 (t, J=4.9 Hz, 2H, 2 CH (pyrimidine)); δ$_C$ (125 MHz, CDCl$_3$) 29.7, 33.9, 35.6, 40.5, 43.6, 48.5, 55.0, 106.8, 109.3, 109.7, 124.4, 138.9, 139.3, 140.0, 148.4, 156.9, 157.6, 161.5; HRMS (ES+) calcd for [C$_{21}$H$_{27}$N$_8$O$_2$SBr+H] 535.1239. found 535.1259.

[N-{2-(5-Bromopyrimidin-2-yl)-aminoethyl}, N-{N-(2-pyrimidinyl)-piperidin-4-ylmethyl}]1-methyl-1H-imidazole-4-sulfonamide (17d, SF-7-063)

Compound 16 was reacted with 5-bromo-2-fluoropyrimidine on a 0.528 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H$_2$O was added, and the crude product was extracted with EtOAc (×3). The EtOAc extractions were combined, washed with water (×3), brine, dried (Na$_2$SO$_4$), filtered and concentrated. After the usual work-up, the crude material was purified by silica gel flash column chromatography (eluent CH$_2$Cl$_2$/MeOH/NH$_4$OH, 192:7:1) to give the title compound as a white foam (255 mg, 90%): δ$_H$ (500 MHz, CDCl$_3$) 1.08 (qd, J=12.3, 4.0 Hz, 2H, 2 CH (piperidinylmethyl)), 1.70-1.77 (m, 2H, 2 CH (piperidinylmethyl)), 1.83-1.92 (m, 1H, CH (piperidinylmethyl)), 2.78 (td, J=12.8, 2.5 Hz, 2H, 2 CH (piperidinylmethyl)), 3.03 (br d, J=8.0 Hz, 2H, 2 CH (piperidinylmethyl)), 3.43 (t, J=6.3 Hz, 2H, CH$_2$CH$_2$NHAr), 3.57 (t, J=6.3 Hz, 2H, CH$_2$CH$_2$NHAr), 3.68 (m, 3H, CH$_3$ (Im)), 4.60-4.66 (m, 2H, 2 CH (piperidinylmethyl)), 6.39 (t, J=4.6 Hz, 1H, CH (pyrimidine)), 7.40 (s, 1H, CH (Im)), 7.47 (s, 1H, CH (Im)), 8.19 (s, 2H, 2 CH (Ar)), 8.21 (t, J=4.6 Hz, 2H, 2 CH (pyrimidine)); δ$_C$ (125 MHz, CDCl$_3$) 29.5, 33.8, 35.5, 40.4, 43.6, 48.3, 55.0, 106.1, 109.3, 124.3, 139.1, 139.6, 157.6, 158.1, 160.3, 161.3; HRMS (ES+) calcd for [C$_{20}$H$_{26}$N$_9$O$_2$SBr+H] 536.1192. found 536.1213.

[N-{2-(3-Fluoro-4-cyanophenyl)-aminoethyl}, N-{N-(2-pyrimidinyl)-piperidin-4-ylmethyl}]1-methyl-1H-imidazole-4-sulfonamide (17e, SF-7-051)

Compound 16 was reacted with 2,4-difluorobenzonitrile on a 0.417 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H$_2$O was added, and the crude product was extracted with EtOAc (×3). The EtOAc extractions were combined, washed with water (×3), brine, dried (Na$_2$SO$_4$), filtered and concentrated. This resulted in a separable mixture of the two expected isomers. After the usual work-up, the crude material was purified by prepTLC (eluent CH$_2$Cl$_2$/MeOH/NH$_4$OH, 92:7:1) to give the title compound as a white foam (99 mg, 48%): δ$_H$ (500 MHz, CDCl$_3$) 1.15 (qd, J=12.5, 4.0 Hz, 2H, 2 CH (piperidinylmethyl)), 1.73-1.79 (m, 2H, 2 CH (piperidinylmethyl)), 1.87-1.95 (m, 1H, CH (piperidinylmethyl)), 2.80 (td, J=12.8, 2.5 Hz, 2H, 2 CH (piperidinylmethyl)), 3.03 (br d, J=7.5 Hz, 2H, 2 CH (piperidinylmethyl)), 3.36 (q, J=5.5 Hz, 2H, CH$_2$CH$_2$NHAr), 3.65 (t, J=5.8 Hz, 2H, CH$_2$CH$_2$NHAr), 3.77 (m, 3H, CH$_3$ (Im)), 4.70-4.75 (m, 2H, 2 CH (piperidinylmethyl)), 6.10-6.13 (m, 1H, CH$_2$NHAr), 6.30 (dd, J=12.0, 2.0 Hz, 1H, CH (Ar)), 6.39 (dd, J=8.8, 2.0 Hz, 1H, CH (Ar)), 6.44 (t, J=4.9 Hz, 1H, CH (pyrimidine)), 7.32 (dd, J=8.8, 7.3 Hz, 1H, CH (Ar)), 7.47 (s, 1H, CH (Im)), 7.52 (s, 1H, CH (Im)), 8.27 (t, J=4.9 Hz, 2H, CH (pyrimidine)); δ$_C$ (125 MHz, CDCl$_3$) 29.5, 34.0, 35.5, 41.5, 43.5, 47.7, 54.4, 87.0 (d, J$_{CF}$=15.5 Hz), 98.1 (d, J$_{CF}$=22.8 Hz), 108.8 (br), 109.4, 115.7, 124.6, 133.9 (d, J$_{CF}$=2.75 Hz), 139.0, 139.6, 153.4 (d, J$_{CF}$=10.9 Hz), 157.6, 161.5, 165.0 (d, J$_{CF}$=252 Hz); HRMS (ES+) calcd for [C$_{23}$H$_{27}$N$_8$O$_2$FS+H] 499.2040. found 499.2057.

[N-{2-(2-Fluoro-4-cyanophenyl)-aminoethyl}, N-{N-(2-pyrimidinyl)-piperidin-4-ylmethyl}]1-methyl-1H-imidazole-4-sulfonamide (17f SF-7-041)

Compound 16 was reacted with 3,4-difluorobenzonitrile on a 0.343 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H$_2$O was added, and the crude product was extracted with EtOAc (×3). The EtOAc extractions were combined, washed with water (×3), brine, dried (Na$_2$SO$_4$), filtered and concentrated. After the usual work-up, the crude material was purified by silica gel flash column chromatography (eluent CH$_2$Cl$_2$/MeOH/NH$_4$OH, 192:7:1) to give the title compound as a white foam (138 mg, 82%): δ$_H$ (500 MHz, CDCl$_3$) 1.13 (qd, J=12.3, 4.0 Hz, 2H, 2 CH (piperidinylmethyl)), 1.73-1.78 (m, 2H, 2 CH (piperidinylmethyl)), 1.83-1.91 (m, 1H, CH (piperidinylmethyl)), 2.78 (td, J=12.8, 2.5 Hz, 2H, 2 CH (piperidinylmethyl)), 3.04 (br d, J=7.5 Hz, 2H, 2 CH (piperidinylmethyl)), 3.51 (q, J=5.7 Hz, 2H, CH$_2$CH$_2$NHAr), 3.59 (t, J=6.0 Hz, 2H, CH$_2$CH$_2$NHAr), 3.75 (m, 3H, CH$_3$ (Im)), 4.69-4.75 (m, 2H, 2 CH (piperidinylmethyl)), 5.74-5.78 (m, 1H, CH$_2$NHAr), 6.43 (t, J=4.7 Hz, 1H, CH (pyrimidine)), 6.68 (t, J=8.5 Hz, 1H, CH (Ar)), 7.19 (dd, J=11.5, 1.5 Hz, 1H, CH (Ar)), 7.31 (br dd, J=8.5, 1.5 Hz, 1H, CH (Ar)), 7.44 (s, 1H, CH (Im)), 7.49 (s, 1H, CH (Im)), 8.27 (t, J=4.7 Hz, 2H, 2 CH (pyrimidine)); δ$_C$ (125 MHz, CDCl$_3$) 29.5, 33.9, 35.7, 41.6, 43.4, 48.3, 55.1, 97.4 (d, J$_{CF}$=9.13 Hz), 109.4, 110.8 (d, J$_{CF}$=4.5 Hz), 117.5 (d, J$_{CF}$=21.9 Hz), 119.2 (d, J$_{CF}$=2.75 Hz), 124.3, 130.1 (d, J$_{CF}$=2.75 Hz), 139.1, 139.6, 140.5 (d, J$_{CF}$=11.9 Hz), 149.8 (d, J$_{CF}$=241 Hz), 157.6, 161.4; HRMS (ES+) calcd for [C$_{23}$H$_{27}$N$_8$O$_2$FS+H] 499.2040. found 499.2055.

[N-{2-(2,6-Difluoro-4-cyanophenyl)-aminoethyl}, N-{N-(2-pyrimidinyl)-piperidin-4-ylmethyl}]1-methyl-1H-imidazole-4-sulfonamide (17g, SF-7-035)

Compound 16 was reacted with 3,4,5-trifluorobenzonitrile on a 0.359 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H$_2$O was added, and the crude product was extracted with EtOAc (×3). The EtOAc extractions were combined, washed with water (×3), brine, dried (Na$_2$SO$_4$), filtered and concentrated. After the usual work-up, the crude material was purified by silica gel flash column chromatography (eluent CH$_2$Cl$_2$/MeOH/NH$_4$OH, 192:7:1) to give the title compound as a white foam (179 mg, 97%): δ$_H$ (500 MHz, CDCl$_3$) 1.09 (qd, J=12.3, 4.0 Hz, 2H, 2 CH (piperidinylmethyl)), 1.68-1.75

(m, 2H, 2 CH (piperidinylmethyl)), 1.81-1.90 (m, 1H, CH (piperidinylmethyl)), 2.75 (td, J=12.5, 2.5 Hz, 2H, 2 CH (piperidinylmethyl)), 2.98 (br d, J=7.0 Hz, 2H, 2 CH (piperidinylmethyl)), 3.51 (t, J=5.8 Hz, 2H, $CH_2CH_2NHAr$), 3.72 (m, 5H, $CH_2CH_2NHAr$, $CH_3$ (Im)), 4.65-4.73 (m, 2H, 2 CH (piperidinylmethyl)), 5.67 (m, 1H, $CH_2NHAr$), 6.40 (t, J=4.9 Hz, 1H, CH (pyrimidine)), 7.05 (dd, J=7.5, 2.5 Hz, 2H, CH (Ar)), 7.43 (s, 1H, CH (Im)), 7.47 (s, 1H, CH (Im)), 8.23 (t, J=4.9 Hz, 2H, 2 CH (pyrimidine)); $\delta_C$ (125 MHz, $CDCl_3$) 29.6, 33.9, 35.7, 43.5, 43.7, 50.2, 55.4, 96.7 (t, $J_{CF}$=11.4 Hz), 109.3, 115.8 (dd, $J_{CF}$=18.3, 8.13 Hz), 117.9 (t, $J_{CF}$=3.19 Hz), 124.4, 130.8 (t, $J_{CF}$=12.3 Hz), 139.0, 139.7, 150.8 (dd, $J_{CF}$=241, 10.0 Hz), 157.5, 161.4; HRMS (ES+) calcd for $[C_{23}H_{26}N_8O_2F_2S+H]$ 517.1946. found 517.1953.

[N-{2-(2,3,5,6-Tetrafluoro-4-cyanophenyl)-aminoethyl}, N-{N-(2-pyrimidinyl)-piperidin-4-ylmethyl}] 1-methyl-1H-imidazole-4-sulfonamide (17h, SF-7-042)

Compound 16 was reacted with 2-chloro-4-fluorobenoznitrile on a 0.338 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, $H_2O$ was added, and the crude product was extracted with EtOAc (×3). The EtOAc extractions were combined, washed with water (×3), brine, dried ($Na_2SO_4$), filtered and concentrated. The reaction was complete within 12 h at room temperature. After the usual work-up, the crude material was purified by silica gel flash column chromatography (eluent $CH_2Cl_2$/MeOH/$NH_4OH$, 192:7:1) to give the title compound as a white foam (158 mg, 85%): $\delta_H$ (500 MHz, $CDCl_3$) 1.13 (qd, J=12.2, 4.0 Hz, 2H, 2 CH (piperidinylmethyl)), 1.72-1.79 (m, 2H, 2 CH (piperidinylmethyl)), 1.88-1.97 (m, 1H, CH (piperidinylmethyl)), 2.81 (td, J=12.8, 2.5 Hz, 2H, 2 CH (piperidinylmethyl)), 2.97 (br d, J=7.0 Hz, 2H, 2 CH (piperidinylmethyl)), 3.63 (t, J=5.0 Hz, 2H, $CH_2CH_2NHAr$), 3.77 (s, 3H, $CH_3$ (Im)), 3.78-3.84 (m, 2H, $CH_2CH_2NHAr$), 4.71-4.77 (m, 2H, 2 CH (piperidinylmethyl)), 6.44 (t, J=4.8 Hz, 1H, CH (pyrimidine)), 6.81-6.86 (m, 1H, $CH_2NHAr$), 7.47 (s, 1H, CH (Im)), 7.51 (s, 1H, CH (Im)), 8.27 (t, J=4.8 Hz, 2H, CH (pyrimidine)); $\delta_C$ (125 MHz, $CDCl_3$) 29.7, 34.1, 35.9, 43.4, 43.5, 50.2, 55.0, 78.4 (t, $J_{CF}$=18.3 Hz), 109.0 (m), 109.5, 124.7, 133.5 (m), 135.9 (dm), 139.0, 140.1, 148.1 (dm), 157.7, 161.6; HRMS (ES+) calcd for $[C_{23}H_{24}N_8O_2F_4S+H]$ 553.1757. found 553.1774.

[N-{2-[(2-Chloro-4-cyanophenyl)-(3-methyl-3H-imidazol-4-ylmethyl)-amino]-ethyl}, N-{N-(2-pyrimidinyl)-piperidin-4-ylmethyl}]1-methyl-1H-imidazole-4-sulfonamide (18a, SF-7-065)

Compound 17a was alkylated on a 0.068 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% $NaHCO_3$ (×3), brine, dried ($Na_2SO_4$), filtered and concentrated. After the usual work-up, the crude material was purified by silica gel flash column chromatography (eluent $CH_2Cl_2$/MeOH/$NH_4OH$, 192:7:1) to afford the title compound as a white foam (37 mg, 90%): $\delta_H$ (500 MHz, $CDCl_3$) 1.04 (qd, J=12.2, 4.0 Hz, 2H, 2 CH (piperidinylmethyl)), 1.63-1.68 (m, 2H, 2 CH (piperidinylmethyl)), 1.70-1.76 (m, 1H, CH (piperidinylmethyl)), 2.76 (td, J=12.5, 2.5 Hz, 2H, 2 CH (piperidinylmethyl)), 2.94 (br d, J=7.0 Hz, 2H, 2 CH (piperidinylmethyl)), 3.31-3.36 (m, 2H, $SO_2NCH_2CH_2N$), 3.39-3.44 (m, 2H, $SO_2NCH_2CH_2N$), 3.51 (s, 3H, $CH_3$ (Im)), 3.73 (m, 3H, $CH_3$ (Im)), 4.41 (s, 2H, $CH_2Im$), 4.65-4.71 (m, 2H, 2 CH (piperidinylmethyl)), 6.42 (t, J=4.9 Hz, 1H, CH (pyrimidine)), 6.97 (s, 1H, CH (Im)), 7.23 (d, J=8.5 Hz, 1H, CH (Ar)), 7.36 (s, 1H, CH (Im)), 7.41 (s, 1H, CH (Im)), 7.43 (s, 1H, CH (Im)), 7.48 (dd, J=8.5, 2.0 Hz, 1H, CH (Ar)), 7.63 (d, J=2.0 Hz, 1H, CH (Ar)), 8.26 (t, J=4.9 Hz, 2H, 2 CH (pyrimidine)); $\delta_C$ (125 MHz, $CDCl_3$) 29.6, 31.7, 33.9, 36.0, 43.5, 45.7, 47.1, 50.7, 55.6, 107.1, 109.4, 117.6, 123.7, 124.1, 126.6, 129.0, 129.9, 131.4, 134.3, 138.9, 139.0, 139.7, 151.0, 157.6, 161.5; HRMS (ES+) calcd for $[C_{28}H_{33}N_{10}O_2SCl+H]$ 609.2275. found 609.2296; HPLC (I) $t_R$=12.90 min (99.13%), (II) $t_R$=19.65 min (98.61%).

N-(2-β2-Cyanopyridin-5-yl)((1-methyl-1H-imidazol-5-yl)methyl)amino)ethyl)-1-methyl-N-((1-(pyrimidin-2-yl)piperidin-4-yl)methyl)-1H-imidazole-4-sulfonamide (18b)

Compound 17b was alkylated on a 0.415 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% $NaHCO_3$ (×3), brine, dried ($Na_2SO_4$), filtered and concentrated. After the usual work-up, the crude material was purified by silica gel flash column chromatography (eluent $CH_2Cl_2$/MeOH/$NH_4OH$, 192:7:1) to afford the title compound as a white foam (186 mg, 78%): $\delta_H$ (500 MHz, DMSO-$d_6$) 1.05-1.13 (m, 4H, 4 CH (piperidinylmethyl)), 1.69-1.74 (m, 1H, CH (piperidinylmethyl)), 2.79 (td, J=12.5, 2.5 Hz, 2H, 2 CH (piperidinylmethyl)), 2.95 (br d, J=7.0 Hz, 2H, 2 CH (piperidinylmethyl)), 3.28 (s, 3H, $CH_3$ (Im)), 3.34-3.39 (m, 2H, $SO_2NCH_2CH_2N$), 3.41-3.42 (m, 2H, $SO_2NCH_2CH_2N$), 3.68 (s, 3H, $CH_3$ (Im)), 4.38 (s, 2H, $CH_2Im$), 4.60-4.64 (m, 2H, 2 CH (piperidinylmethyl)), 6.41 (t, J=4.8 Hz, 1H, CH (pyrimidine)), 6.86 (s, 1H, CH (Ar)), 7.02 (s, 1H, CH (Im)), 7.20 (m, 1H, CH (Ar)), 7.41-7.50 (m, 2H, CH (Im), CH (Ar)), 7.65 (s, 1H, CH (Im)), 7.80 (s, 1H, CH (Im)), 8.26 (t, J=4.9 Hz, 2H, 2 CH (pyrimidine)); $\delta_C$ (125 MHz, DMSO-$d_6$) 29.5, 32.0, 32.8, 34.0, 35.9, 43.5, 44.2, 48.9, 49.2, 49.4, 49.7, 53.2, 56.2, 109.5, 118.1, 120.8, 122.3, 124.6, 129.4, 135.8, 139.3, 145.5, 157.7, 161.4; HRMS (ES+) calcd for $[C_{27}H_{33}N_{11}O_2S+H]$ 576.2618. found 576.2617.

[N-{2-[(5-Cyanopyridin-2-yl)-(3-methyl-3H-imidazol-4-ylmethyl)-amino]-ethyl}, N-{N-(2-pyrimidinyl)-piperidin-4-ylmethyl}]1-methyl-1H-imidazole-4-sulfonamide (18c, SF-7-104)

Compound 17c was alkylated on a 0.178 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. After the usual work-up, the crude material was purified by silica gel flash column chromatography (eluent CH$_2$Cl$_2$/MeOH/NH$_4$OH, 192:7:1) to furnish [N-{2-[(5-bromopyridin-2-yl)-(3-methyl-3H-imidazol-4-ylmethyl)amino]ethyl}, N-{N-(2-pyrimidinyl)-piperidin-4-ylmethyl}]1-methyl-1H-imidazole-4-sulfonamide as a white foam (107 mg, 96%): $\delta_H$ (500 MHz, CDCl$_3$) 1.12 (qd, J=12.5, 4.0 Hz, 2H, 2 CH (piperidinylmethyl)), 1.72-1.80 (m, 3H, 3 CH (piperidinylmethyl)), 2.84 (td, J=13.0, 2.5 Hz, 2H, 2 CH (piperidinylmethyl)), 2.98 (br d, J=7.0 Hz, 2H, 2 CH (piperidinylmethyl)), 3.14-3.18 (m, 2H, NSO$_2$CH$_2$CH$_2$N), 3.55 (s, 3H, CH$_3$ (Im)), 3.62-3.67 (m, 2H, NSO$_2$CH$_2$CH$_2$N), 3.73 (m, 3H, CH$_3$ (Im)), 4.69-4.78 (m, 2H, 2 CH (piperidinylmethyl)), 4.80 (s, 2H, CH$_2$Im), 6.43 (t, J=4.9 Hz, 1H, CH (pyrimidine)), 6.69 (d, J=9.5 Hz, 1H, CH (Ar)), 6.96 (s, 1H, CH (Im)), 7.38 (s, 1H, CH (Im)), 7.43 (s, 1H, CH (Im)), 7.46 (s, 1H, CH (Im)), 7.55 (dd, J=9.0, 2.5 Hz, 1H, CH (Ar)), 8.15 (d, J=2.5 Hz, 1H, CH (Ar)), 8.27 (t, J=4.9 Hz, 2H, 2 CH (pyrimidine)); $\delta_C$ (125 MHz, CDCl$_3$) 29.6, 31.8, 33.9, 35.6, 41.0, 43.5, 46.2, 47.0, 55.9, 107.1, 107.6, 109.3, 124.2, 128.2, 129.1, 138.8, 138.9, 139.3, 140.1, 148.2, 155.9, 157.6, 161.5; HRMS (ES+) calcd for [C$_{26}$H$_{33}$N$_{10}$O$_2$SBr+H] 629.1770. found 629.1780; HPLC (I) $t_R$=12.78 min (100%), (II) $t_R$=18.88 min (100%). The aryl bromide was then converted to the corresponding aryl nitrile on a 0.115 mmol scale. A stirring solution of the aryl bromide (1 equiv) in DMF (0.1 M) was degassed, then Zn(CN)$_2$ (0.6 eq), Pd(PPh$_3$)$_4$ (0.1 eq), Zn dust (0.05 eq) and Zn(OAc)$_2$ (0.05 eq) were added. The mixture was heated to 120° C. for 2 h, after which time the reaction was allowed to cool, diluted with water and extracted into EtOAc (×3). The EtOAc extractions were combined and washed with 5% NaHCO$_3$ (×3), brine, dried (Na$_2$SO$_4$), filtered and concentrated. After work-up, the crude material was dry-loaded onto silica gel, and purified by flash column chromatography (eluent CH$_2$Cl$_2$/MeOH/NH$_4$OH, 192:7:1) to give 18c as a white foam (51 mg, 77%): $\delta_H$ (500 MHz, CDCl$_3$) 1.11 (qd, J=12.5, 4.0 Hz, 2H, 2 CH (piperidinylmethyl)), 1.67-1.77 (m, 3H, 3 CH (piperidinylmethyl)), 2.78-2.87 (m, 2H, 2 CH (piperidinylmethyl)), 2.93 (br d, J=7.0 Hz, 2H, 2 CH (piperidinylmethyl)), 3.15-3.22 (m, 2H, SO$_2$NCH$_2$CH$_2$N), 3.54 (s, 3H, CH$_3$ (Im)), 3.69-3.78 (m, 5H, SO$_2$NCH$_2$CH$_2$N, CH$_3$ (Im)), 4.68-4.76 (m, 2H, 2 CH (piperidinylmethyl)), 4.91 (s, 2H, CH$_2$Im), 6.43 (t, J=4.9 Hz, 1H, CH (pyrimidine)), 6.85 (d, J=9.5 Hz, 1H, CH (Ar)), 6.97 (s, 1H, CH (Im)), 7.39 (s, 1H, CH (Im)), 7.42 (s, 1H, CH (Im)), 7.43 (s, 1H, CH (Im)), 7.66 (dd, J=9.0, 2.5 Hz, 1H, CH (Ar)), 8.27 (t, J=4.9 Hz, 2H, 2 CH (pyrimidine)), 8.41 (d, J=2.5 Hz, 1H, CH (Ar)); $\delta_C$ (125 MHz, CDCl$_3$) 29.7, 31.9, 34.0, 35.7, 41.0 (br), 43.6, 46.3, 47.1, 56.0, 97.1, 106.1, 109.4, 118.3, 124.3, 127.3, 129.7, 139.0, 139.2, 139.4, 140.3, 152.4, 157.6, 158.5, 161.6; HRMS (ES+) calcd for [C$_{27}$H$_{33}$N$_{11}$O$_2$S+H] 576.2618. found 576.2628; HPLC (I) $t_R$=12.43 min (100%), (II) $t_R$=17.87 min (100%).

[N-{2-[(5-Cyanopyrimidin-2-yl)-(3-methyl-3H-imidazol-4-ylmethyl)-amino]-ethyl}, N-{N-(2-pyrimidinyl)-piperidin-4-ylmethyl}]1-methyl-1H-imidazole-4-sulfonamide (18d, SF-7-097)

Compound 17d was alkylated on a 0.187 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. This afforded [N-{2-[(5-bromopyrimidin-2-yl)-(3-methyl-3H-imidazol-4-ylmethyl)amino]ethyl}, N-{N-(2-pyrimidinyl)-piperidin-4-ylmethyl}]1-methyl-1H-imidazole-4-sulfonamide as a white foam (109 mg, 93%): $\delta_H$ (500 MHz, CDCl$_3$) 1.17 (qd, J=12.2, 4.0 Hz, 2H, 2 CH (piperidinylmethyl)), 1.78-1.84 (m, 2H, 2 CH (piperidinylmethyl)), 1.92-1.99 (m, 1H, CH (piperidinylmethyl)), 2.82 (td, J=12.8, 2.5 Hz, 2H, 2 CH (piperidinylmethyl)), 3.10 (br d, J=7.5 Hz, 2H, 2 CH (piperidinylmethyl)), 3.19-3.23 (m, 2H, SO$_2$NCH$_2$CH$_2$N), 3.58 (s, 3H, CH$_3$ (Im)), 3.71-3.75 (m, 5H, SO$_2$NCH$_2$CH$_2$N, CH$_3$ (Im)), 4.71-4.77 (m, 2H, 2 CH (piperidinylmethyl)), 4.89 (s, 2H, CH$_2$Im), 6.43 (t, J=4.9 Hz, 1H, CH (pyrimidine)), 7.05 (s, 1H, CH (Im)), 7.42 (s, 1H, CH (Im)), 7.43 (s, 1H, CH (Im)), 7.46 (s, 1H, CH (Im)), 8.28 (t, J=4.9 Hz, 2H, 2 CH (pyrimidine)) 8.30 (s, 2H, 2 CH (Ar)); $\delta_C$ (125 MHz, CDCl$_3$) 29.7, 31.9, 33.9, 35.6, 40.7, 43.7, 46.0, 46.2, 55.8, 106.4, 109.3, 124.4, 128.1, 129.5, 138.5, 138.9, 139.3, 157.6, 158.0, 159.3, 161.6; HRMS (ES+) calcd for [C$_{25}$H$_{32}$N$_{11}$O$_2$SBr+H] 630.1723. found 630.1748; HPLC (I) $t_R$=13.05 min (100%), (II) $t_R$=19.52 min (100%). The aryl bromide was then converted to the corresponding aryl nitrile on a 0.127 mmol scale. A stirring solution of the aryl bromide (1 equiv) in DMF (0.1 M) was degassed, then Zn(CN)$_2$ (0.6 eq), Pd(PPh$_3$)$_4$ (0.1 eq), Zn dust (0.05 eq) and Zn(OAc)$_2$ (0.05 eq) were added. The mixture was heated to 120° C. for 2 h, after which time the reaction was allowed to cool, diluted with water and extracted into EtOAc (×3). The EtOAc extractions were combined and washed with 5% NaHCO$_3$ (×3), brine, dried (Na$_2$SO$_4$), filtered and concentrated. After work-up, the crude material was dry-loaded onto silica gel, and purified by flash column chromatography (eluent CH$_2$Cl$_2$/MeOH/NH$_4$OH, 192:7:1) to give 18d as a white foam (50 mg, 69%): $\delta_H$ (500 MHz, CDCl$_3$) 1.16 (qd, J=12.2, 4.0 Hz, 2H, 2 CH (piperidinylmethyl)), 1.75-1.82 (m, 2H, 2 CH (piperidinylmethyl)), 1.86-1.94 (m, 1H, CH (piperidinylmethyl)), 2.80 (td, J=12.8, 2.5 Hz, 2H, 2 CH (piperidinylmethyl)), 3.07 (br d, J=7.5 Hz, 2H, 2 CH (piperidinylmethyl)), 3.26-3.30 (m, 2H, SO$_2$NCH$_2$CH$_2$N), 3.58 (s, 3H, CH$_3$ (Im)), 3.74 (s, 3H, CH$_3$ (Im)), 3.83-3.87 (m, 2H, SO$_2$NCH$_2$CH$_2$N), 4.70-4.76 (m, 2H, 2 CH (piperidinylmethyl)), 4.99 (s, 2H, CH$_2$Im), 6.44 (t, J=4.8 Hz, 1H, pyrimidine), 7.07 (s, 1H, CH (Im)), 7.39-7.44 (s, 3H, 3 CH (Im)), 8.28 (t, J=4.9 Hz, 2H, 2 CH (pyrimidine)), 8.54 (br s, 2H, 2 CH (Ar)); $\delta_C$ (125 MHz, CDCl$_3$) 29.7, 32.0, 34.0, 35.8, 40.9, 43.7, 46.3, 46.5, 55.9, 96.8, 109.5, 116.2, 124.5, 127.2, 129.8, 138.8, 139.0, 139.3, 157.7, 160.6, 161.0, 161.6; HRMS (ES+) calcd for [C$_{26}$H$_{32}$N$_{12}$O$_2$S+H] 577.2570. found 577.2569; HPLC (I) $t_R$=12.45 min (100%), (II) $t_R$=17.94 min (100%).

[N-{2-[(3-Fluoro-4-cyanophenyl)-(3-methyl-3H-imidazol-4-ylmethyl)-amino]-ethyl}, N-{N-(2-pyrimidinyl)-piperidin-4-ylmethyl}]1-methyl-1H-imidazole-4-sulfonamide (18e, SF-7-066)

Compound 17e was alkylated on a 0.0683 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added.

152.9 (d, $J_{CF}$=244 Hz), 157.6, 161.5; HRMS (ES+) calcd for [$C_{28}H_{33}N_{10}O_2FS$+H] 593.2571. found 593.2568; HPLC (I) $t_R$=12.75 min (100%), (II), $t_R$=19.09 (99.22%).

[N-{2-[(2,6-Difluoro-4-cyanophenyl)-(3-methyl-3H-imidazol-4-ylmethyl)-amino]-ethyl}, N-{N-(2-pyrimidinyl)-piperidin-4-ylmethyl}]1-methyl-1H-imidazole-4-sulfonamide (18g, SF-7-056)

Compound 17g was alkylated on a 0.068 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. After the usual work-up, the crude material was purified by silica gel flash column chromatography (eluent CH$_2$Cl$_2$/MeOH/NH$_4$OH, 192:7:1) to yield 18g as a white foam (40 mg, 97%): $\delta_H$ (500 MHz, CDCl$_3$) 1.06 (qd, J=12.3, 4.0 Hz, 2H, 2 CH (piperidinylmethyl)), 1.67-1.77 (m, 3H, 3 CH (piperidinylmethyl)), 2.78 (td, J=12.8, 2.5 Hz, 2H, 2 CH (piperidinylmethyl)), 2.96 (br d, J=6.5 Hz, 2H, 2 CH (piperidinylmethyl)), 3.26-3.30 (m, 2H, SO$_2$NCH$_2$CH$_2$N), 3.39-3.43 (m, 2H, SO$_2$NCH$_2$CH$_2$N), 3.57 (s, 3H, CH$_3$ (Im)), 3.73 (s, 3H, CH$_3$ (Im)), 4.38 (s, 2H, CH$_2$Im), 4.66-4.73 (m, 2H, 2 CH (piperidinylmethyl)), 6.42 (t, J=4.9 Hz, 1H, CH (pyrimidine)), 6.92 (s, 1H, CH (Im)), 7.12-7.17 (m, 2H, 2 CH (Ar)), 7.35 (s, 1H, CH (Im)), 7.40 (s, 1H, CH (Im)), 7.42 (s, 1H, CH (Im)), 8.26 (t, J=4.9 Hz, 2H, 2 CH (pyrimidine)); $\delta_C$ (125 MHz, CDCl$_3$) 29.6, 31.4, 33.9, 36.0, 43.5, 46.3 (t, $J_{CF}$=4.5 Hz), 47.8, 51.9 (t, $J_{CF}$=2.6 Hz), 55.6, 106.9 (t, $J_{CF}$=11.9 Hz), 109.4, 116.6 (m), 116.6 (t, $J_{CF}$=2.8 Hz), 124.1, 126.9, 129.9, 131.1 (t, J=13.3 Hz), 138.9, 139.2, 139.7, 157.6, 158.3 (dd, $J_{CF}$=249, 8.3 Hz), 161.5; HRMS (ES+) calcd for [$C_{28}H_{32}N_{10}O_2F_2S$+H] 611.2477. found 611.2494; HPLC (I) $t_R$=12.93 min (100%), (II) $t_R$=19.59 min (100%).

[N-{2-[(2,3,5,6-Tetrafluoro-4-cyanophenyl)-(3-methyl-3H-imidazol-4-ylmethyl)-amino]-ethyl}, N-{N-(2-pyrimidinyl)-piperidin-4-ylmethyl}]1-methyl-1H-imidazole-4-sulfonamide (18h, SF-7-069)

Compound 17h was alkylated on a 0.0688 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. After the usual work-up, the crude material was purified by silica gel flash column chromatography (eluent CH$_2$Cl$_2$/MeOH/NH$_4$OH, 192:7:1) to afford 18h as a white foam (28 mg, 63%): $\delta_H$ (500 MHz, CDCl$_3$) 1.08 (qd, J=12.2, 4.0 Hz, 2H, 2 CH (piperidinylmethyl)), 1.69-1.81 (m, 3H, 3 CH (piperidinylmethyl)), 2.80 (td, J=12.8, 2.5 Hz, 2H, 2 CH (piperidinylmethyl)), 2.96 (br d, J=7.5 Hz, 2H, 2 CH (piperidinylmethyl)), 3.34-3.40 (m, 2H, SO$_2$NCH$_2$CH$_2$N), 3.51-3.56 (m, 2H, SO$_2$NCH$_2$CH$_2$N), 3.57 (s, 3H, CH$_3$ (Im)), 3.74 (s, 3H, CH$_3$ (Im)), 4.53 (s, 2H, CH$_2$Im), 4.68-4.74 (m, 2H, 2 CH (piperidinylmethyl)), 6.43 (t, J=4.7 Hz, 1H, CH (pyrimidine)), 6.98 (s, 1H, CH (Im)), 7.38 (s, 1H, CH (Im)), 7.41-7.46 (m, 2H, 2 CH (Im)), 8.27 (t, J=4.7 Hz, 2H, CH (pyrimidine)); $\delta_C$ (125 MHz, CDCl$_3$) 29.6, 31.5, 33.9, 36.0, 43.5, 46.2, 47.9, 51.9 (m), 55.7, 86.9 (t, J$_{CF}$=17.4 Hz), 107.8 (m), 109.5, 124.2, 126.2, 130.2, 133.9 (m), 139.0, 139.4, 139.6, 142.1 (dm), 147.8 (dm), 157.6, 161.5; HRMS (ES+) calcd for [C$_{28}$H$_{30}$N$_{10}$O$_2$F$_4$S+H] 647.2288. found 647.2314; HPLC (I) t$_R$=12.74 min (98.92%), (II) t$_R$=19.07 min (98.14%).

N-(2-Aminoethyl)-N-(cyclohexylmethyl)pyridine-2-sulfonamide (19)

Mono-N-Boc-ethylenediamine (860 mg, 5.37 mmol, 1 equiv) was reacted with pyridine-2-sulfonyl chloride. The appropriate sulfonyl chloride (1.2 equiv) was added to a solution of the amine (1 equiv) and DIPEA (2 equiv) in anhydrous CH$_3$CN (0.1 M) at 0° C. The reaction was warmed to room temperature and stirred for 16 h, at which time the solvent was evaporated. The residue was re-dissolved in CH$_2$Cl$_2$, washed with 5% NaHCO$_3$, water, brine, dried (Na$_2$SO$_4$), filtered and concentrated. After work-up, the crude material was dry-loaded onto silica gel, and purified by flash column chromatography (eluent CH$_2$Cl$_2$/MeOH/NH$_4$OH, 92:7:1) to afford tert-butyl 2-(pyridine-2-sulfonamido)ethylcarbamate as a white powder (1.26 g, 80%): $\delta_H$ (400 MHz, DMSO-d$_6$) 0.89 (s, 9H, C(CH$_3$)$_3$), 2.04 (m, 2H, SO$_2$NHCH$_2$CH$_2$NHBoc), 2.86 (m, 2H, SO$_2$NHCH$_2$CH$_2$NHBoc), 6.30 (br, 1H, NHSO$_2$), 7.21 (m, 1H, CH (Py)), 7.414 (m, 1H, NHBoc), 7.47 (m, 1H, CH (Py)), 7.63, (m, 1H, CH (Py)), 8.27 (m, 1H, CH (Py)); $\delta_C$ (125 MHz, DMSO-d$_6$) 28.0, 39.9, 42.5, 77.6, 121.4, 126.8, 138.5, 149.8, 155.3, 157.7; HRMS (ES+) calcd for [C$_{12}$H$_{19}$N$_3$O$_4$S+H] 302.1175. found 302.1174. The sulfonamide NH of tert-butyl 2-(pyridine-2-sulfonamido)ethylcarbamate (1.1 g, 3.65 mmol, 1 equi) was then chemoselectively alkylated with cyclohexylmethyl bromide (840 mg, 4.75 mmol, 1.3 equiv), but the reaction was stirred for 4 days at room temperature. To a solution of the sulfonamide (1 equiv) and Cs$_2$CO$_3$ (2 equiv) in DMF (0.1 M) at 0° C. was added the appropriate alkyl bromide or chloride (1.1 equiv). The resulting mixture was stirred at room temperature overnight. The reaction was diluted with water, then extracted into EtOAc (×3). The combined EtOAc extractions were washed with 5% NaHCO$_3$ (×3), brine, dried (Na$_2$SO$_4$), filtered and concentrated. After work-up, the crude material was dry-loaded onto silica gel and purified by flash column chromatography (eluent CH$_2$Cl$_2$/MeOH/NH$_4$OH, 92:7:1) to furnish tert-butyl 2-(N-(cyclohexylmethyl)pyridine-2-sulfonamido)ethylcarbamate in quantitative yield (1.53 g) as a white solid: $\delta_H$ (500 MHz, DMSO-d$_6$) 0.77-0.83 (m, 2H, 2 CH (cyclohexylmethyl)), 1.09-1.19 (m, 3H, 3 CH (cyclohexylmethyl)), 1.36 (s, 9H, C(CH$_3$)$_3$), 1.54-1.65 (m, 6H, 6 CH (cyclohexylmethyl)), 3.03-3.07 (m, 4H, SO$_2$NCH$_2$CH$_2$NHBoc, NCH$_2$CH (cyclohexylmethyl)), 3.24 (t, J=7.0 Hz, 2H, SO$_2$NCH$_2$CH$_2$NHBoc), 6.79 (br, 1H, NHBoc), 7.67 (m, 1H, CH (Py)), 7.92 (m, 1H, CH (Py)), 8.09 (m, 1H, CH (Py)), 8.72 (m, 1H, CH (Py)); $\delta_C$ (125 MHz, DMSO-d$_6$) 25.1, 25.8, 28.0, 29.9, 35.6, 39.9, 48.4, 55.4, 77.6, 122.1, 127.0, 138.6, 150.0, 155.3, 157.1; HRMS (ES+) calcd for [C$_{19}$H$_{31}$N$_3$O$_4$S+H] 398.2114. found 398.2113. tert-Butyl 2-(N-(cyclohexylmethyl)pyridine-2-sulfonamido)ethylcarbamate (1.28 g, 3.22 mmol, 1 equiv) was dissolved in propan-2-ol (15 mL). Upon complete dissolution of the solid, 4 M HCl (15 mL) was added, and the reaction was stirred for one hour. All solvents were then evaporated. The residue was re-dissolved in CH$_2$Cl$_2$ (250 mL) and carefully washed with saturated NaHCO$_3$ (25 mL×3), dried (Na$_2$SO$_4$), filtered and concentrated to afford N-(2-aminoethyl)-N-(cyclohexylmethyl)pyridine-2-sulfonamide as a viscous oil (945 mg, 97%): $\delta_H$ (500 MHz, DMSO-d$_6$) 0.78-0.84 (m, 2H, 2 CH (cyclohexylmethyl)), 1.09-1.17 (m, 3H, 3 CH (cyclohexylmethyl)), 1.57-1.68 (m, 6H, 6 CH (cyclohexylmethyl)), 2.75 (t, J=7.0 Hz, 2H, NCH$_2$CH (cyclohexylmethyl)), 3.04 (t, J=7.4 Hz, 2H, SO$_2$NCH$_2$CH$_2$NH$_2$), 3.34 (t, J=7.4 Hz, 2H, SO$_2$NCH$_2$CH$_2$NH$_2$), 5.15 (br, 2H, NH$_2$), 7.68 (m, 1H, CH (Py)), 7.93 (m, 1H, CH (Py)), 8.10 (m, 1H, CH (Py)), 8.73 (m, 1H, CH (Py)); $\delta_C$ (125 MHz, DMSO) 25.1, 25.8, 29.9, 35.7, 49.4, 55.5, 66.2, 122.2, 127.1, 138.7, 150.0, 157.1; HRMS (ES+) calcd for [C$_{14}$H$_{23}$N$_3$O$_2$S+H] 298.1589. found 298.1589.

(2-β4-Cyanophenyl)((1-methyl-1H-imidazol-5-yl)methyl)amino)ethyl)-N-(cyclohexylmethyl)pyridine-2-sulfonamide (19a)

The primary amine of N-(2-aminoethyl)-N-(cyclohexylmethyl)pyridine-2-sulfonamide (19) was arylated with p-fluorobenzonitrile on a 0.336 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H$_2$O was added, and the crude product was extracted with EtOAc (×3). The EtOAc extractions were combined, washed with water (×3), brine, dried (Na$_2$SO$_4$), filtered and concentrated. After work-up and purification by silica gel flash column chromatography (eluent CH$_2$Cl$_2$/MeOH/NH$_4$OH, 192:7:1), N-(2-(4-cyanophenylamino)ethyl)-N-(cyclohexylmethyl)pyridine-2-sulfonamide was obtained as a colorless gum (119 mg, 89%): $\delta_H$ (500 MHz, DMSO-d$_6$) 0.77-0.83 (m, 2H, 2 CH (cyclohexylmethyl)), 1.09 (br, 3H, 3 CH (cyclohexyl)), 1.48-1.63 (m, 6H, 6 CH (cyclohexylmethyl)), 3.06 (d, J=6.4 Hz, 2H, NCH$_2$CH (cyclohexylmethyl)), 3.28-3.38 (m, 4H, SO$_2$NCH$_2$CH$_2$NHAr), 6.61 (d, J=8.5 Hz, 2H, 2 CH (Ar)), 6.70 (t, J=6.4 Hz, 1H, NH), 7.45 (d, J=8.5 Hz, 2H, 2 CH (Ar)), 7.66 (m, 1H, CH (Py)), 7.94 (m, 1H, CH (Py)), 8.07 (m, 1H, CH (Py)), 8.73 (m, 1H, CH (Py)); $\delta_C$ (125 MHz, DMSO) 25.1, 25.8, 29.9, 35.8, 41.5, 47.7, 55.6, 95.9, 111.6, 120.3, 122.2, 127.1, 133.3, 138.6, 150.1, 151.6, 157.0; HRMS (ES+) calcd for [C$_{21}$H$_{26}$N$_4$O$_2$S+H] 399.1855. found 399.1857. N-(2-(4-Cyanophenylamino)ethyl)-N-(cyclohexylmethyl)pyridine-2-sulfonamide was then alkylated with 5-chloromethyl-1H-imidazole.HCl on a 0.117 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. After work-up and chromatography over silica gel (eluent CH$_2$Cl$_2$/MeOH/NH$_4$OH, 192:7:1), the title compound N-(2-((4-cyanophenyl)((1-methyl-1H-imidazol-5-yl)methyl)amino)ethyl)-N-(cyclohexylmethyl)pyridine-2-sulfonamide was furnished as a glassy film (46 mg, 80%): $\delta_H$ (500 MHz, CDCl$_3$) 0.84-0.78 (m, 2H, 2 CH (cyclohexylmethyl)), 1.06-1.14 (m, 3H, 3 CH (cyclohexylmethyl)), 1.35-1.27 (m, 1H, CH (cyclohexylmethyl)), 1.66-1.59 (m, 5H, 5 CH (cyclohexylmethyl)), 2.95 (d, J=7.0 Hz, 2H, NCH$_2$CH (cyclohexyl)), 3.36 (t, J=7.9 Hz, 2H, SO$_2$NCH$_2$CH$_2$N), 3.61 (s, 3H, CH$_3$ (Im)), 3.65 (t, J=7.9 Hz, 2H, SO$_2$NCH$_2$CH$_2$N), 4.55 (s, 2H, CH$_2$Im), 6.85 (d, J=9.0 Hz, 2H, 2 CH (Ar)), 6.88 (s, 1H, CH (Im)), 7.47-7.44 (m, 3H, 2 CH (Ar), CH (Im)), 7.71 (s, 1H, CH (Py)), 7.91-7.86 (m, 2H, 2 CH (Py)), 8.61 (m, 1H, CH (Py)); δ$_C$ (125 MHz, CDCl$_3$) 25.6, 26.2, 30.6, 32.0, 36.9, 44.3, 46.8, 49.4, 57.1, 99.5, 112.3, 119.9, 122.5, 126.6, 127.2, 127.7, 133.8, 137.9, 138.7, 149.9, 150.4, 157.5; HRMS (ES+) calcd for [C$_{26}$H$_{32}$N$_6$O$_2$S+H] 493.2386. found 493.2364.

N-(2-β4-Cyano-2-fluorophenyl)((1-methyl-1H-imidazol-5-yl)methyl)amino)ethyl)-N-(cyclohexylmethyl)pyridine-2-sulfonamide (19b)

The primary amine of N-(2-aminoethyl)-N-(cyclohexylmethyl)pyridine-2-sulfonamide (19) was arylated with 3,4-difluorobenzonitrile on a 0.337 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H$_2$O was added, and the crude product was extracted with EtOAc (×3). The EtOAc extractions were combined, washed with water (×3), brine, dried (Na$_2$SO$_4$), filtered and concentrated. After work-up and purification by silica gel flash column chromatography (eluent CH$_2$Cl$_2$/MeOH/NH$_4$OH, 192:7:1), N-(2-(4-cyano-2-fluorophenylamino)ethyl)-N-(cyclohexylmethyl)pyridine-2-sulfonamide was obtained as a white foam (111 mg, 79%): δ$_H$ (500 MHz, DMSO-d$_6$) 0.83-0.77 (m, 2H, 2 CH (cyclohexylmethyl)), 1.09 (br, 3H, 3 CH (cyclohexylmethyl)), 1.62-1.51 (m, 6H, 6 CH (cyclohexylmethyl)), 3.06 (d, J=7.5 Hz, 2H, NCH$_2$CH (cyclohexyl)), 3.42-3.34 (m, 4H, SO$_2$NCH$_2$CH$_2$N), 6.54 (br, 1H, NHAr), 6.80 (t, J=8.5 Hz, 1H, CH (Ar)), 7.45 (dd, J=11.5, 1.5 Hz, 1H, CH (Ar)), 7.53 (dd, J=8.5, 1.5 Hz, 1H, CH (Ar)), 7.66 (m, 1H, CH (Py)), 7.93 (m, 1H, CH (Py)), 8.07 (m, 1H, CH (Py)), 8.71 (m, 1H, CH (Py)); δ$_C$ (125 MHz, DMSO-d$_6$) 25.1, 25.9, 30.0, 35.7, 37.1, 41.3, 47.5, 55.5, 61.8, 94.4, 122.2, 127.1, 130.4, 138.7, 140.7, 142.5, 150.1, 156.9, 179.7; HRMS (ES+) calcd for [C$_{21}$H$_{25}$FN$_4$O$_2$S+H] 417.1760. found 417.1749. N-(2-(4-Cyano-2-fluorophenylamino)ethyl)-N-(cyclohexylmethyl)pyridine-2-sulfonamide was then alkylated with 5-chloromethyl-1H-imidazole.HCl on a 0.216 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. After work-up and chromatography over silica gel (eluent CH$_2$Cl$_2$/MeOH/NH$_4$OH, 192:7:1), the title compound N-(2-((4-cyano-2-fluorophenyl)((1-methyl-1H-imidazol-5-yl)methyl)amino)ethyl)-N-(cyclohexylmethyl)pyridine-2-sulfonamide was afforded as a white foam (90 mg, 81%): δ$_H$ (500 MHz, CDCl$_3$) 0.68-0.75 (m, 2H, 2 CH (cyclohexylmethyl)), 1.03 (br, 3H, 3 CH (cyclohexylmethyl)), 1.23-1.32 (m, 1H, CH (cyclohexylmethyl)), 1.50-1.60 (m, 5H, 5 CH (cyclohexylmethyl)), 2.80 (s, 2H, NCH$_2$CH (cyclohexylmethyl)), 3.34-3.47 (m, 4H, SO$_2$NCH$_2$CH$_2$N), 3.54 (s, 3H, CH$_3$ (Im)), 4.46 (s, 2H, CH$_2$Im), 6.61 (br, 1H, CH (Ar)), 6.95 (s, 1H, CH (Im)), 7.11 (m, 1H, CH (Ar)), 7.26 (br, 1H, CH (Ar)), 7.53 (m, 2H, CH (Py), CH (Im)) 7.65 (br, 1H, CH (Py)), 8.26 (m, 1H, CH (Py)), 8.69 (m, 1H, CH (Py)); δ$_C$ (125 MHz, CDCl$_3$) 25.5, 26.1, 30.5, 31.3, 31.8, 36.6, 45.7, 47.3, 50.4, 56.4, 102.9, 118.1, 119.5, 120.2, 122.4, 126.5, 128.7, 129.3, 138.8, 141.3, 149.8, 153.9, 157.6, 162.4; HRMS (ES+) calcd for [C$_{26}$H$_{31}$FN$_6$O$_2$S+H] 511.2291. found 511.2265; HPLC (I) t$_R$=18.69 min (99.3%), (II) t$_R$=36.03 min (99.7%).

N-(2-β5-Cyanopyridin-2-yl)((1-methyl-1H-imidazol-5-yl)methyl)amino)ethyl)-N-(cyclohexylmethyl)pyridine-2-sulfonamide (19c)

The primary amine of N-(2-aminoethyl)-N-(cyclohexylmethyl)pyridine-2-sulfonamide (19) was arylated with 5-cyano-2-fluoropyridine on a 0.350 mmol scale. To a stirring solution of the primary amine (1 equiv) in DMSO (0.2 M) were added the aryl fluoride (1.2 equiv) and DIPEA (3 equiv). The reaction mixture was heated to 120° C. for 48 h. After allowing the reaction to cool, H$_2$O was added, and the crude product was extracted with EtOAc (×3). The EtOAc extractions were combined, washed with water (×3), brine, dried (Na$_2$SO$_4$), filtered and concentrated. After work-up and purification by silica gel flash column chromatography (eluent CH$_2$Cl$_2$/MeOH/NH$_4$OH, 192:7:1), N-(2-(5-cyanopyridin-2-ylamino)ethyl)-N-(cyclohexylmethyl)pyridine-2-sulfonamide was obtained as a colorless gum (115 mg, 82%): δ$_H$ (500 MHz, DMSO-d$_6$) 0.78-0.82 (m, 2H, 2 CH (cyclohexylmethyl)), 1.09 (br, 3H, 3 CH (cyclohexylmethyl)), 1.57-1.63 (m, 6H, 6 CH (cyclohexylmethyl)), 3.06 (d, J=7.5 Hz, 2H, NCH$_2$CH (cyclohexylmethyl)), 3.37-3.47 (m, 4H, SO$_2$NCH$_2$CH$_2$N), 6.50 (t, J=8.5 Hz, NH), 6.87 (d, J=9.0 Hz, 1H, CH (Ar)), 7.61-7.66 (m, 3H, 2 CH (Ar), CH (Py)), 7.92 (d, J=7.5 Hz, 1H, CH (Py)), 8.06 (m, 1H, CH (Py)), 8.36 (m, 1H, CH (Ar)), 8.71 (m, 1H, CH (Py)); δ$_C$ (125 MHz, DMSO-d$_6$) 25.1, 25.8, 30.0, 35.6, 46.7, 54.7, 55.5, 69.3, 94.7, 108.7, 118.7, 122.1, 126.9, 138.5, 150.0, 152.8, 157.0, 159.6; HRMS (ES+) calcd for [C$_{20}$H$_{25}$N$_5$O$_2$S+H] 400.1807. found 400.1795. N-(2-(5-Cyanopyridin-2-ylamino)ethyl)-N-(cyclohexylmethyl)pyridine-2-sulfonamide was then alkylated with 5-chloromethyl-1H-imidazole.HCl on a 0.240 mmol scale. The secondary aniline (1 equiv) was dissolved in DMF (0.07 M), then the reaction was cooled to 0° C. After 15 min, NaH (3 eq.) was added in one portion. After a further 15 min, 5-chloromethyl-1-methyl-1H-imidazole.HCl (1.1 eq) was added. The reaction was allowed to stir at 0° C. from 2-3 h, when TLC indicated the reaction was complete or had stalled. Upon quenching the reaction with brine (approximately 1 mL), the reaction was diluted with water and extracted with EtOAc (×3). The EtOAc extractions were combined, and washed with 5% NaHCO$_3$ (×3), brine, dried (Na$_2$SO$_4$), filtered and concentrated. After work-up and chromatography over silica gel (eluent CH$_2$Cl$_2$/MeOH/NH$_4$OH, 192:7:1), the title compound N-(2-((5-cyanopyridin-2-yl)((1-methyl-1H-imidazol-5-yl)methyl)amino)ethyl)-N-(cyclohexylmethyl)pyridine-2-sulfonamide was afforded as a white foam (110 mg, 93%): δ$_H$ (500 MHz, CDCl$_3$) 0.75-0.83 (m, 2H, 2 CH (cyclohexylmethyl)), 1.07-1.16 (m, 3H, 3 CH (cyclohexylmethyl)), 1.33-1.43 (m, 1H, CH (cyclohexylmethyl)), 1.59-1.65 (m, 5H, 5 CH (cyclohexylmethyl)), 2.94 (d, J=7.0 Hz, 2H, NCH$_2$CH (cyclohexylmethyl)), 3.28 (t, J=8.1 Hz, 2H, SO$_2$NCH$_2$CH$_2$N), 3.55 (s, 3H, CH$_3$ (Im)), 3.70 (t, J=8.1 Hz, 2H, SO$_2$NCH$_2$CH$_2$N), 4.89 (s, 2H, CH$_2$Im), 6.81 (d, J=9.0 Hz, 1H, CH (Ar)), 6.97 (s, 1H, CH (Im)), 7.45 (m, 1H, CH (Im)), 7.57 (s, 1H, CH (Ar)), 7.64 (m, 1H, CH (Ar)), 7.89-7.85 (m, 2H, 2 CH (Py)), 8.39-8.38 (m, 1H, CH (Ar)), 8.60 (m, 1H, CH (Py)); δ$_C$ (125 MHz, CDCl$_3$) 25.6, 26.2, 30.5, 32.0, 36.6, 40.9, 47.2, 56.8, 97.1, 105.9, 118.2, 122.5, 126.6, 127.4, 128.8, 137.9, 138.9, 140.2, 149.9, 152.3, 157.5, 158.4, 162.4;

HRMS (ES+) calcd for [$C_{25}H_{31}N_7O_2S$+H] 494.2338. found 494.2313; HPLC (I) $t_R$=18.15 min (99.5%), (II) $t_R$=34.66 min (97.4%)

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a dual farnesyltransferase and geranygeranyltransferase-I inhibitors (FGTIs), it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A composition, wherein the composition further comprises a compound of the general formula:

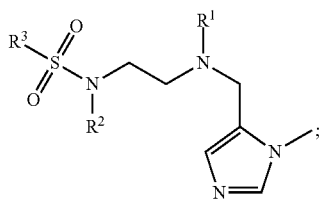

wherein $R^1$ is

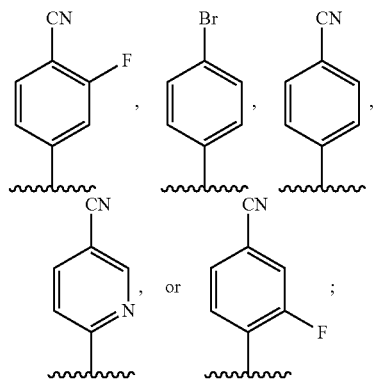

wherein $R^2$ is

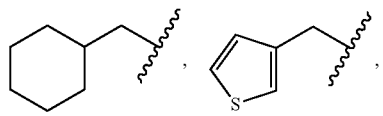

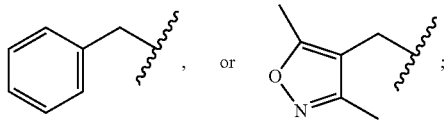

wherein $R^3$ is

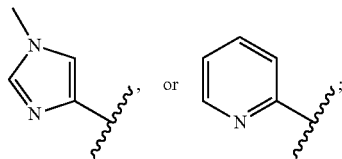

wherein $R^1$, $R^2$, and $R^3$ are not concurrently:
$R^1$ is

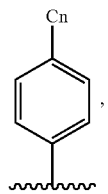

and $R^2$ is

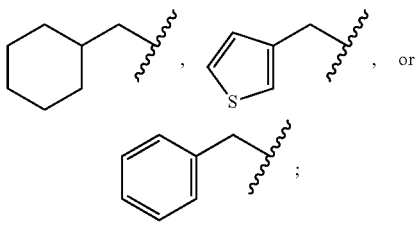

and
$R^1$ is

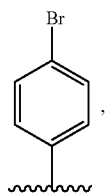

$R^2$ is

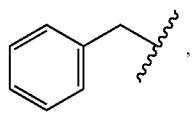 [SMILES: *Cc1ccccc1]

and $R^3$ is

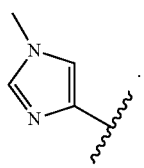

2. The composition of claim 1, wherein $R^1$ is

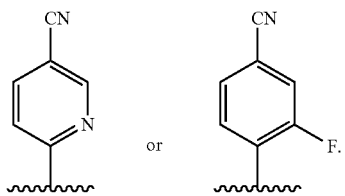 [SMILES: *c1ccc(C#N)cn1 ; "or" ; *c1ccc(C#N)cc1F] or

3. The composition of claim 1, wherein $R^1$ is

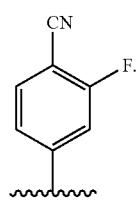 [SMILES: *c1ccc(C#N)c(F)c1]

4. The composition of claim 1, wherein $R^1$ is

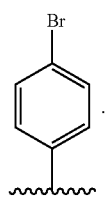

5. The composition of claim 1, wherein $R^1$ is

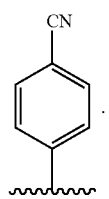

6. The composition of claim 2, wherein the composition further comprises a compound of the formula:

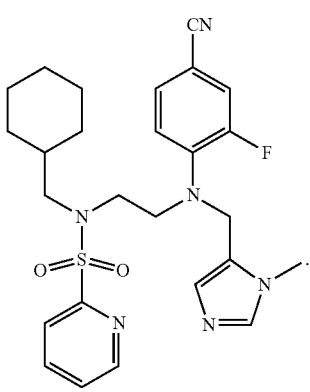 [SMILES: Cn1cncc1CN(CCN(CC1CCCCC1)S(=O)(=O)c1ccccn1)c1ccc(C#N)cc1F]

7. A method of treating cancer comprising administering a compound having the general formula:

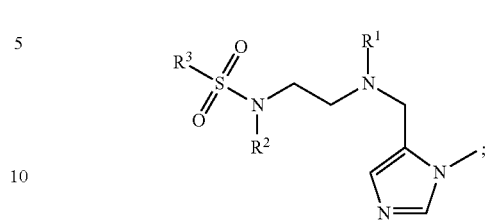

wherein $R^1$ is

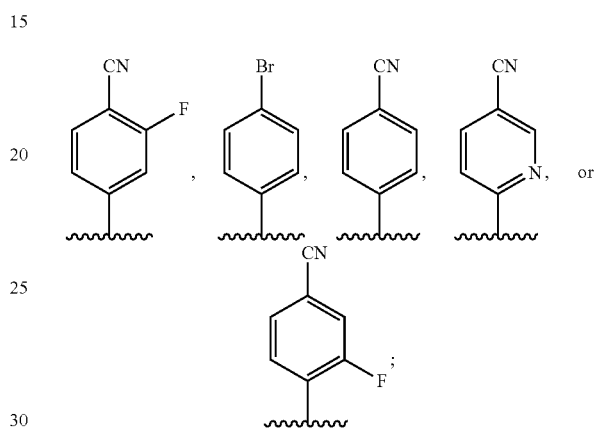

wherein $R^2$ is

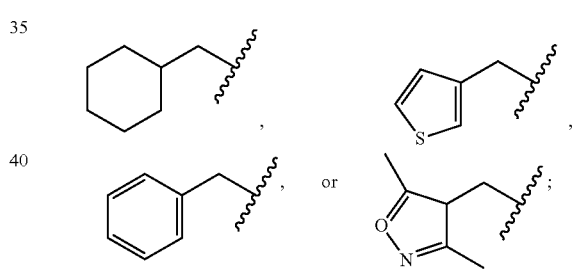

wherein $R^3$ is

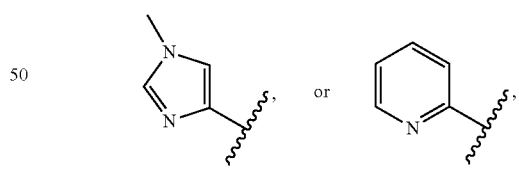

wherein $R^1$, $R^2$, and $R^3$ are not concurrently:
$R^1$ is

and R² is

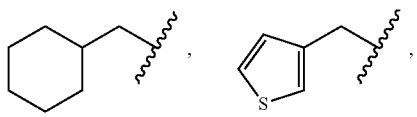, or

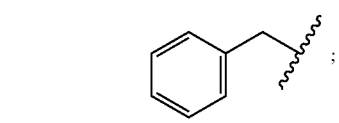;

R¹ is

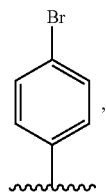,

R² is

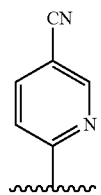, and R³ is 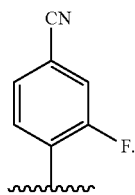;

and
where the cancer is pancreatic cancer, colonic cancer, lung cancer, or breast cancer.

8. The method of claim 7, wherein R¹ is

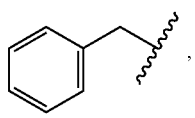 or 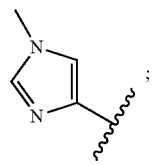

9. The method of claim 7, wherein R¹ is

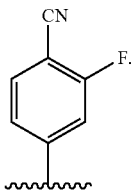

10. The method of claim 7, wherein R¹ is

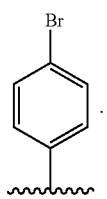

11. The method of claim 7, wherein R¹ is

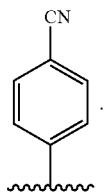

12. The method of claim 8, wherein the composition further comprises the formula:

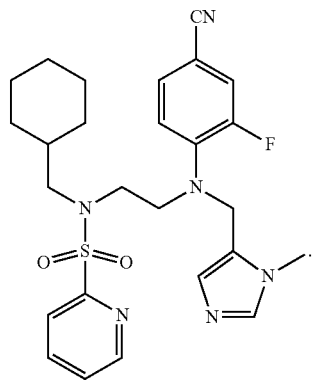 [SMILES: Cn1cncc1CN(CCN(CC1CCCCC1)S(=O)(=O)c1ccccn1)c1ccc(C#N)cc1F]

13. The method of claim 7, wherein the compound is administered at 50-100 mg/kg daily.

14. The method of claim 13, wherein the compound is administration orally or intravenously.

* * * * *